US006720182B1

(12) United States Patent
Savitzky et al.

(10) Patent No.: US 6,720,182 B1
(45) Date of Patent: Apr. 13, 2004

(54) ALTERNATIVE SPLICE VARIANTS OF CD40

(75) Inventors: Kinneret Savitzky, Tel Aviv (IL); Liat Mintz, Ramat Hasharon (IL); Sharon Engel, Ramat Hasharon (IL); Jeanne Bernstein, Kfar Yona (IL)

(73) Assignee: Compugen Ltd. Corporation, Tel Aviv (IL)

( * ) Notice: Subject to any disclaimer, the term of this patent is extended or adjusted under 35 U.S.C. 154(b) by 0 days.

(21) Appl. No.: 09/569,611

(22) Filed: May 10, 2000

(30) Foreign Application Priority Data

May 12, 1999 (IL) ........................................... 129907

(51) Int. Cl.[7] ........................ C07H 21/04; C12N 15/00; C12N 15/85; A61K 38/00

(52) U.S. Cl. ..................... 435/325; 536/23.5; 536/24.1; 536/23.1; 435/69.1; 435/70.1; 435/320.1; 435/252.3; 435/254.11; 514/12; 424/185.1; 424/278.1

(58) Field of Search ......................... 435/252.3, 254.11, 435/69.1, 69.4, 70.1, 325, 320.1; 536/23.1, 23.5, 24.1; 514/12, 44; 530/350; 424/185.1, 278.1

(56) References Cited

PUBLICATIONS

Scott, D et. al., The Pendred syndrome gene encodes a chloride–iodide transport protein. (1999), Nature Genetics, vol. 21, pp440–443.*

Ngo et al., 1994, The Protein Folding Problem and Tertiary Structure Prediction, pp. 492–495.*

Wells, Aditivity of Mutational Effects in Proteins, 1990, Biochemistry, vol. 26, No:37, pp. 8509–8517.*

Stamenkovic et al., A B–lymphocyte activation molecule related to the nerve growth factor receptor and induced by cytokines in carcinomas (1989), The EMBO J., vol. 8, No. 5, pp1403–1410.*

Chabot, B., “Directing Alternative Splicing: cast and scenarios” *TIG*, vol. 12, No. 11, pp. 472–478, (Nov. 1996).

Breitbart, R. et al., “Alternative Splicing: A Ubiquitous Mechanism For The Generation Of Multiple Protein Isoforms From Single Genes” *Ann. Rev. Biochem.*, vol. 56, pp. 467–495, (1987).

Stamm, S. et al., “A Sequence Compilation and Comparison Of Exons That Are Alternatively Spliced In Neurons” *Nucleic Acids Research* vol. 22, No. 9, pp. 1515–1526, (1994).

Gelfand, D. et al., “ASDB:Database Of Alternatively Spliced Genes” *Nucleic Acids Research*, vol. 27, No. 1, p. 301, (1998).

Sharp P., et al., “Split Genes And RNA Splicing” *Cell*, vol. 77, pp. 805–815, (Jun. 17, 1994).

Smith C., et al., “Alternative Splicing In The Control Of Gene Expression”, *Annu. Rev. Genet*, vol. 23, pp. 527–577, (1989).

* cited by examiner

*Primary Examiner*—Lorraine Spector
*Assistant Examiner*—Jegatheesan Seharaseyon
(74) *Attorney, Agent, or Firm*—Birch, Stewart, Kolasch & Birch, LLP

(57) ABSTRACT

The invention concerns novel nucleic acid sequences and amino acid sequences obtained by alternative splicing, expression vectors, host cell and pharmaceutical compositions comprising said sequences.

6 Claims, No Drawings

SEQUENCE LISTING

<160> NUMBER OF SEQ ID NOS: 52

<210> SEQ ID NO 1
<211> LENGTH: 4041
<212> TYPE: DNA
<213> ORGANISM: Homo sapiens

<400> SEQUENCE: 1

```
tgtgccccag cctggatatt cgctcagagg tggcagagct tcgtcagctg gagaactgca     60
gcgtggtgga gggccacctg cagatcctgc tcatgttcac agccaccggg gaggacttcc    120
gcggcctcag cttccctcgc ctcacccagg tcaccgacta cctgctgctc ttccgtgtct    180
acggactgga gagcctgcgc gacctcttcc ccaacctagc agtcatccgc gggacgcgcc    240
tcttcctggg ctatgcactg gtcatctttg agatgccaca tctgcgtgac gtggcactgc    300
ctgcacttgg ggccgtgctg cgtggggctg tgcgtgtgga gaagaaccag gagctctgcc    360
acctctccac cattgactgg ggactgctgc agccagcacc tggcgccaac cacatcgtgg    420
gcaacaagct gggcgaggag tgtgctgacg tgtgccctgg tgtgctgggt gctgctggtg    480
agccctgtgc caagaccacc ttcagcgggc acactgacta cagatgctgg acctccagcc    540
actgccagag agtgtgcccc tgcccccatg ggatggcttg cacagcgagg ggcgagtgct    600
gccacaccga atgcctgggg ggctgcagcc agccagaaga ccctcgtgcc tgtgtagctt    660
gccgccacct ctacttccag ggtgcctgcc tgtgggcctg cccgccaggc acctaccagt    720
atgagtcctg gcgctgtgtc acagctgagc gctgtgccag cctgcactct gtgcccggcc    780
gtgcctccac cttcggcata caccagggca gttgcctggc ccagtgccct tctggcttca    840
cccgtaatag cagcagcata ttctgccaca agtgcgaggg gctgtgccct aaagagtgca    900
aggtaggcac caagaccatc gactccatcc aggcggcaca ggatcttgtg ggctgcacgc    960
atgtggaggg aagcctcatc ctcaaccttc gccagggcta caacctggag ccacagctgc   1020
agcacagcct ggggctggta gaaaccatta ctggcttcct caaaatcaag cactcctttg   1080
ccctcgtgtc cctgggcttt ttcaagaacc tcaaactaat ccggggagac gccatggtgg   1140
atgggaacta cactctctac gtgctggaca accagaacct acaacagcta gggtcctggg   1200
tggccgcggg gctcaccatt cccgtgggca agatctactt cgccttcaac ccgcgcctct   1260
gcttggaaca catctaccga ctggaggagg tgacaggcac gcgaggtcgg cagaacaagg   1320
ctgagatcaa cccccgcacc aacggagacc gcgccgcctg ccagactcgc accctgcgct   1380
tcgtgtccaa cgtgacggag gcagaccgca tcctgctacg ctgggagcgc tatgagccac   1440
tggaggcccg cgacctgctc agcttcatcg tgtactacaa ggagtcccca ttccagaacg   1500
ccacagagca cgtgggtcca gatgcttgtg gaacccagag ctggaacctg ctggatgtgg   1560
agctgcccct aagccgcacc caggagccag ggtgaccct agcctccctc aagccttgga   1620
cacagtacgc agtgtttgtg cgggccatca cgctaaccac tgaggaggac agccctcatc   1680
aaggagccca gagtcccatc gtctacctcc gaacgctgcc tgcagctccc acggtgcccc   1740
aagacgtcat ctccacgtcc aactcctcct cccacctcct ggtgcgctgg aagccaccga   1800
cccagcgcaa tgggaacctc acctactacc tggtgctgtg gcagcggctg gcagaggacg   1860
gcgacctcta cctcaatgac tactgccacc gcggcttgcg gctgcccacc agcaacaacg   1920
atccgcgctt cgacggcgaa gacggggatc ctgaggccga gatggagtcc gactgctgcc   1980
cttgccagca cccacctcct ggtcaggttc tgcccccgct ggaggcgcaa gaggcctcgt   2040
```

-continued

```
tccagaagaa gtttgaaaac tttctacaca acgcgatcac catccccata tccccttgga   2100
aggtgacgtc catcaacaag agcccccaaa gggactcagg gcggcaccgc cgggcagctg   2160
ggcccctccg gctgggggc aacagctcgg atttcgagat ccaggaggac aaggtgcccc   2220
gtgagcgagc ggtgctgagc ggcctgcgcc acttcacgga ataccggatc gacatccatg   2280
cctgcaacca cgcggcgcac accgtgggct gcagcgccgc caccttcgtc tttgcgcgca   2340
ccatgcccca cagtaggtga tccacacaca caccttctac ccccatcacc gaccccaagg   2400
accctgtgca aaggtttggg gtttgacttc tcgctaaccc cagagccacg ctttgcttgc   2460
ccctctcagt tcccataatc ccaaagcttt ccccacctcc cagctcagcc cagtttagct   2520
tgggtttgaa cataaggtga gatgaaccac ttttggcccg gctgctggat gccccttccc   2580
gcaggagagg ctgatggtat tccaggaaag gtggcctggg aggcctccag caagaacagt   2640
gtccttctgc gctggctcga gccaccagac ccccaacggac tcatcctcaa gtacgaaatc   2700
aagtaccgcc gcttgggaga ggaggccaca gtgctgtgtg tgtcccgtct tcgatatgcg   2760
aagtttgggg gagtccacct ggccctgctg ccccctggaa actactctgc cagggttagg   2820
gcaacctcac tggctggcaa tggctcttgg acagacagtg ttgccttcta catccttggc   2880
ccagaggagg aggatgctgg ggggctgcat gtcctcctca ctgccacccc tgtggggctc   2940
acgctgctca tcgttcttgc tgcccttggt ttcttctacg gcaagaagag aaacagaacc   3000
ctgtatgctt ctgtgaatcc agagtacttc agcgcctctg atatgtatgt ccctgatgaa   3060
tgggaggtgc ctcgggagca gatctcgata atccgggaac tgggccaggg ctcttttggg   3120
atggtatatg aggggctggc acgaggactt gaggctggag aggagtccac acccgtggcc   3180
ctgaagacgg tgaatgagct ggccagccca cgggaatgca ttgagttcct caaggaagct   3240
tctgtcatga aagccttcaa gtgtcaccat gtggtgcgtc tcctgggtgt ggtatctcag   3300
ggccagccaa ctctggtcat catggagtta atgacccgtg ggacctcaa gagccatctt   3360
cgatctttgc ggcctgaggc agagaacaac cctgggctcc cacagccagc attgggggaa   3420
atgatccaaa tggctggtga gattgcagac ggcatggcct accttgctgc caacaagttt   3480
gtgcaccgag atctagcagc ccgcaactgc atggtgtccc aggacttcac cgtcaagatc   3540
ggggacttcg ggatgactcg ggacgtgtat gagacagact attaccgcaa gggtgggaag   3600
gggctgctgc ccgtgcgctg gatggccccc gagtccctca aagatgggat cttcaccacc   3660
cactcggatg tctggtcctt tggcgtggta ctctgggaga ttgtgaccct ggcagaacaa   3720
ccctaccagg gcctgtccaa tgagcaggtg ctgaagttcg tcatggatgg cggggtcctg   3780
gaggagctgg agggctgtcc ccttcagctg caggagctga tgagccgctg ctggcagccg   3840
aacccacgcc tgcgcccatc tttcacacac attctggaca gcatacagga ggagctgcgg   3900
ccctccttcc gcctcctctc cttctactac agcccggaat gccgggggc ccggggctcc   3960
ctgcctacca ccgatgcaga gcctgactcc tcacccactc caagagactg cagccctcaa   4020
aatgggggtc cagggcactg a                                               4041
```

<210> SEQ ID NO 2
<211> LENGTH: 536
<212> TYPE: DNA
<213> ORGANISM: Homo sapiens

<400> SEQUENCE: 2

```
agccacccgg cccaagttga agaagatgaa gagccagacg ggacaggtgg gtgagaagca     60
```

-continued

```
atcgctgaag tgtgaggcag cagcgggtaa tccccagcct tcctaccgtt ggttcaagga    120

tggcaaggag ctcaaccgca gccgagacat tcgcatcaaa tatggcaacg gcagaaagaa    180

ctcacgacta cagttcaaca aggtgaaggt ggaggacgct ggggagtatg tctgcgaggc    240

cgagaacatc ctggggaagg acaccgtccg ggccggctt tacgtcaaca gcgtgagcac    300

caccctgtca tcctggtcgg ggcacgcccg gaagtgcaac gagacagcca agtcctattg    360

cgtcaatgga ggcgtctgct actacatcga gggcatcaac cagctctcct gcaaggcacc    420

tgggctgcac tgcttagaac ttggtaccca gagccaccac ttccccatct cagcctcccc    480

tggttccagc caaggttcct ggaaccaact tccccaacac cctttgtcag ccctcg    536
```

<210> SEQ ID NO 3
<211> LENGTH: 2157
<212> TYPE: DNA
<213> ORGANISM: Homo sapiens

<400> SEQUENCE: 3

```
gggccgggca agaagcaccc agagggagga agcgggagag ggagcccgat cccgggagaa     60

agccacccgg cccaagttga agaagatgaa gagccagacg ggacaggtgg gtgagaagca    120

atcgctgaag tgtgaggcag cagcgggtaa tccccagcct tcctaccgtt ggttcaagga    180

tggcaaggag ctcaaccgca gccgagacat tcgcatcaaa tatggcaacg gcagaaagaa    240

ctcacgacta cagttcaaca aggtgaaggt ggaggacgct ggggagtatg tctgcgaggc    300

cgagaacatc ctggggaagg acaccgtccg ggccggctt tacgtcaaca gcgtgagcac    360

caccctgtca tcctggtcgg ggcacgcccg gaagtgcaac gagacagcca agtcctattg    420

cgtcaatgga ggcgtctgct actacatcga gggcatcaac cagctctcct gcaaatgtcc    480

aaatggattc ttcggacaga gatgtttgga gaaactgcct ttgcgattgt acatgccaga    540

tcctaagcaa aaagccgagg agctgtacca gaagagggtc ctgaccatca cgggcatctg    600

cgtggctctg ctggtcgtgg gcatcgtctg tgtggtggcc tactgcaaga ccaaaaaaca    660

gcggaagcag atgcacaacc acctccggca gaacatgtgc ccggcccatc agaaccggag    720

cttggccaat gggcccagcc acccccggct ggacccagag gagatccaga tggcagatta    780

tatttccaag aacgtgccag ccacagacca tgtcatcagg agagaaactg agaccacctt    840

ctctgggagc cactcctgtt ctccttctca ccactgctcc acagccacac ccacctccag    900

ccacagacac gagagccaca cgtggagcct ggaacgttct gagagcctga cttctgactc    960

ccagtcgggg atcatgctat catcagtggg taccagcaaa tgcaacagcc cagcatgtgt   1020

ggaggcccgg gcaaggcggg cagcagccta caacctggag gagcggcgca gggccaccgc   1080

gccaccctat cacgattccg tggactccct tcgcgactcc ccacacagcg agaggtacgt   1140

gtcggccctg accacgcccg cgcgcctctc gcccgtggac ttccactact cgctggccac   1200

gcaggtgcca actttcgaga tcacgtcccc caactcggcg cacgccgtgt cgctgccgcc   1260

ggcggcgccc atcagttacc gcctggccga gcagcagccg ttactgcggc acccggcgcc   1320

ccccggcccg ggacccggac ccgggcccgg gcccgggccc ggcgcagaca tgcagcgcag   1380

ctatgacagc tactattacc ccgcggcggg gcccggaccg cggcgcggga cctgcgcgct   1440

cggcggcagc ctgggcagcc tgcctgccag cccettccgc atccccgagg acgacgagta   1500

cgagaccacg caggagtgcg cgccccgcc gccgccgcgg ccgcgcgcgc gcggtgcgtc   1560

ccgcaggacg tcggcggggc ccggcgctg gcgccgctcg cgcctcaacg ggctggcggc   1620

gcagcgcgca cgggcggcga gggactcgct gtcgctgagc agcggctcgg gcggcggctc   1680
```

-continued

```
agcctcggcg tcggacgacg acgcggacga cgcggacggg gcgctggcgg ccgagagcac   1740

acctttcctg ggcctgcgtg gggcgcacga cgcgctgcgc tcggactcgc cgccactgtg   1800

cccggcggcc gacagcagga cttactactc actggacagc cacagcacgc gggccagcag   1860

cagacacagc cgcgggccgc ccccgcgggc caagcaggac tcggcgccac tctagggccc   1920

cgccgcgcgc ccctccgccc cgcccgcccc actatcttta aggagaccag agaccgccta   1980

ctggagagaa aggaggaaaa aagaaataaa aatattttta ttttctataa aaggaaaaaa   2040

gtataacaaa atgttttatt ttcattttag caaaaattgt cttataatac tagctaacgg   2100

caaaggcgtt tttataggga aactatttat atgtaacatc ctgatttaca gcttcgg      2157
```

<210> SEQ ID NO 4
<211> LENGTH: 1459
<212> TYPE: DNA
<213> ORGANISM: Homo sapiens

<400> SEQUENCE: 4

```
cctccaggtc ctggcgcaca gggtgggagc gctgcgctgc gccgcgctgc gcatcgcggc     60

ccgcttgccg cctgcccccct gccctagctg ggccacctcc ccgggctgcc ggtggagggc   120

taagaggcgc taacgttacg ctgtttccgg ttttccagcg ggctctgttt cccctcccaa    180

ggcggcggcg gctgagcggc ggagcccccc aaatggcctg gccagatgcg gcaggtttgc    240

tgctcagcgc tgccgccgcc gccactggag aagggtcggt gcagcagcta cagcgacagc    300

agcagcagca gcagcgagag gagcagcagc agcagcagca gcagcagcga gagcggcagc    360

agcagcagga gcagcagcaa caacagcagc atctctcgtc ccgctgcgcc cccagmgccg    420

cggccgcagc aacagccgca gccccgcagc cccgcagccc ggagagccgc cgcccgttcg    480

cgagccgcag ccgccggcgg catgaggcgc gacccggccc ccggcttctc catgctgctc    540

ttcggtgtgt cgctcgcctg ctactcgccc agcctcaagt cagtgcagga ccaggcgtac    600

aaggcacccg tggtggtgga gggcaaggta caggggctgg tcccagccgg cggctccagc    660

tccaacagca cccgagagcc gcccgcctcg ggtcgggtgg cgttggtaaa ggtgctggac    720

aagtggccgc tccggagcgg ggggctgcag cgcgagcagg tgatcagcgt gggctcctgt    780

gtgccgctcg aaaggaacca gcgctacatc tttttcctgg agcccacgga acagccctta    840

gtctttaaga cggcctttgc ccccctcgat accaacggca aaaatctcaa gaaagaggtg    900

ggcaagatcc tgtgcactga ctgcgccacc cggcccaagt tgaagaagat gaagagccag    960

acgggacagg tgggtgagaa gcaatcgctg aagtgtgagg cagcagcggg taatccccag   1020

ccttcctacc gttggttcaa ggatggcaag gagctcaacc gcagccgaga cattcgcatc   1080

aaatatggca acggcagaaa gaactcacga ctacagttca acaaggtgaa ggtggaggac   1140

gctggggagt atgtctgcga ggccgagaac atcctgggga aggacaccgt ccggggccgg   1200

ctttacgtca acagcgtgag caccaccctg tcatcctggt cggggcacgc ccggaagtgc   1260

aacgagacag ccaagtccta ttgcgtcaat ggaggcgtct gctactacat cgagggcatc   1320

aaccagctct cctgcaaggc acctgggctg cactgcttag aacttggtac ccagagccac   1380

cacttcccca tctcagcctc ccctggttcc agccaaggtt cctggaacca acttccccaa   1440

caccctttgt cagccctcg                                                1459
```

<210> SEQ ID NO 5
<211> LENGTH: 2734
<212> TYPE: DNA

-continued

<213> ORGANISM: Homo sapiens

<400> SEQUENCE: 5

```
ttcaaacccc ccttaaacta attgtcacaa agktggataa tattgatgga atycctcaat     60
tggaggatca aagttgagaa aagtaatatt cgacattttt cgattcaacg gagtggccac    120
caagacgatg tcatagaagt ctgaacgagt ctcagttcca atttggtaga ccacttcata    180
catctttgtt ggatttcctg tgtacttggt ctttgttttc tcctcgatgt acattactga    240
gccagatata agattgcttt tggatgcctg cagaagccct gagcaaacaa gtttattgcc    300
accttctact gcccaaaggc cagaatcaga acaggacagt gacaccgccc ccacaaaggc    360
attgatgtcc gtgctttggc cataattgac cctcataaca ggagcaatca tttcattgag    420
gaacttctca gaaaagccgg ccttttgcaa ggtttcaaga agtgttcgat taagcattcc    480
aaggaagtca tctcctccta gagcatgaag taatttttcg acactactga aggcatagtc    540
atgagactgg tagcggtaga tcctcatgaa cttgtctaac acgtcctcta cccacatgtg    600
catacggagg gattgaaatc catagcgcca aactaattta atcacgttaa ttatgaacca    660
gttgctctcc tcaaatacca gagtctctcc attatatatc cccagtaggc cacccagagg    720
ctgatgctca ccatggggcg cctgcaactg gttgtgttgg gcctcacctg ctgctgggca    780
gtggcgagtg ccgcgaagct gggcgccgtg tacacagaag gtgggttcgt ggaaggcgtc    840
aataagaagc tcggcctcct gggtgactct gtggacatct tcaagggcat cccctttcgca    900
gctcccacca aggccctgga aaatcctcag ccacatcctg gctggcaagg gaccctgaag    960
gccaagaact tcaagaagag atgcctgcag gccaccatca cccaggacag cacctacggg   1020
gatgaagact gcctgtacct caacatttgg gtgccccagg gcaggaagca agtctcccgg   1080
gacctgcccg ttatgatctg gatctatgga ggcgccttcc tcatggggtc cggccatggg   1140
gccaacttcc tcaacaacta cctgtatgac ggcgaggaga tcgccacacg cggaaacgtc   1200
atcgtggtca ccttcaacta ccgtgtcggc cccccttgggt tcctcagcac tggggacgcc   1260
aatctgccag gtaactatgg tcttcgggat cagcacatgg ccattgcttg ggtgaagagg   1320
aatatcgcgg ccttcggggg ggaccccaac aacatcacgc tcttcgggga gtctgctgga   1380
ggtgccagcg tctctctgca gaccctctcc ccctacaaca agggcctcat ccggcgagcc   1440
atcagccaga gcggcgtggc cctgagtccc tgggtcatcc agaaaaaccc actcttctgg   1500
gccaaaaagg tggctgagaa ggtgggttgc cctgtgggtg atgccgccag gatggcccag   1560
tgtctgaagg ttactgatcc ccgagccctg acgctggcct ataaggtgcc gctggcaggc   1620
ctggagtacc ccatgctgca ctatgtgggc ttcgtccctg tcattgatgg agacttcatc   1680
cccgctgacc cgatcaacct gtacgccaac gccgccgaca tcgactatat agcaggcacc   1740
aacaacatgg acggccacat cttcgccagc atcgacatgc ctgccatcaa caagggcaac   1800
aagaaagtca cggaggagga cttctacaag ctggtcagtg agttcacaat caccaagggg   1860
ctcagaggcg ccaagacgac ctttgatgtc tacaccgagt cctgggccca ggacccatcc   1920
caggagaata agaagaagac tgtggtggac tttgagaccg atgtcctctt cctggtgccc   1980
accgagattg ccctagccca gcacagagcc aatgccaaga gtgccaagac ctacgcctac   2040
ctgttttccc atccctctcg gatgcccgtc taccccaaat gggtgggggc cgaccatgca   2100
gatgacattc agtacgtttt cgggaagccc ttcgccaccc ccacgggcta ccggccccaa   2160
gacaggacag tctctaaggc catgatcgcc tactggacca actttgccaa aacaggggac   2220
cccaacatgg gcgactcggc tgtgcccaca cactgggaac cctacactac ggaaaacagc   2280
```

-continued

```
ggctacctgg agatcaccaa gaagatgggc agcagctcca tgaagcggag cctgagaacc   2340
aacttcctgc gctactggac cctcacctat ctggcgctgc ccacagtgac cgaccaggag   2400
gccacccctg tgccccccac aggggactcc gaggccactc ccgtgccccc cacgggtgac   2460
tccgagaccg cccccgtgcc gcccacgggt gactccgggg ccccccccgt gccgcccacg   2520
ggtgactccg gggccccccc cgtgccgccc acgggtgact ccggggcccc ccccgtgccg   2580
cccacgggtg actccaagga agctcagatg cctgcagtca ttaggtttta gcgtcccatg   2640
agccttggta tcaagaggcc acaagagtgg gaccccaggg gctcccctcc catcttgagc   2700
tcttcctgaa taaagcctca tacccctgaa aaaa                                2734
```

<210> SEQ ID NO 6
<211> LENGTH: 2781
<212> TYPE: DNA
<213> ORGANISM: Homo sapiens

<400> SEQUENCE: 6

```
ttcaaacccc ccttaaacta attgtcacaa agktggataa tattgatgga atycctcaat     60
tggaggatca aagttgagaa aagtaatatt cgacattttt cgattcaacg gagtggccac    120
caagacgatg tcatagaagt ctgaacgagt ctcagttcca atttggtaga ccacttcata    180
catctttgtt ggatttcctg tgtacttggt ctttgttttc tcctcgatgt acattactga    240
gccagatata agattgcttt tggatgcctg cagaagccct gagcaaacaa gtttattgcc    300
accttctact gcccaaaggc cagaatcaga acaggacagt gacaccgccc ccacaaaggc    360
attgatgtcc gtgctttggc cataattgac cctcataaca ggagcaatca tttcattgag    420
gaacttctca gaaaagccgg ccttttgcaa ggtttcaaga agtgttcgat taagcattcc    480
aaggaagtca tctcctccta gagcatgaag taatttttcg acactactga aggcatagtc    540
atgagactgg tagcggtaga tcctcatgaa cttgtctaac acgtcctcta cccacatgtg    600
catacggagg gattgaaatc catagcgcca aactaattta atcacgttaa ttatgaacca    660
gttgctctcc tcaaatacca gagtctctcc attatatatc cccagtaggc cacccagagg    720
ctgatgctca ccatggggcg cctgcaactg gttgtgttgg gcctcacctg ctgctgggca    780
gtggcgagtg ccgcgaagct gggcgccgtg tacacagaag gtgggttcgt ggaaggcgtc    840
aataagaagc tcggcctcct gggtgactct gtggacatct tcaagggcat ccccttcgca    900
gctcccacca aggccctgga aaatcctcag ccacatcctg gctggcaagg gaccctgaag    960
gccaagaact tcaagaagag atgcctgcag gccaccatca cccaggacag cacctacggg   1020
gatgaagact gcctgtacct caacatttgg gtgccccagg gcaggaagca agtctcccgg   1080
gacctgcccg ttatgatctg gatctatgga ggcgccttcc tcatggggtc cggccatggg   1140
gccaacttcc tcaacaacta cctgtatgac ggcgaggaga tcgccacacg cggaaacgtc   1200
atcgtggtca ccttcaacta ccgtgtcggc ccccttgggt tcctcagcac tggggacgcc   1260
aatctgccag gtaactatgg tcttcgggat cagcacatgg ccattgcttg ggtgaagagg   1320
aatatcgcgg ccttcggggg ggaccccaac aacatcacgc tcttcgggga gtctgctgga   1380
ggtgccagcg tctctctgca gaccctctcc ccctacaaca agggcctcat ccggcgagcc   1440
atcagccaga gcggcgtggc cctgagtccc tgggtcatcc agaaaaaccc actcttctgg   1500
gccaaaaagg tggctgagaa ggtgggttgc cctgtgggtg atgccgccag gatggcccag   1560
tgtctgaagg ttactgatcc ccgagccctg acgctggcct ataaggtgcc gctggcaggc   1620
```

-continued

```
ctggagtacc ccatgctgca ctatgtgggc ttcgtccctg tcattgatgg agacttcatc   1680

cccgctgacc cgatcaacct gtacgccaac gccgccgaca tcgactatat agcaggcacc   1740

aacaacatgg acggccacat cttcgccagc atcgacatgc ctgccatcaa caagggcaac   1800

aagaaagtca cggaggagga cttctacaag ctggtcagtg agttcacaat caccaagggg   1860

ctcagaggcg ccaagacgac ctttgatgtc tacaccgagt cctgggccca ggacccatcc   1920

caggagaata agaagaagac tgtggtggac tttgagaccg atgtcctctt cctggtgccc   1980

accgagattg ccctagccca gcacagagcc aatgccaaga gtgccaagac ctacgcctac   2040

ctgttttccc atccctctcg gatgcccgtc taccccaaat gggtgggggc cgaccatgca   2100

gatgacattc agtacgtttt cgggaagccc ttcgccaccc ccacgggcta ccggccccaa   2160

gacaggacag tctctaaggc catgatcgcc tactggacca actttgccaa aacaggggac   2220

cccaacatgg gcgactcggc tgtgcccaca cactgggaac cctacactac ggaaaacagc   2280

ggctacctgg agatcaccaa gaagatgggc agcagctcca tgaagcggag cctgagaacc   2340

aacttcctgc gctactggac cctcacctat ctggcgctgc ccacagtgac cgaccaggag   2400

gccacccctg tgccccccac aggggactcc gaggccactc ccgtgccccc cacgggtgac   2460

tccgagaccg cccccgtgcc gcccacgggt gactccgggg cccccccgt gccgcccacg   2520

ggtgactccg gggcccccc cgtgccgccc acgggtgact ccggggcccc ccccgtgccg   2580

cccacggggt gccccccacg ggtgactctg aggctgcccc tgtgcccccc acagatgact   2640

ccaaggaagc tcagatgcct gcagtcatta ggttttagcg tcccatgagc cttggtatca   2700

agaggccaca agagtgggac cccaggggct cccctcccat cttgagctct tcctgaataa   2760

agcctcatac ccctgaaaaa a                                              2781
```

```
<210> SEQ ID NO 7
<211> LENGTH: 1905
<212> TYPE: DNA
<213> ORGANISM: Homo sapiens

<400> SEQUENCE: 7

ttcaaacccc ccttaaacta attgtcacaa agktggataa tattgatgga atycctcaat     60

tggaggatca aagttgagaa aagtaatatt cgacattttt cgattcaacg gagtggccac    120

caagacgatg tcatagaagt ctgaacgagt ctcagttcca atttggtaga ccacttcata    180

catctttgtt ggatttcctg tgtacttggt ctttgttttc tcctcgatgt acattactga    240

gccagatata agattgcttt tggatgcctg cagaagccct gagcaaacaa gtttattgcc    300

accttctact gcccaaaggc cagaatcaga acaggacagt gacaccgccc ccacaaaggc    360

attgatgtcc gtgctttggc cataattgac cctcataaca ggagcaatca tttcattgag    420

gaacttctca gaaaagccgg ccttttgcaa ggtttcaaga agtgttcgat taagcattcc    480

aaggaagtca tctcctccta gagcatgaag taatttttcg acactactga aggcatagtc    540

atgagactgg tagcggtaga tcctcatgaa cttgtctaac acgtcctcta cccacatgtg    600

catacggagg gattgaaatc catagcgcca aactaattta atcacgttaa ttatgaacca    660

gttgctctcc tcaaatacca gagtctctcc attatatatc cccagtaggc cacccagagg    720

ctgatgctca ccatggggcg cctgcaactg gttgtgttgg gcctcacctg ctgctgggca    780

gtggcgagtg ccgcgaagac cccatgctgc actatgtggg cttcgtccct gtcattgatg    840

gagacttcat ccccgctgac ccgatcaacc tgtacgccaa cgccgccgac atcgactata    900

tagcaggcac caacaacatg gacggccaca tcttcgccag catcgacatg cctgccatca    960
```

```
acaagggcaa caagaaagtc acggaggagg acttctacaa gctggtcagt gagttcacaa   1020

tcaccaaggg gctcagaggc gccaagacga cctttgatgt ctacaccgag tcctgggccc   1080

aggacccatc ccaggagaat aagaagaaga ctgtggtgga ctttgagacc gatgtcctct   1140

tcctggtgcc caccgagatt gccctagccc agcacagagc caatgccaag agtgccaaga   1200

cctacgccta cctgttttcc catccctctc ggatgcccgt ctaccccaaa tgggtggggg   1260

ccgaccatgc agatgacatt cagtacgttt tcgggaagcc cttcgccacc cccacgggct   1320

accggcccca agacaggaca gtctctaagg ccatgatcgc ctactggacc aactttgcca   1380

aaacagggga ccccaacatg ggcgactcgg ctgtgcccac acactgggaa ccctacacta   1440

cggaaaacag cggctacctg gagatcacca agaagatggg cagcagctcc atgaagcgga   1500

gcctgagaac caacttcctg cgctactgga ccctcaccta tctggcgctg cccacagtga   1560

ccgaccagga ggccacccct gtgcccccca caggggactc cgaggccact cccgtgcccc   1620

ccacgggtga ctccgagacc gcccccgtgc cgcccacggg tgactccggg gcccccccg    1680

tgccgcccac gggtgactcc ggggccccc ccgtgccgcc cacgggtgac tccggggccc    1740

cccccgtgcc gcccacgggt gactccaagg aagctcagat gcctgcagtc attaggtttt   1800

agcgtcccat gagccttggt atcaagaggc cacaagagtg ggaccccagg ggctcccctc   1860

ccatcttgag ctcttcctga ataaagcctc ataccccctga aaaaa                   1905
```

```
<210> SEQ ID NO 8
<211> LENGTH: 1952
<212> TYPE: DNA
<213> ORGANISM: Homo sapiens

<400> SEQUENCE: 8

ttcaaacccc ccttaaacta attgtcacaa agktggataa tattgatgga atycctcaat     60

tggaggatca aagttgagaa aagtaatatt cgacattttt cgattcaacg gagtggccac    120

caagacgatg tcatagaagt ctgaacgagt ctcagttcca atttggtaga ccacttcata    180

catctttgtt ggatttcctg tgtacttggt ctttgttttc tcctcgatgt acattactga    240

gccagatata agattgcttt tggatgcctg cagaagccct gagcaaacaa gtttattgcc    300

accttctact gcccaaaggc cagaatcaga acaggacagt gacaccgccc ccacaaaggc    360

attgatgtcc gtgctttggc cataattgac cctcataaca ggagcaatca tttcattgag    420

gaacttctca gaaaagccgg ccttttgcaa ggtttcaaga agtgttcgat taagcattcc    480

aaggaagtca tctcctccta gagcatgaag taatttttcg acactactga aggcatagtc    540

atgagactgg tagcggtaga tcctcatgaa cttgtctaac acgtcctcta cccacatgtg    600

catacggagg gattgaaatc catagcgcca aactaattta atcacgttaa ttatgaacca    660

gttgctctcc tcaaatacca gagtctctcc attatatatc cccagtaggc cacccagagg    720

ctgatgctca ccatggggcg cctgcaactg gttgtgttgg gcctcacctg ctgctgggca    780

gtggcgagtg ccgcgaagac cccatgctgc actatgtggg cttcgtccct gtcattgatg    840

gagacttcat ccccgctgac ccgatcaacc tgtacgccaa cgccgccgac atcgactata    900

tagcaggcac caacaacatg gacggccaca tcttcgccag catcgacatg cctgccatca    960

acaagggcaa caagaaagtc acggaggagg acttctacaa gctggtcagt gagttcacaa   1020

tcaccaaggg gctcagaggc gccaagacga cctttgatgt ctacaccgag tcctgggccc   1080

aggacccatc ccaggagaat aagaagaaga ctgtggtgga ctttgagacc gatgtcctct   1140
```

-continued

```
tcctggtgcc caccgagatt gccctagccc agcacagagc caatgccaag agtgccaaga   1200

cctacgccta cctgttttcc catccctctc ggatgcccgt ctaccccaaa tgggtggggg   1260

ccgaccatgc agatgacatt cagtacgttt tcgggaagcc cttcgccacc cccacgggct   1320

accggcccca agacaggaca gtctctaagg ccatgatcgc ctactggacc aactttgcca   1380

aaacagggga ccccaacatg ggcgactcgg ctgtgcccac acactgggaa ccctacacta   1440

cggaaaacag cggctacctg gagatcacca agaagatggg cagcagctcc atgaagcgga   1500

gcctgagaac caacttcctg cgctactgga ccctcaccta tctggcgctg cccacagtga   1560

ccgaccagga ggccacccct gtgcccccca caggggactc cgaggccact cccgtgcccc   1620

ccacgggtga ctccgagacc gcccccgtgc cgcccacggg tgactccggg gcccccccg    1680

tgccgcccac gggtgactcc ggggccccc ccgtgccgcc cacgggtgac tccggggccc    1740

cccccgtgcc gcccacgggg tgcccccac gggtgactct gaggctgccc ctgtgccccc    1800

cacagatgac tccaaggaag ctcagatgcc tgcagtcatt aggttttagc gtcccatgag   1860

ccttggtatc aagaggccac aagagtggga ccccaggggc tcccctccca tcttgagctc   1920

ttcctgaata aagcctcata cccctgaaaa aa                                 1952
```

<210> SEQ ID NO 9
<211> LENGTH: 2690
<212> TYPE: DNA
<213> ORGANISM: Homo sapiens

<400> SEQUENCE: 9

```
cttcctcttc tccacgcagg cttcaacagg agatttatgg agaatagcag cataattgct     60

tgctataatg aactgattca aatagaacat ggggaagttc gctcccagtt caaattacgg    120

gcctgtaatt cagtgtttac agcattagat cactgtcatg aagccataga aataacaagc    180

gatgaccacg tgattcagga gtggcagggg gtttactatg ccagacggaa atccggggac    240

agcatccaac agcacgtgaa gatcacccca gtgattggcc aaggagggaa aattaggcat    300

tttgtctcgc tcaagaaact gtgttgtacc actgacaata ataagcagat tcacaagatt    360

catcgtgatt caggagataa ttctcagaca gagcctcatt cattcagata taagaacagg    420

aggaaagagt ccattgacgt gaaatcgata tcatctcgag gcagtgatgc accaagcctg    480

cagaatcgtc gctatccgtc catggcgagg atccactcca tgaccatcga ggctcccatc    540

acaaaggtta taaatataat caatgcagcc caagaaaaca gcccagtcac agtagcggaa    600

gccttggaca gagttctaga gattttacgg accacagaac tgtactcccc tcagctgggt    660

accaaagatg aagatcccca caccagtgat cttgttggag gcctgatgac tgacggcttg    720

agaagactgt caggaaacga gtatgtgttt actaagaatg tgcaccagag tcacagtcac    780

cttgcaatgc caataaccat caatgatgtt ccccccttgta tctctcaatt acttgataat   840

gaggagagtt gggacttcaa catctttgaa ttggaagcca ttacgcataa aaggccattg    900

gtttatctgg gcttaaaggt cttctctcgg tttggagtat gtgagttttt aaactgttct    960

gaaaccactc ttcgggcctg gttccaagtg atcgaagcca actaccactc ttccaatgcc   1020

taccacaact ccacccatgc tgccgacgtc ctgcacgcca ccgctttctt tcttggaaag   1080

gaaagagtaa agggaagcct cgatcagttg gatgaggtgg cagccctcat tgctgccaca   1140

gtccatgacg tggatcaccc gggaaggacc aactctttcc tctgcaatgc aggcagtgag   1200

cttgctgtgc tctacaatga cactgctgtt ctggagagtc accacaccgc cctggccttc   1260

cagctcacgg tcaaggacac caaatgcaac attttcaaga atattgacag gaaccattat   1320
```

-continued

```
cgaacgctgc gccaggctat tattgacatg gttttggcaa cagagatgac aaaacacttt   1380
gaacatgtga ataagtttgt gaacagcatc aacaagccaa tggcagctga gattgaaggc   1440
agcgactgtg aatgcaaccc tgctgggaag aacttccctg aaaaccaaat cctgatcaaa   1500
cgcatgatga ttaagtgtgc tgacgtggcc aacccatgcc gccccttgga cctgtgcatt   1560
gaatgggctg ggaggatctc tgaggagtat tttgcacaga ctgatgaaga gaagagacag   1620
ggactacctg tggtgatgcc agtgtttgac cggaatacct gtagcatccc caagtctcag   1680
atctctttca ttgactactt cataacagac atgtttgatg cttgggatgc ctttgcacat   1740
ctaccagccc tgatgcaaca tttggctgac aactacaaac actggaagac actagatgac   1800
ctaaagtgca aaagtttgag gcttccatct gacagctaaa gccaagccac agagggggcc   1860
tcttgaccga caaaggacac tgtgaatcac agtagcgtaa acaagaggcc ttcctttcta   1920
atgacaatga caggtattgg tgaaggagct aatgtttaat atttgacctt gaatcattca   1980
agtccccaaa tttcattctt agaaagttat gttccatgaa gaaaaatata tgttcttttg   2040
aatacttaat gacagaacaa atacttggca aactcctttg ctctgctgtc atcctgtgta   2100
cccttgtcaa tccatggagc tggttcactg taactagcag gccacaggaa gcaaagcctt   2160
ggtgcctgtg agctcatctc ccaggatggt gactaagtag cttagctagt gatcagctca   2220
tcctttacca taaaagtcat cattgctgtt tagcttgact gttttcctca agaacatcga   2280
tctgaaggat tcataaggag cttatctgaa cagatttatc taagaaaaaa aaaaaacgac   2340
ataaaataag cgaaacaact aggaccaaat tacagataaa ctagttagct tcacagcctc   2400
tatggctaca tggttcttct ggccgatggt atgacaccta agttagaaca cagccttggc   2460
tggtgggtgc cctctctaga ctggtatcag cagcctgtgt aaccccttc ctgtaaaagg    2520
ggttcatctt aacaaagtca tccatgatga gggaaaaagt ggcatttcat ttttggggaa   2580
tccatgagct tcctttattt ctggctcaca gaggcagcca cgaggcacta caccaagtat   2640
tatataaaag ccattaaatt tgaatgccct tggacaagct tttcttaaaa              2690
```

<210> SEQ ID NO 10
<211> LENGTH: 1502
<212> TYPE: DNA
<213> ORGANISM: Homo sapiens

<400> SEQUENCE: 10

```
ccttggagac tagaaagaaa ctgctagatg gctgtaacac agttcatcca tttccgtgaa     60
gagatcatgg ggaatatgtt cttcatcatc atcttcagta ccaaggataa actgtgttac    120
agagatggag aagaatatga atggaaagaa actgctagat ggctgaaatt tgaagaggat    180
gttgaagatg gcggtgaccg atggagtaaa ccttatgtgg caactctctc tttgcacagt    240
ctttttgaac taaggagttg catcctcaat ggaacagtca tgctggatat gagagcaagc    300
actctagatg aaatagcaga tatggtatta gacaacatga tagcttctgg ccaattagac    360
gagtccatac gagagaatgt cagagaagct cttctgaaga gacatcatca tcagaatgag    420
aaaagattca ccagtcggat tcctcttgtt cgatcttttg cagatatagg caagaaacat    480
tctgaccctc acttgcttga aaggaatggt attttggcct ctccccagtc tgctcctgga    540
aacttggaca atagtaaaag tggagaaatt aaaggtaatg gaagtggtgg aagcagagaa    600
aatagtactg ttgacttcag caaggttgat atgaatttca tgagaaaaat tcctacgggt    660
gctgaggcat ccaacgtcct ggtgggcgaa gtagactttt tggaaaggcc aataattgca    720
```

-continued

```
tttgtgagac tggctcctgc tgtcctcctt acagggttga ctgaggtccc tgttccaacc    780

aggtttttgt ttttgttatt gggtccagcg ggcaaggcac cacagtacca tgaaattgga    840

cgatcaatag ccactctcat gacagatgag attttccatg atgtagctta taaagcaaaa    900

gacagaaatg acctcttatc tggaattgat gaatttttag atcaagtaac tgtcctacct    960

ccaggagagt gggatccttc tatacgcata gaaccaccaa aaagtgtccc ttctcaggaa   1020

aagagaaaga ttcctgtgtt tcacaatgga tctacccca cactgggtga gactcctaaa   1080

gaggccgctc atcatgctgg gcctgagcta cagaggactg gacggctttt tggtgggttg   1140

atacttgaca tcaaaaggaa agcacctttt ttcttgagtg acttcaagga tgcattaagc   1200

ctgcagtgcc tggcctcgat tcttttccta tactgtgcct gtatgtctcc tgtaatcact   1260

tttggagggc tgcttggaga agctacagaa ggcagaatag tgagtacaaa gattggtagt   1320

ggccaggctt ttagctcttc agaggcaagt gtctgtatgc atttgtctca ctattcatac   1380

ttttatttga agagtctacc cacagcatga ttaacgtgac ccaaagcaga ctttccccaa   1440

aggtaattgc tgtggaaaac atggggaagc catttgaaca gaagatgcac agttgaggta   1500

aa                                                                  1502
```

<210> SEQ ID NO 11
<211> LENGTH: 594
<212> TYPE: DNA
<213> ORGANISM: Homo sapiens

<400> SEQUENCE: 11

```
ccttggagac tagaaagaaa ctgctagatg gctgtaacac agttcatcca tttccgtgaa     60

gagatcatgg ggaatatgtt cttcatcatc atcttcagta ccaaggataa actgtgttac    120

agagatggag aagaatatga atggaaagaa actgctagat ggctgaaatt tgaagaggat    180

gttgaagatg gcggtgaccg atggagtaaa ccttatgtgg caactctctc tttgcacagt    240

ctttttgaac taaggagttg catcctcaat ggaacagtca tgctggatat gagagcaagc    300

actctagatg aaatagcaga tatggtatta gacaacatga tagcttctgg ccaattagac    360

gagtccatac gagagaatgt cagagaagct cttctgaaga gacatcatca tcagaatgag    420

aaaagattca ccagtcggat tcctcttgtt cgatcttttg cagatatagg caagaaacat    480

tctgaccctc acttgcttga aaggaatggt gagataagtt gtggcatcca atttttgcta    540

acacttctac tgtaacagct ttccagtatg ttacgattaa catttgggga tatt          594
```

<210> SEQ ID NO 12
<211> LENGTH: 3166
<212> TYPE: DNA
<213> ORGANISM: Homo sapiens

<400> SEQUENCE: 12

```
aggaaggcta ttagtatata atagtagcct ctttataaat aatagtattt attaaaataa     60

ggcggtcttt gtaattcatt tttattggtt ggataatgtt catttctgca ttgattattt    120

gtgacagaat aaaactttct agagctattt aaggttctaa tttttgtcat aaggtttcac    180

tcacagttta ttcctatatt atggtcatct gagtgtttag taatttattt ttttttttcat   240

tgaatagata tggtattaga caacatgata gcttctggcc aattagacga gtccatacga    300

gagaatgtca gagaagctct tctgaagaga catcatcatc agaatgagaa aagattcacc    360

agtcggattc ctcttgttcg atcttttgca gatataggca agaaacattc tgaccctcac    420

ttgcttgaaa ggaatggtat tttggcctct ccccagtctg ctcctggaaa cttggacaat    480
```

-continued

```
agtaaaagtg gagaaattaa aggtaatgga agtggtggaa gcagagaaaa tagtactgtt    540
gacttcagca aggttgatat gaatttcatg agaaaaattc ctacgggtgc tgaggcatcc    600
aacgtcctgg tgggcgaagt agactttttg gaaaggccaa taattgcatt tgtgagactg    660
gctcctgctg tcctccttac agggttgact gaggtccctg ttccaaccag gtttttgttt    720
ttgttattgg gtccagcggg caaggcacca cagtaccatg aaattggacg atcaatagcc    780
actctcatga cagatgagat tttccatgat gtagcttata aagcaaaaga cagaaatgac    840
ctcttatctg gaattgatga atttttagat caagtaactg tcctacctcc aggagagtgg    900
gatccttcta tacgcataga accaccaaaa agtgtccctt ctcaggaaaa gagaaagatt    960
cctgtgtttc acaatggatc tacccccaca ctgggtgaga ctcctaaaga ggccgctcat   1020
catgctgggc ctgagctaca gaggactgga cggctttttg gtgggttgat acttgacatc   1080
aaaaggaaag cacctttttt cttgagtgac ttcaaggatg cattaagcct gcagtgcctg   1140
gcctcgattc ttttcctata ctgtgcctgt atgtctcctg taatcacttt tggagggctg   1200
cttggagaag ctacagaagg cagaataagt gcaatagagt ctctttttgg agcatcatta   1260
actgggattg cctattcatt gtttgctggg caacctctaa caatattggg gagcacaggt   1320
ccagttctag tgtttgaaaa aattttatat aaattctgca gagattatca actttcttat   1380
ctgtctttaa gaaccagtat tggtctgtgg acttcttttt tgtgcattgt tttggttgca   1440
acagatgcaa gcagccttgt gtgttatatt actcgattta cagaagaggc ttttgcagcc   1500
cttatttgca tcatattcat ctacgaggct ttggagaagc tctttgattt aggagaaaca   1560
tatgcattta atatgcacaa caacttagat aaactgacca gctactcatg tgtatgtact   1620
gaacctccaa accccagcaa tgaaactcta gcacaatgga agaaagataa tataacagca   1680
cacaatattt cctggagaaa tcttactgtt tctgaatgta aaaaacttcg tggtgtattc   1740
ttggggtcag cttgtggtca tcatggacct tatattccag atgtgctctt ttggtgtgtc   1800
atcttgtttt tcacaacatt ttttctgtct tcattcctca agcaatttaa gaccaagcgt   1860
tactttccta ccaaggtgcg atcgacaatc agtgattttg ctgtatttct cacaatagta   1920
ataatggtta caattgacta ccttgtagga gttccatctc ctaaacttca tgttcctgaa   1980
aaatttgagc ctactcatcc agagagaggg tggatcataa gcccactggg agataatcct   2040
tggtggacct tattaatagc tgctattcct gctttgcttt gtaccattct catctttatg   2100
gatcaacaaa tcacagctgt aattataaac agaaaggaac acaaattgaa gaaaggagct   2160
ggctatcacc ttgatttgct catggttggc gttatgttgg gagtttgctc tgtcatggga   2220
cttccatggt ttgtggctgc aacagtgttg tcaataagtc atgtcaacag cttaaaagtt   2280
gaatctgaat gttctgctcc aggggaacaa cccaagtttt tgggaattcg tgaacagcgg   2340
gttacagggc taatgatttt tattctaatg ggcctctctg tgttcatgac ttcagtccta   2400
aagtttattc caatgcctgt tctgtatggt gttttccttt atatgggagt ttcctcatta   2460
aaaggaatcc agttatttga ccggataaaa ttatttggaa tgcctgctaa gcatcagcct   2520
gatttgatat acctccggta tgtgccgctc tggaaggtcc atattttcac agtcattcag   2580
cttacttgct tggtcctttt atgggtgata aaagtttcag ctgctgcagt ggtttttccc   2640
atgatggttc ttgcattagt gtttgtgcgc aaactcatgg acctgtgttt cacgaagaga   2700
gaacttagtt ggcttgatga tcttatgcca gaaagtaaga aaaagaaaga agatgacaaa   2760
aagaaaaaag agaaagagga agctgaacgg atgcttcaag acgatgatga tactgtgcac   2820
```

-continued

```
cttccatttg aagggggaag tctcttgcaa attccagtca aggccctaaa atatagtggt   2880

gatccctcaa ttggtaacat atcagatgaa atggccaaaa ctgcacagtg gaaggcactt   2940

tccatgaata ctgagaatgc caaagtaacc agatctaaca tgagtcctga taaacctgtg   3000

agtgtgaaat aagtttgaga tgaaccaaga aagaaatacg tggagctgaa acttcatata   3060

gaatggaacc aagaggcata tacatataga tatatacata tgtaagggtg cgatcatggc   3120

actatatata gaatatggag gcaaggcggg taaggggga ctaacc                 3166
```

<210> SEQ ID NO 13
<211> LENGTH: 1430
<212> TYPE: DNA
<213> ORGANISM: Homo sapiens

<400> SEQUENCE: 13

```
aggaaggcta ttagtatata atagtagcct ctttataaat aatagtattt attaaaataa     60

ggcggtcttt gtaattcatt tttattggtt ggataatgtt catttctgca ttgattattt    120

gtgacagaat aaaactttct agagctattt aaggttctaa tttttgtcat aaggtttcac    180

tcacagttta ttcctatatt atggtcatct gagtgtttag taatttattt ttttttcat    240

tgaatagata tggtattaga caacatgata gcttctggcc aattagacga gtccatacga    300

gagaatgtca gagaagctct tctgaagaga catcatcatc agaatgagaa aagattcacc    360

agtcggattc ctcttgttcg atcttttgca gatataggca agaaacattc tgaccctcac    420

ttgcttgaaa ggaatggtat tttggcctct ccccagtctg ctcctggaaa cttggacaat    480

agtaaaagtg gagaaattaa aggtaatgga agtggtggaa gcagagaaaa tagtactgtt    540

gacttcagca aggttgatat gaatttcatg agaaaaattc ctacgggtgc tgaggcatcc    600

aacgtcctgg tgggcgaagt agactttttg gaaaggccaa taattgcatt tgtgagactg    660

gctcctgctg tcctccttac agggttgact gaggtccctg ttccaaccag gtttttgttt    720

ttgttattgg gtccagcggg caaggcacca cagtaccatg aaattggacg atcaatagcc    780

actctcatga cagatgagat tttccatgat gtagcttata aagcaaaaga cagaaatgac    840

ctcttatctg gaattgatga atttttagat caagtaactg tcctacctcc aggagagtgg    900

gatccttcta tacgcataga accaccaaaa agtgtccctt ctcaggaaaa gagaaagatt    960

cctgtgtttc acaatggatc tacccccaca ctgggtgaga ctcctaaaga ggccgctcat   1020

catgctgggc ctgagctaca gaggactgga cggctttttg gtgggttgat acttgacatc   1080

aaaaggaaag caccttttt cttgagtgac ttcaaggatg cattaagcct gcagtgcctg   1140

gcctcgattc ttttcctata ctgtgcctgt atgtctcctg taatcacttt tggagggctg   1200

cttggagaag ctacagaagg cagaatagtg agtacaaaga ttggtagtgg ccaggctttt   1260

agctcttcag aggcaagtgt ctgtatgcat ttgtctcact attcatactt ttatttgaag   1320

agtctaccca cagcatgatt aacgtgaccc aaagcagact ttccccaaag gtaattgctg   1380

tggaaaacat ggggaagcca tttgaacaga agatgcacag ttgaggtaaa              1430
```

<210> SEQ ID NO 14
<211> LENGTH: 678
<212> TYPE: DNA
<213> ORGANISM: Homo sapiens

<400> SEQUENCE: 14

```
tttcctcact gactataaaa gaatagagaa ggaagggctt cagtgaccgg ctgcctggct     60

gacttacagc agtcagactc tgacaggatc atggctatga tggaggtcca gggggaccc    120
```

-continued

```
agcctgggac agacctgcgt gctgatcgtg atcttcacag tgctcctgca gtctctctgt    180

gtggctgtaa cttacgtgta ctttaccaac gagctgaagc agatgcagga caagtactcc    240

aaaagtggca ttgcttgttt cttaaaagaa gatgacagtt attgggaccc caatgacgaa    300

gagagtatga acagcccctg ctggcaagtc aagtggcaac tccgtcagct cgttagaaag    360

atgattttga gaacctctga ggaaaccatt tctacagttc aagaaaagca acaaaatatt    420

tctcccctag tgagagaaag aggtcctcag agagtagcag ctcacataac tgggaccaga    480

ggaagaagca acacattgtc ttctccaaac tccaggagaa tcgtttgaac ccgggaggca    540

gaggttgcag tgtggtgaga tcatgccact acactccagc ctggcgacag agcgagactt    600

ggtttcaaaa aaaaaaaaaa aaaaacttca gtaagtacgt gttatttttt tcaataaaat    660

tctattacag tatgtcga                                                  678
```

<210> SEQ ID NO 15
<211> LENGTH: 1711
<212> TYPE: DNA
<213> ORGANISM: Homo sapiens

<400> SEQUENCE: 15

```
tttcctcact gactataaaa gaatagagaa ggaagggctt cagtgaccgg ctgcctggct     60

gacttacagc agtcagactc tgacaggatc atggctatga tggaggtcca ggggggaccc    120

agcctgggac agacctgcgt gctgatcgtg atcttcacag tgctcctgca gtctctctgt    180

gtggctgtaa cttacgtgta ctttaccaac gagctgaagc agatgcagga caagtactcc    240

aaaagtggca ttgcttgttt cttaaaagaa gatgacagtt attgggaccc caatgacgaa    300

gagagtatga acagcccctg ctggcaagtc aagtggcaac tccgtcagct cgttagaaag    360

aaaagcaaca aaatatttct cccctagtga gagaaagagg tcctcagaga gtagcagctc    420

acataactgg gaccagagga agaagcaaca cattgtcttc tccaaactcc aagaatgaaa    480

aggctctggg ccgcaaaata aactcctggg aatcatcaag gagtgggcat tcattcctga    540

gcaacttgca cttgaggaat ggtgaactgg tcatccatga aaaagggttt tactacatct    600

attcccaaac atactttcga tttcaggagg aaataaaaga aaacacaaag aacgacaaac    660

aaatggtcca atatatttac aaatacacaa gttatcctga ccctatattg ttgatgaaaa    720

gtgctagaaa tagttgttgg tctaaagatg cagaatatgg actctattcc atctatcaag    780

ggggaatatt tgagcttaag gaaaatgaca gaatttttgt ttctgtaaca aatgagcact    840

tgatagacat ggaccatgaa gccagttttt tcggggcctt tttagttggc taactgacct    900

ggaaagaaaa agcaataacc tcaaagtgac tattcagttt tcaggatgat acactatgaa    960

gatgtttcaa aaatctgacc aaaaacaaac aaacagaaaa cagaaaacaa aaaaacctct   1020

atgcaatctg agtagagcag ccacaaccaa aaaattctac aacacacact gttctgaaag   1080

tgactcactt atcccaagag aatgaaattg ctgaaagatc tttcaggact ctacctcata   1140

tcagtttgct agcagaaatc tagaagactg tcagcttcca aacattaatg caatggttaa   1200

catcttctgt ctttataatc tactccttgt aaagactgta gaagaaagcg caacaatcca   1260

tctctcaagt agtgtatcac agtagtagcc tccaggtttc cttaagggac aacatcctta   1320

agtcaaaaga gagaagaggc accactaaaa gatcgcagtt tgcctggtgc agtggctcac   1380

acctgtaatc ccaacatttt gggaacccaa ggtgggtaga tcacgagatc aagagatcaa   1440

gaccatagtg accaacatag tgaaacccca tctctactga aagtgcaaaa attagctggg   1500
```

-continued

```
tgtgttggca catgcctgta gtcccagcta cttgagaggc tgaggcagga gaatcgtttg   1560

aacccgggag gcagaggttg cagtgtggtg agatcatgcc actacactcc agcctggcga   1620

cagagcgaga cttggtttca aaaaaaaaaa aaaaaaaact tcagtaagta cgtgttattt   1680

ttttcaataa aattctatta cagtatgtcg a                                  1711
```

<210> SEQ ID NO 16
<211> LENGTH: 635
<212> TYPE: DNA
<213> ORGANISM: Homo sapiens

<400> SEQUENCE: 16

```
tttcctcact gactataaaa gaatagagaa ggaagggctt cagtgaccgg ctgcctggct     60

gacttacagc agtcagactc tgacaggatc atggctatga tggaggtcca gggggggaccc   120

agcctgggac agacctgcgt gctgatcgtg atcttcacag tgctcctgca gtctctctgt    180

gtggctgtaa cttacgtgta ctttaccaac gagctgaagc agatgcagga caagtactcc    240

aaaagtggca ttgcttgttt cttaaaagaa gatgacagtt attgggaccc caatgacgaa    300

gagagtatga acagcccctg ctggcaagtc aagtggcaac tccgtcagct cgttagaaag    360

aaaagcaaca aaatatttct cccctagtga gagaaagagg tcctcagaga gtagcagctc    420

acataactgg gaccagagga agaagcaaca cattgtcttc tccaaactcc aggagaatcg    480

tttgaacccg ggaggcagag gttgcagtgt ggtgagatca tgccactaca ctccagcctg    540

gcgacagagc gagacttggt ttcaaaaaaa aaaaaaaaaa aacttcagta agtacgtgtt    600

atttttttca ataaaattct attacagtat gtcga                               635
```

<210> SEQ ID NO 17
<211> LENGTH: 814
<212> TYPE: DNA
<213> ORGANISM: Homo sapiens

<400> SEQUENCE: 17

```
tttcctcact gactataaaa gaatagagaa ggaagggctt cagtgaccgg ctgcctggct     60

gacttacagc agtcagactc tgacaggatc atggctatga tggaggtcca gggggggaccc   120

agcctgggac agacctgcgt gctgatcgtg atcttcacag tgctcctgca gtctctctgt    180

gtggctgtaa cttacgtgta ctttaccaac gagctgaagc agatgcagga caagtactcc    240

aaaagtggca ttgcttgttt cttaaaagaa gatgacagtt attgggaccc caatgacgaa    300

gagagtatga acagcccctg ctggcaagtc aagtggcaac tccgtcagct cgttagaaag    360

gtaggtaacc tcaccaggtg acctcaccag caggcggaga aggccagaag aattccttaa    420

agcaaaggaa tctttaagat aatcaagtct agactcttca ttttacaaat aagaaaactt    480

aggcccagag tatttaagta attttcccca aattcataga actaggaaaa tggggcatag    540

cagcaaaggg caggacctgg ccgactcctg gtctagagtt cattcctctg ccccggacag    600

cctccacatc tagtctaacc ttttgatctc acattatgga aactgaggca ggagaatcgt    660

ttgaacccgg gaggcagagg ttgcagtgtg gtgagatcat gccactacac tccagcctgg    720

cgacagagcg agacttggtt tcaaaaaaaa aaaaaaaaaa acttcagtaa gtacgtgtta    780

tttttttcaa taaaattcta ttacagtatg tcga                                814
```

<210> SEQ ID NO 18
<211> LENGTH: 1868
<212> TYPE: DNA
<213> ORGANISM: Homo sapiens

<400> SEQUENCE: 18

```
gaagtttagt gacttgctga aatgggctag ggaatctaat ttcaaatggg caaaaagata     60
aacaaactat tttgctttaa ttttctagtt cagtgtttta ggggtaaatc aaaaccatcc    120
aaatgtcaga tcagaaagaa agttaaaaat catatagaaa gacttctgga tactgaagat    180
gagctcagtg acattcagac tgactcagtc ccatctgaag tccgggactg gttggcttct    240
acctttacac ggaaaatggg gatgacaaaa aagaaacctg aggaaaaacc aaaatttcgg    300
agcattgtgc atgctgttca agctggaatt tttgtggaaa gaatgtaccg aaaaacatat    360
catatggttg gtttggcata tccagcagct gtcatcgtaa cattaaagga tgttgataaa    420
tggtctttcg atgtatttgc cctaaatgaa gcaagtggag agcatagtct gaagtttatg    480
atttatgaac tgtttaccag atatgatctt atcaaccgtt tcaagattcc tgtttcttgc    540
ctaatcacct ttgcagaagc tttagaagtt ggttacagca agtacaaaaa tccatatcac    600
aatttgattc atgcagctga tgtcactcaa actgtgcatt acataatgct tcatacaggt    660
atcatgcact ggctcactga actggaaatt ttagcaatgg tctttgctgc tgccattcat    720
gattatgagc atacagggac aacaaacaac tttcacattc agacaaggtc agatgttgcc    780
attttgtata atgatcgctc tgtccttgag aatcaccacg tgagtgcagc ttatcgactt    840
atgcaagaag aagaaatgaa tatcttgata aatttatcca aagatgactg gagggatctt    900
cggaacctag tgattgaaat ggttttatct acagacatgt caggtcactt ccagcaaatt    960
aaaaatataa gaaacagttt gcagcagcct gaagggattg acagagccaa aaccatgtcc   1020
ctgattctcc acgcagcaga catcagccac ccagccaaat cctggaagct gcattatcgg   1080
tggaccatgg ccctaatgga ggagtttttc ctgcagggag ataaagaagc tgaattaggg   1140
cttccatttt ccccactttg tgatcggaag tcaaccatgg tggcccagtc acaaataggt   1200
ttcatcgatt tcatagtaga gccaacattt tctcttctga cagactcaac agagaaaatt   1260
gttattcctc ttatagagga agcctcaaaa gccgaaactt cttcctatgt ggcaagcagc   1320
tcaaccacca ttgtggggtt acacattgct gatgcactaa gacgatcaaa tacaaaaggc   1380
tccatgagtg atgggtccta ttccccagac tactcccttg cagcagtgga cctgaagagt   1440
ttcaagaaca acctggtgga catcattcag cagaacaaag agaggtggaa agagttagct   1500
gcacaagaag caagaaccag ttcacagaag tgtgagttta ttcatcagta aacaccttta   1560
agtaaaacct cgtgcatggt ggcagctcta atttgaccaa aagacttgga gattttgatt   1620
atgcttgctg gaaatctacc ctgtcctgtg tgagacagga aatctatttt tgcagattgc   1680
tcaataagca tcatgagcca cataaataac agctgtaaac tccttaattc accgggctca   1740
actgctaccg aacagattca tctagtggct acatcagcac cttgtgcttt cagatatctg   1800
tttcaatggc attttgtggc atttgtcttt accgagtgcc aataaatttt ctttgagcag   1860
ctaaaaaa                                                            1868
```

<210> SEQ ID NO 19
<211> LENGTH: 1140
<212> TYPE: DNA
<213> ORGANISM: Homo sapiens

<400> SEQUENCE: 19

```
ggaaacatga tccagctgaa ggactgattg caggaaaact tggcagctcc ccaaccttgg     60
tggcccaggg agtgtgaggc tgcagcctca gaaggtgtga gcagtggcca cgagaggcag    120
```

-continued

```
gctggctggg acatgaggtt ggcagagggc aggcaagctg gcccttggtg ggcctcgccc    180

tgagcactcg gaggcactcc tatgcttgga aagctcgcta tgctgctgtg ggtccagcag    240

gcgctgctcg ccttgctcct ccccacactc ctggcacagg gagaagccag gaggagccga    300

aacaccacca ggcccgctct gctgaggctg tcggattacc ttttgaccaa ctacaggaag    360

ggtgtgcgcc ccgtgaggga ctggaggaag ccaaccaccg tatccattga cgtcattgtc    420

tatgccatcc tcaacgtgga tgagaagaat caggtgctga ccacctacat ctggtaccgg    480

cagtactgga ctgatgagtt tctccagtgg aaccctgagg actttgacaa catcaccaag    540

ttgtccatcc ccacggacag catctgggtc ccggacattc tcatcaatga gttcgtggat    600

gtggggaagt ctccaaatat cccgtacgtg tatattcggc atcaaggcga agttcagaac    660

tacaagcccc ttcaggtggt gactgcctgt agcctcgaca tctacaactt ccccttcgat    720

gtccagaact gctcgctgac cttcaccagt tggctgcaca ccacccagta cttcacatct    780

tctttgtgtc gtttgccaga taaagtgtaa atccgacagc agctcaccat ggctttaaaa    840

catgctctct tagatcagga gaaactcggg cactccctaa gtccactcta gttgtggact    900

tttccccatt gaccctcacc tgaataaggg actttggaat tctgcttctc tttcacaact    960

ttgcttttag gttgaaggca aaaccaactc tctactacac aggcctgata actctgtacg   1020

aggcttctct aacccctagt gtcttttttt tcttcacctc acttgtggca gcttccctga   1080

acactcatcc cccatcagat gatgggagtg ggaagaataa aatgcagtga aacccatcaa   1140
```

```
<210> SEQ ID NO 20
<211> LENGTH: 963
<212> TYPE: DNA
<213> ORGANISM: Homo sapiens

<400> SEQUENCE: 20

aattccgggt cactccccct ctctgagctt ggaaagctcg ctatgctgct gtgggtccag     60

caggcgctgc tcgccttgct cctccccaca ctcctggcac agggagaagc caggaggagc    120

cgaaacacca ccaggcccgc tctgctgagg ctgtcggatt accttttgac caactacagg    180

aagggtgtgc gccccgtgag ggactggagg aagccaacca ccgtatccat tgacgtcatt    240

gtctatgcca tcctcaacgt ggatgagaag aatcaggtgc tgaccaccta catctggtac    300

cggcagtact ggactgatga gtttctccag tggaaccctg aggactttga caacatcacc    360

aagttgtcca tccccacgga cagcatctgg gtcccggaca ttctcatcaa tgagttcgtg    420

gatgtgggga agtctccaaa tatcccgtac gtgtatattc ggcatcaagg cgaagttcag    480

aactacaagc cccttcaggt ggtgactgcc tgtagcctcg acatctacaa cttccccttc    540

gatgtccaga actgctcgct gaccttcacc agttggctgc acaccaccca gtacttcaca    600

tcttctttgt gtcgtttgcc agataaagtg taaatccgac agcagctcac catggcttta    660

aaacatgctc tcttagatca ggagaaactc gggcactccc taagtccact ctagttgtgg    720

acttttcccc attgaccctc acctgaataa gggactttgg aattctgctt ctctttcaca    780

actttgcttt taggttgaag gcaaaaccaa ctctctacta cacaggcctg ataactctgt    840

acgaggcttc tctaacccct agtgtctttt ttttcttcac ctcacttgtg gcagcttccc    900

tgaacactca tcccccatca gatgatggga gtgggaagaa taaaatgcag tgaaacccat    960

caa                                                                  963

<210> SEQ ID NO 21
<211> LENGTH: 1444
```

-continued

<212> TYPE: DNA
<213> ORGANISM: Homo sapiens

<400> SEQUENCE: 21

```
gcctcgctcg ggcgcccagt ggtcctgccg cctggtctca cctcgccatg gttcgtctgc     60
ctctgcagtg cgtcctctgg ggctgcttgc tgaccgctgt ccatccagaa ccacccactg    120
catgcagaga aaaacagtac ctaataaaca gtcagtgctg ttctttgtgc cagccaggac    180
agaaactggt gagtgactgc acagagttca ctgaaacgga atgccttcct tgcggtgaaa    240
gcgaattcct agacacctgg aacagagaga cacactgcca ccagcacaaa tactgcgacc    300
ccaacctagg gcttcgggtc cagcagaagg gcacctcaga aacagacacc atctgcacct    360
gtgaagaagg ctggcactgt acgagtgagg cctgtgagag ctgtgtcctg caccgctcat    420
gctcgcccgg ctttggggtc aagcagattg ctacaggggt ttctgatacc atctgcgagc    480
cctgcccagt cggcttcttc tccaatgtgt catctgcttt cgaaaaatgt cacccttgga    540
caaggtcccc aggatcggct gagagccctg gtggtgatcc ccatcatctt cgggatcctg    600
tttgccatcc tcttggtgct ggtctttatc aaaaaggtgg ccaagaagcc aaccaataag    660
gcccccacc ccaagcagga accccaggag atcaattttc ccgacgatct tcctggctcc    720
aacactgctg ctccagtgca ggagacttta catggatgcc aaccggtcac ccaggaggat    780
ggcaaagaga gtcgcatctc agtgcaggag agacagtgag gctgcaccca cccaggagtg    840
tggccacgtg ggcaaacagg cagttggcca gagagcctgg tgctgctgct gctgtggcgt    900
gagggtgagg ggctggcact gactgggcat agctccccgc ttctgcctgc acccctgcag    960
tttgagacag gagacctggc actggatgca gaaacagttc accttgaaga acctctcact   1020
tcaccctgga gcccatccag tctcccaact tgtattaaag acagaggcag aagtttggtg   1080
gtggtggtgt tggggtatgg tttagtaata tccaccagac cttccgatcc agcagtttgg   1140
tgcccagaga ggcatcatgg tggcttccct gcgcccagga agccatatac acagatgccc   1200
attgcagcat tgtttgtgat agtgaacaac tggaagctgc ttaactgtcc atcagcagga   1260
gactggctaa ataaaattag aatatattta tacaacagaa tctcaaaaac actgttgagt   1320
aaggaaaaaa aggcatgctg ctgaatgatg ggtatggaac tttttaaaaa aagtacatgc   1380
ttttatgtat gtatattgcc tatggatata tgtataaata caatatgcat catatattga   1440
tata                                                                 1444
```

<210> SEQ ID NO 22
<211> LENGTH: 1264
<212> TYPE: DNA
<213> ORGANISM: Homo sapiens

<400> SEQUENCE: 22

```
aaaaggaacc ccaaagctga ctgtgtacac aaatgggctt tccataagtt cattacattt     60
ccttttccaa gtcaggaaaa ctcaacagtg gtagctactg tggtctgtcc ttgaagattc    120
tgagcagtgc aaatgtaata tcctgcatca atcgtctcga agtcttccac tgtaatgaca    180
ctctgggaga ttctcgtggt gtgtcccagt cctctgtgga tcaacctcca agtgtcttgg    240
atcgtcacag gcctttcatc cttctgccct gggaagatcc aggtgaactc cacctccaaa    300
acgggctcca cctacatctt ttttacagag aaaggagaac tctttgtacc ttctcccagc    360
tacttcgatg ttgtctactt gaacccggac agacaggctg tggttccttg tcgggtgacc    420
gtgctgtcgg ccaaagtcac gctccacagg gaattcccag ccaaggagat cccagccaat    480
```

-continued

```
ggaacggaca ttgtttatga catgaagcgg ggctttgtgt atctgcaacc tcattccgag    540
caccagggtg tggtttactg cagggcggag gccgggggca gatctcagat ctccgtcaag    600
taccagctgc tctacgtggc ggttcccagt ggccctccct caacaaccat cttggcttct    660
tcaaacaaag tgaaaagtgg ggacgacatc agtgtgctct gcactgtcct gggggagccc    720
gatgtggagg tggagttcac ctggatcttc ccagggcaga aggatgaaag gcctgtgacg    780
atccaagaca cttggaggtt gatccacaga ggactgggac acaccacgag aatctcccag    840
agtgtcatta cagtggaaga cttcgagacg attgatgcag gatattacat ttgcactgct    900
cagaatcttc aaggacagac cacagtagct accactgttg agttttcctg acttggaaaa    960
ggaaatgtaa tgaacttatg gaaagcccat ttgtgtacac agtcagcttt ggggttcctt   1020
ttattagtgc tttgccagag gctgatgtca agcaccacac cccaacccca gcgtctcgtg   1080
agtccgaccc agacatccaa actaaaagga agtcatccag tctattcaca gaagtgttaa   1140
cttttctaac agaaagcatg attttgattg cttacctaca tacgtgttcc tagtttttat   1200
acatgtgtaa acaattttat ataatcaatc atttctatta aatgagcacg tttttgtaaa   1260
aaat                                                                1264

<210> SEQ ID NO 23
<211> LENGTH: 883
<212> TYPE: DNA
<213> ORGANISM: Homo sapiens

<400> SEQUENCE: 23

attgccatcc catggtcagc gccttgacca aaggtgtgga agtcgtggta acaatatgga     60
gttccaagtg cttttgagtc aaatgccccg gnaccngctg tcaaacggga tttgggtcca    120
ggcacttggt ctcaaaaaag tacttgtttg aatacactgt tgttaatgtt cacctctccc    180
aacaccatca cctccttgcc cttgatgtct gtggcggtgg tcttatcccc aacccacacg    240
ctgactccgt tcaccccgtg tgctgtttag cacccagcct ccccgtgaag ctgcagacac    300
tcaggatctg gacttcgagg tcggtggtgc tgccccccttc aacaggactc acaggagcaa    360
gcggtcatca tcccatccca tcttccacag gggcgaattc tcggtgtgtg acagtgtcag    420
cgtgtgggtt ggggataaga ccaccgccac agacatcaag ggcaaggagg tgatggtgtt    480
gggagaggtg aacattaaca acagtgtatt caaacaagta ctttttttgag accaagtgcc    540
gggacccaaa tcccgttgac agcgggtgcc ggggcattga ctcaaagcac tggaactcat    600
attgtaccac gactcacacc tttgtcaagg cgctgaccat ggatggcaag caggctgcct    660
ggcggtttat ccggatagat acggcctgtg tgtgtgtgct cagcaggaag gctgtgagaa    720
gagcctgacc tgccgacacg ctccctcccc ctgccccttc tacactctcc tgggcccctc    780
cctacctcaa cctgtaaatt attttaaatt ataaggactg catggtaatt tatagtttat    840
acagttttaa agaatcatta tttattaaat ttttggaagc aaa                     883

<210> SEQ ID NO 24
<211> LENGTH: 1584
<212> TYPE: DNA
<213> ORGANISM: Homo sapiens

<400> SEQUENCE: 24

tccacccctc ctctcatggg tactgtnggg gaggatgggt gccacaggac cacacaggtg     60
gctgtctgag agggtagtgc ctgggaactt tctggaagcc tgtttgggga agcagatggg    120
gtgaaggatt cagttagtgt atgtggggtc gtgacaccat ctacccactg tctctctcct    180
```

```
gccttcatca tcctctagaa atacagcaac aattcctggc gatacctcag caaccggctg    240

ctggcaccca gcgactcgcc agagtggtta tcttttgatg tcaccggagt tgtgcggcag    300

tggttgagcc gtggaggggga aattgagggc tttcgcctta gcgcccactg ctcctgtgac    360

agcagggata acacactgca agtggacatc aacgggttca ctaccggccg ccgaggtgac    420

ctggccacca ttcatggcat gaaccggcct ttcctgcttc tcatggccac cccgctggag    480

agggcccagc atctgcaaag ctcccggcac cgccgagccc tggacaccaa ctattgcttc    540

agctccacgg agaagaactg ctgcgtgcgg cagctgtaca ttgacttccg caaggacctc    600

ggctggaagt ggatccacga gcccaagggc taccatgcca acttctgcct cgggccctgc    660

ccctacattt ggagcctgga cacgcagtac agcaaggtcc tggccctgta caaccagcat    720

aacccgggcg cctcggcggc gccgtgctgc gtgccgcagg cgctggagcc gctgcccatc    780

gtgtactacg tgggccgcaa gcccaaggtg gagcagctgt ccaacatgat cgtgcgctcc    840

tgcaagtgca gctgaggtcc cgccccgccc cgccccgccc cggcaggccc ggccccaccc    900

cgccccgccc ccgctgcctt gcccatgggg gctgtattta aggacacccg tgccccaagc    960

ccacctgggg ccccattaaa gatggagaga ggactgcgga tctctgtgtc attgggcgcc   1020

tgcctggggt ctccatccct gacgttcccc cactcccact ccctctctct ccctctctgc   1080

ctcctcctgc ctgtctgcac tattcctttg cccggcatca aggcacaggg gaccagtggg   1140

gaacactact gtagttagat ctatttattg agcaccttgg gcactgttga agtgccttac   1200

attaatgaac tcattcagtc accatagcaa cactctgaga tggcagggac tctgataaca   1260

cccattttaa aggttgagga aacaagccca gagaggttaa gggaggagtt cctgcccacc   1320

aggaacctgc tttagtgggg gatagtgaag aagacaataa aagatagtag ttcaggccag   1380

gcggggtgct cacgcctgta atcctagcac ttttgggagg cagagatggg aggatacttg   1440

aatccaggca tttgagacca gcctgggtaa catagtgaga ccctatctct acaaaacact   1500

tttaaaaaat gtacacctgt ggtcccagct actctggagg ctaaggtggg aggatcactt   1560

gatcctggga ggtcaaggct gcag                                          1584
```

<210> SEQ ID NO 25
<211> LENGTH: 952
<212> TYPE: DNA
<213> ORGANISM: Homo sapiens

<400> SEQUENCE: 25

```
tccacccctc ctctcatggg tactgtnggg gaggatgggt gccacaggac cacacaggtg     60

gctgtctgag agggtagtgc ctgggaactt tctggaagcc tgtttgggga agcagatggg    120

gtgaaggatt cagttagtgt atgtggggtc gtgacaccat ctacccactg tctctctcct    180

gccttcatca tcctctagaa atacagcaac aattcctggc gatacctcag caaccggctg    240

ctggcaccca gcgactcgcc agagtggtta tcttttgatg tcaccggagt tgtgcggcag    300

tggttgagcc gtggaggggga aattgagggc tttcgcctta gcgcccactg ctcctgtgac    360

agcagggata acacactgca agtggacatc aacgggttca ctaccggccg ccgaggtgac    420

ctggccacca ttcatggcat gaaccggcct ttcctgcttc tcatggccac cccgctggag    480

agggcccagc atctgcaaag ctcccggcac cgccgagccc tggacaccaa ctattgcttc    540

agctccacgg agaagaactg ctgcgtgcgg cagctgtaca ttgacttccg caaggacctc    600

ggctggaagt ggatccacga gcccaagggc taccatgcca acttctgcct cgggccctgc    660
```

-continued

```
ccctacattt ggagcctgga cacgcagtac agcaagctca atgaacagaa cctcatccag    720

gaagtcccca acatctggca acgtgaagtt ggctaggagg aaggaagtgc cccaaagaga    780

acaagaagaa gaggaccctg cattgacgtt cctctgggaa gcactcattt cctacctttc    840

atttctaaga ccgcatgatc tgggacatcc ttcccttcct cgtcggttcg ctttattgtt    900

cggtctttta ggtcctcgtc cagtgggaca aattacaata ntttgcgctg ga            952


<210> SEQ ID NO 26
<211> LENGTH: 756
<212> TYPE: DNA
<213> ORGANISM: Homo sapiens

<400> SEQUENCE: 26

aaaaaatcaa ttttggaaga tgtcactgaa caactcttcc aatgtatttc tggattcagt     60

gcccagtaat accaatcgct ttcaagttag tgtcataaat gagaaccatg agagcagtgc    120

agctgcagat gacaatactg acccaccaca ttatgaagaa acctcttttg ggatgaagc    180

tcagaaaaga ctcagaatca gctttaggcc tgggaatcag gagtgctatg acaatttcct    240

ccacagtgga gaaactgcta aaacagatgc cagttttcac gcttatgatt ctcacacaaa    300

cacatactat ctacaaactt ttggccacaa caccatggat gccgttccca agatagagta    360

ctatcgtaac accggcagca tcagtgggcc caaggtcaac cgacccagcc tgcttgagat    420

tcacgagcaa ctcgcaaaga atgtggcagt caccccaagt tcagctgaca gagttgctaa    480

cggtgatggg atacctggag atgaacaagc tgaaaataag gaagatgatc aagctggtgt    540

tgtgaagttt ggatgggtga aaggtgtgct ggtaagatgc atgctgaaca tctggggagt    600

catgctcttc attcgcctct cctggattgt tggagaagct ggaattgagt atccttcttg    660

gcatgattgg taaaacttca ctgaacaaaa ataacttgtg agaaaactgg tgaaaatgtg    720

acctgactaa taaaaatgct gaattgttga actttt                              756


<210> SEQ ID NO 27
<211> LENGTH: 208
<212> TYPE: PRT
<213> ORGANISM: Homo sapiens

<400> SEQUENCE: 27

Ala Leu Gly Gly Thr Pro Met Leu Gly Lys Leu Ala Met Leu Leu Trp
  1               5                  10                  15

Val Gln Gln Ala Leu Leu Ala Leu Leu Leu Pro Thr Leu Leu Ala Gln
             20                  25                  30

Gly Glu Ala Arg Arg Ser Arg Asn Thr Thr Arg Pro Ala Leu Leu Arg
         35                  40                  45

Leu Ser Asp Tyr Leu Leu Thr Asn Tyr Arg Lys Gly Val Arg Pro Val
     50                  55                  60

Arg Asp Trp Arg Lys Pro Thr Thr Val Ser Ile Asp Val Ile Val Tyr
 65                  70                  75                  80

Ala Ile Leu Asn Val Asp Glu Lys Asn Gln Val Leu Thr Thr Tyr Ile
                 85                  90                  95

Trp Tyr Arg Gln Tyr Trp Thr Asp Glu Phe Leu Gln Trp Asn Pro Glu
            100                 105                 110

Asp Phe Asp Asn Ile Thr Lys Leu Ser Ile Pro Thr Asp Ser Ile Trp
        115                 120                 125

Val Pro Asp Ile Leu Ile Asn Glu Phe Val Asp Val Gly Lys Ser Pro
    130                 135                 140
```

-continued

```
Asn Ile Pro Tyr Val Tyr Ile Arg His Gln Gly Glu Val Gln Asn Tyr
145                 150                 155                 160

Lys Pro Leu Gln Val Val Thr Ala Cys Ser Leu Asp Ile Tyr Asn Phe
                165                 170                 175

Pro Phe Asp Val Gln Asn Cys Ser Leu Thr Phe Thr Ser Trp Leu His
            180                 185                 190

Thr Thr Gln Tyr Phe Thr Ser Ser Leu Cys Arg Leu Pro Asp Lys Val
        195                 200                 205


<210> SEQ ID NO 28
<211> LENGTH: 210
<212> TYPE: PRT
<213> ORGANISM: Homo sapiens

<400> SEQUENCE: 28

Asn Ser Gly Ser Leu Pro Leu Ser Glu Leu Gly Lys Leu Ala Met Leu
  1               5                  10                  15

Leu Trp Val Gln Gln Ala Leu Leu Ala Leu Leu Leu Pro Thr Leu Leu
            20                  25                  30

Ala Gln Gly Glu Ala Arg Arg Ser Arg Asn Thr Thr Arg Pro Ala Leu
        35                  40                  45

Leu Arg Leu Ser Asp Tyr Leu Leu Thr Asn Tyr Arg Lys Gly Val Arg
    50                  55                  60

Pro Val Arg Asp Trp Arg Lys Pro Thr Thr Val Ser Ile Asp Val Ile
 65                  70                  75                  80

Val Tyr Ala Ile Leu Asn Val Asp Glu Lys Asn Gln Val Leu Thr Thr
                85                  90                  95

Tyr Ile Trp Tyr Arg Gln Tyr Trp Thr Asp Glu Phe Leu Gln Trp Asn
            100                 105                 110

Pro Glu Asp Phe Asp Asn Ile Thr Lys Leu Ser Ile Pro Thr Asp Ser
        115                 120                 125

Ile Trp Val Pro Asp Ile Leu Ile Asn Glu Phe Val Asp Val Gly Lys
    130                 135                 140

Ser Pro Asn Ile Pro Tyr Val Tyr Ile Arg His Gln Gly Glu Val Gln
145                 150                 155                 160

Asn Tyr Lys Pro Leu Gln Val Val Thr Ala Cys Ser Leu Asp Ile Tyr
                165                 170                 175

Asn Phe Pro Phe Asp Val Gln Asn Cys Ser Leu Thr Phe Thr Ser Trp
            180                 185                 190

Leu His Thr Thr Gln Tyr Phe Thr Ser Ser Leu Cys Arg Leu Pro Asp
        195                 200                 205

Lys Val
    210


<210> SEQ ID NO 29
<211> LENGTH: 169
<212> TYPE: PRT
<213> ORGANISM: Homo sapiens

<400> SEQUENCE: 29

Lys Asn Arg Glu Gly Arg Ala Ser Val Thr Gly Cys Leu Ala Asp Leu
  1               5                  10                  15

Gln Gln Ser Asp Ser Asp Arg Ile Met Ala Met Met Glu Val Gln Gly
            20                  25                  30

Gly Pro Ser Leu Gly Gln Thr Cys Val Leu Ile Val Ile Phe Thr Val
        35                  40                  45
```

-continued

```
Leu Leu Gln Ser Leu Cys Val Ala Val Thr Tyr Val Tyr Phe Thr Asn
     50                  55                  60

Glu Leu Lys Gln Met Gln Asp Lys Tyr Ser Lys Ser Gly Ile Ala Cys
 65                  70                  75                  80

Phe Leu Lys Glu Asp Asp Ser Tyr Trp Asp Pro Asn Asp Glu Glu Ser
                 85                  90                  95

Met Asn Ser Pro Cys Trp Gln Val Lys Trp Gln Leu Arg Gln Leu Val
            100                 105                 110

Arg Lys Met Ile Leu Arg Thr Ser Glu Glu Thr Ile Ser Thr Val Gln
        115                 120                 125

Glu Lys Gln Gln Asn Ile Ser Pro Leu Val Arg Glu Arg Gly Pro Gln
    130                 135                 140

Arg Val Ala Ala His Ile Thr Gly Thr Arg Gly Arg Ser Asn Thr Leu
145                 150                 155                 160

Ser Ser Pro Asn Ser Arg Arg Ile Val
                165


<210> SEQ ID NO 30
<211> LENGTH: 271
<212> TYPE: PRT
<213> ORGANISM: Homo sapiens

<400> SEQUENCE: 30

Lys Asn Arg Glu Gly Arg Ala Ser Val Thr Gly Cys Leu Ala Asp Leu
  1               5                  10                  15

Gln Gln Ser Asp Ser Asp Arg Ile Met Ala Met Met Glu Val Gln Gly
             20                  25                  30

Gly Pro Ser Leu Gly Gln Thr Cys Val Leu Ile Val Ile Phe Thr Val
         35                  40                  45

Leu Leu Gln Ser Leu Cys Val Ala Val Thr Tyr Val Tyr Phe Thr Asn
     50                  55                  60

Glu Leu Lys Gln Met Gln Asp Lys Tyr Ser Lys Ser Gly Ile Ala Cys
 65                  70                  75                  80

Phe Leu Lys Glu Asp Asp Ser Tyr Trp Asp Pro Asn Asp Glu Glu Ser
                 85                  90                  95

Met Asn Ser Pro Cys Trp Gln Val Lys Trp Gln Leu Arg Gln Leu Val
            100                 105                 110

Arg Lys Lys Ser Asn Lys Ile Phe Leu Pro Leu Val Arg Glu Arg Gly
        115                 120                 125

Pro Gln Arg Val Ala Ala His Ile Thr Gly Thr Arg Gly Arg Ser Asn
    130                 135                 140

Thr Leu Ser Ser Pro Asn Ser Lys Asn Glu Lys Ala Leu Gly Arg Lys
145                 150                 155                 160

Ile Asn Ser Trp Glu Ser Ser Arg Ser Gly His Ser Phe Leu Ser Asn
                165                 170                 175

Leu His Leu Arg Asn Gly Glu Leu Val Ile His Glu Lys Gly Phe Tyr
            180                 185                 190

Tyr Ile Tyr Ser Gln Thr Tyr Phe Arg Phe Gln Glu Glu Ile Lys Glu
        195                 200                 205

Asn Thr Lys Asn Asp Lys Gln Met Val Gln Tyr Ile Tyr Lys Tyr Thr
    210                 215                 220

Ser Tyr Pro Asp Pro Ile Leu Leu Met Lys Ser Ala Arg Asn Ser Cys
225                 230                 235                 240

Trp Ser Lys Asp Ala Glu Tyr Gly Leu Tyr Ser Ile Tyr Gln Gly Ile
                245                 250                 255
```

```
Asp Met Asp His Glu Ala Ser Phe Phe Gly Ala Phe Leu Val Gly
            260                 265                 270


<210> SEQ ID NO 31
<211> LENGTH: 122
<212> TYPE: PRT
<213> ORGANISM: Homo sapiens

<400> SEQUENCE: 31

Lys Asn Arg Glu Gly Arg Ala Ser Val Thr Gly Cys Leu Ala Asp Leu
  1               5                  10                  15

Gln Gln Ser Asp Ser Asp Arg Ile Met Ala Met Met Glu Val Gln Gly
             20                  25                  30

Gly Pro Ser Leu Gly Gln Thr Cys Val Leu Ile Val Ile Phe Thr Val
         35                  40                  45

Leu Leu Gln Ser Leu Cys Val Ala Val Thr Tyr Val Tyr Phe Thr Asn
     50                  55                  60

Glu Leu Lys Gln Met Gln Asp Lys Tyr Ser Lys Ser Gly Ile Ala Cys
 65                  70                  75                  80

Phe Leu Lys Glu Asp Asp Ser Tyr Trp Asp Pro Asn Asp Glu Glu Ser
                 85                  90                  95

Met Asn Ser Pro Cys Trp Gln Val Lys Trp Gln Leu Arg Gln Leu Val
            100                 105                 110

Arg Lys Lys Ser Asn Lys Ile Phe Leu Pro
        115                 120


<210> SEQ ID NO 32
<211> LENGTH: 120
<212> TYPE: PRT
<213> ORGANISM: Homo sapiens

<400> SEQUENCE: 32

Lys Asn Arg Glu Gly Arg Ala Ser Val Thr Gly Cys Leu Ala Asp Leu
  1               5                  10                  15

Gln Gln Ser Asp Ser Asp Arg Ile Met Ala Met Met Glu Val Gln Gly
             20                  25                  30

Gly Pro Ser Leu Gly Gln Thr Cys Val Leu Ile Val Ile Phe Thr Val
         35                  40                  45

Leu Leu Gln Ser Leu Cys Val Ala Val Thr Tyr Val Tyr Phe Thr Asn
     50                  55                  60

Glu Leu Lys Gln Met Gln Asp Lys Tyr Ser Lys Ser Gly Ile Ala Cys
 65                  70                  75                  80

Phe Leu Lys Glu Asp Asp Ser Tyr Trp Asp Pro Asn Asp Glu Glu Ser
                 85                  90                  95

Met Asn Ser Pro Cys Trp Gln Val Lys Trp Gln Leu Arg Gln Leu Val
            100                 105                 110

Arg Lys Val Gly Asn Leu Thr Arg
        115                 120


<210> SEQ ID NO 33
<211> LENGTH: 218
<212> TYPE: PRT
<213> ORGANISM: Homo sapiens

<400> SEQUENCE: 33

Leu Ala Arg Ala Pro Ser Gly Pro Ala Ala Trp Ser His Leu Ala Met
  1               5                  10                  15
```

-continued

```
Val Arg Leu Pro Leu Gln Cys Val Leu Trp Gly Cys Leu Leu Thr Ala
            20                  25                  30

Val His Pro Glu Pro Pro Thr Ala Cys Arg Glu Lys Gln Tyr Leu Ile
        35                  40                  45

Asn Ser Gln Cys Cys Ser Leu Cys Gln Pro Gly Gln Lys Leu Val Ser
    50                  55                  60

Asp Cys Thr Glu Phe Thr Glu Thr Glu Cys Leu Pro Cys Gly Glu Ser
65                  70                  75                  80

Glu Phe Leu Asp Thr Trp Asn Arg Glu Thr His Cys His Gln His Lys
                85                  90                  95

Tyr Cys Asp Pro Asn Leu Gly Leu Arg Val Gln Gln Lys Gly Thr Ser
            100                 105                 110

Glu Thr Asp Thr Ile Cys Thr Cys Glu Glu Gly Trp His Cys Thr Ser
        115                 120                 125

Glu Ala Cys Glu Ser Cys Val Leu His Arg Ser Cys Ser Pro Gly Phe
    130                 135                 140

Gly Val Lys Gln Ile Ala Thr Gly Val Ser Asp Thr Ile Cys Glu Pro
145                 150                 155                 160

Cys Pro Val Gly Phe Phe Ser Asn Val Ser Ser Ala Phe Glu Lys Cys
                165                 170                 175

His Pro Trp Thr Arg Ser Pro Gly Ser Ala Glu Ser Pro Gly Gly Asp
            180                 185                 190

Pro His His Leu Arg Asp Pro Val Cys His Pro Leu Gly Ala Gly Leu
        195                 200                 205

Tyr Gln Lys Gly Gly Gln Glu Ala Asn Gln
    210                 215


<210> SEQ ID NO 34
<211> LENGTH: 198
<212> TYPE: PRT
<213> ORGANISM: Homo sapiens

<400> SEQUENCE: 34

Gly Arg Ala Arg Ser Thr Gln Arg Glu Glu Ala Gly Glu Gly Ala Arg
  1               5                  10                  15

Ser Arg Glu Lys Ala Thr Arg Pro Lys Leu Lys Lys Met Lys Ser Gln
            20                  25                  30

Thr Gly Gln Val Gly Glu Lys Gln Ser Leu Lys Cys Glu Ala Ala Ala
        35                  40                  45

Gly Asn Pro Gln Pro Ser Tyr Arg Trp Phe Lys Asp Gly Lys Glu Leu
    50                  55                  60

Asn Arg Ser Arg Asp Ile Arg Ile Lys Tyr Gly Asn Gly Arg Lys Asn
65                  70                  75                  80

Ser Arg Leu Gln Phe Asn Lys Val Lys Val Glu Asp Ala Gly Glu Tyr
                85                  90                  95

Val Cys Glu Ala Glu Asn Ile Leu Gly Lys Asp Thr Val Arg Gly Arg
            100                 105                 110

Leu Tyr Val Asn Ser Val Ser Thr Thr Leu Ser Ser Trp Ser Gly His
        115                 120                 125

Ala Arg Lys Cys Asn Glu Thr Ala Lys Ser Tyr Cys Val Asn Gly Gly
    130                 135                 140

Val Cys Tyr Tyr Ile Glu Gly Ile Asn Gln Leu Ser Cys Lys Ala Pro
145                 150                 155                 160

Gly Leu His Cys Leu Glu Leu Gly Thr Gln Ser His His Phe Pro Ile
                165                 170                 175
```

```
Ser Ala Ser Pro Gly Ser Ser Gln Gly Ser Trp Asn Gln Leu Pro Gln
            180                 185                 190

His Pro Leu Ser Ala Leu
        195


<210> SEQ ID NO 35
<211> LENGTH: 637
<212> TYPE: PRT
<213> ORGANISM: Homo sapiens

<400> SEQUENCE: 35

Gly Arg Ala Arg Ser Thr Gln Arg Glu Glu Ala Gly Glu Gly Ala Arg
  1               5                  10                  15

Ser Arg Glu Lys Ala Thr Arg Pro Lys Leu Lys Lys Met Lys Ser Gln
             20                  25                  30

Thr Gly Gln Val Gly Glu Lys Gln Ser Leu Lys Cys Glu Ala Ala Ala
         35                  40                  45

Gly Asn Pro Gln Pro Ser Tyr Arg Trp Phe Lys Asp Gly Lys Glu Leu
     50                  55                  60

Asn Arg Ser Arg Asp Ile Arg Ile Lys Tyr Gly Asn Gly Arg Lys Asn
 65                  70                  75                  80

Ser Arg Leu Gln Phe Asn Lys Val Lys Val Glu Asp Ala Gly Glu Tyr
                 85                  90                  95

Val Cys Glu Ala Glu Asn Ile Leu Gly Lys Asp Thr Val Arg Gly Arg
            100                 105                 110

Leu Tyr Val Asn Ser Val Ser Thr Thr Leu Ser Ser Trp Ser Gly His
        115                 120                 125

Ala Arg Lys Cys Asn Glu Thr Ala Lys Ser Tyr Cys Val Asn Gly Gly
    130                 135                 140

Val Cys Tyr Tyr Ile Glu Gly Ile Asn Gln Leu Ser Cys Lys Cys Pro
145                 150                 155                 160

Asn Gly Phe Phe Gly Gln Arg Cys Leu Glu Lys Leu Pro Leu Arg Leu
                165                 170                 175

Tyr Met Pro Asp Pro Lys Gln Lys Ala Glu Glu Leu Tyr Gln Lys Arg
            180                 185                 190

Val Leu Thr Ile Thr Gly Ile Cys Val Ala Leu Leu Val Val Gly Ile
        195                 200                 205

Val Cys Val Val Ala Tyr Cys Lys Thr Lys Lys Gln Arg Lys Gln Met
    210                 215                 220

His Asn His Leu Arg Gln Asn Met Cys Pro Ala His Gln Asn Arg Ser
225                 230                 235                 240

Leu Ala Asn Gly Pro Ser His Pro Arg Leu Asp Pro Glu Glu Ile Gln
                245                 250                 255

Met Ala Asp Tyr Ile Ser Lys Asn Val Pro Ala Thr Asp His Val Ile
            260                 265                 270

Arg Arg Glu Thr Glu Thr Thr Phe Ser Gly Ser His Ser Cys Ser Pro
        275                 280                 285

Ser His His Cys Ser Thr Ala Thr Pro Thr Ser Ser His Arg His Glu
    290                 295                 300

Ser His Thr Trp Ser Leu Glu Arg Ser Glu Ser Leu Thr Ser Asp Ser
305                 310                 315                 320

Gln Ser Gly Ile Met Leu Ser Ser Val Gly Thr Ser Lys Cys Asn Ser
                325                 330                 335

Pro Ala Cys Val Glu Ala Arg Ala Arg Arg Ala Ala Ala Tyr Asn Leu
```

-continued

```
            340                 345                 350

Glu Glu Arg Arg Arg Ala Thr Ala Pro Pro Tyr His Asp Ser Val Asp
        355                 360                 365

Ser Leu Arg Asp Ser Pro His Ser Glu Arg Tyr Val Ser Ala Leu Thr
    370                 375                 380

Thr Pro Ala Arg Leu Ser Pro Val Asp Phe His Tyr Ser Leu Ala Thr
385                 390                 395                 400

Gln Val Pro Thr Phe Glu Ile Thr Ser Pro Asn Ser Ala His Ala Val
                405                 410                 415

Ser Leu Pro Pro Ala Ala Pro Ile Ser Tyr Arg Leu Ala Glu Gln Gln
            420                 425                 430

Pro Leu Leu Arg His Pro Ala Pro Pro Gly Pro Gly Pro Gly Pro Gly
        435                 440                 445

Pro Gly Pro Gly Pro Gly Ala Asp Met Gln Arg Ser Tyr Asp Ser Tyr
    450                 455                 460

Tyr Tyr Pro Ala Ala Gly Pro Gly Pro Arg Arg Gly Thr Cys Ala Leu
465                 470                 475                 480

Gly Gly Ser Leu Gly Ser Leu Pro Ala Ser Pro Phe Arg Ile Pro Glu
                485                 490                 495

Asp Asp Glu Tyr Glu Thr Thr Gln Glu Cys Ala Pro Pro Pro Pro Pro
            500                 505                 510

Arg Pro Arg Ala Arg Gly Ala Ser Arg Arg Thr Ser Ala Gly Pro Arg
        515                 520                 525

Arg Trp Arg Arg Ser Arg Leu Asn Gly Leu Ala Ala Gln Arg Ala Arg
    530                 535                 540

Ala Ala Arg Asp Ser Leu Ser Leu Ser Ser Gly Ser Gly Gly Gly Ser
545                 550                 555                 560

Ala Ser Ala Ser Asp Asp Asp Ala Asp Asp Ala Asp Gly Ala Leu Ala
                565                 570                 575

Ala Glu Ser Thr Pro Phe Leu Gly Leu Arg Gly Ala His Asp Ala Leu
            580                 585                 590

Arg Ser Asp Ser Pro Pro Leu Cys Pro Ala Ala Asp Ser Arg Thr Tyr
        595                 600                 605

Tyr Ser Leu Asp Ser His Ser Thr Arg Ala Ser Ser Arg His Ser Arg
    610                 615                 620

Gly Pro Pro Pro Arg Ala Lys Gln Asp Ser Ala Pro Leu
625                 630                 635


<210> SEQ ID NO 36
<211> LENGTH: 421
<212> TYPE: PRT
<213> ORGANISM: Homo sapiens

<400> SEQUENCE: 36

Ala Ala Glu Pro Pro Lys Trp Pro Gly Gln Met Arg Gln Val Cys Cys
  1               5                  10                  15

Ser Ala Leu Pro Pro Pro Pro Leu Glu Lys Gly Arg Cys Ser Ser Tyr
             20                  25                  30

Ser Asp Ser Ser Ser Ser Ser Ser Glu Arg Ser Ser Ser Ser Ser Ser
         35                  40                  45

Ser Ser Ser Glu Ser Gly Ser Ser Ser Arg Ser Ser Ser Asn Asn Ser
     50                  55                  60

Ser Ile Ser Arg Pro Ala Ala Pro Pro Xaa Pro Arg Pro Gln Gln Gln
 65                  70                  75                  80
```

-continued

```
Pro Gln Pro Arg Ser Pro Ala Ala Arg Arg Ala Ala Ala Arg Ser Arg
                85                  90                  95

Ala Ala Ala Ala Gly Gly Met Arg Arg Asp Pro Ala Pro Gly Phe Ser
            100                 105                 110

Met Leu Leu Phe Gly Val Ser Leu Ala Cys Tyr Ser Pro Ser Leu Lys
        115                 120                 125

Ser Val Gln Asp Gln Ala Tyr Lys Ala Pro Val Val Val Glu Gly Lys
    130                 135                 140

Val Gln Gly Leu Val Pro Ala Gly Gly Ser Ser Ser Asn Ser Thr Arg
145                 150                 155                 160

Glu Pro Pro Ala Ser Gly Arg Val Ala Leu Val Lys Val Leu Asp Lys
                165                 170                 175

Trp Pro Leu Arg Ser Gly Gly Leu Gln Arg Glu Gln Val Ile Ser Val
            180                 185                 190

Gly Ser Cys Val Pro Leu Glu Arg Asn Gln Arg Tyr Ile Phe Phe Leu
        195                 200                 205

Glu Pro Thr Glu Gln Pro Leu Val Phe Lys Thr Ala Phe Ala Pro Leu
    210                 215                 220

Asp Thr Asn Gly Lys Asn Leu Lys Lys Glu Val Gly Lys Ile Leu Cys
225                 230                 235                 240

Thr Asp Cys Ala Thr Arg Pro Lys Leu Lys Lys Met Lys Ser Gln Thr
                245                 250                 255

Gly Gln Val Gly Glu Lys Gln Ser Leu Lys Cys Glu Ala Ala Ala Gly
            260                 265                 270

Asn Pro Gln Pro Ser Tyr Arg Trp Phe Lys Asp Gly Lys Glu Leu Asn
        275                 280                 285

Arg Ser Arg Asp Ile Arg Ile Lys Tyr Gly Asn Gly Arg Lys Asn Ser
    290                 295                 300

Arg Leu Gln Phe Asn Lys Val Lys Val Glu Asp Ala Gly Glu Tyr Val
305                 310                 315                 320

Cys Glu Ala Glu Asn Ile Leu Gly Lys Asp Thr Val Arg Gly Arg Leu
                325                 330                 335

Tyr Val Asn Ser Val Ser Thr Thr Leu Ser Ser Trp Ser Gly His Ala
            340                 345                 350

Arg Lys Cys Asn Glu Thr Ala Lys Ser Tyr Cys Val Asn Gly Gly Val
        355                 360                 365

Cys Tyr Tyr Ile Glu Gly Ile Asn Gln Leu Ser Cys Lys Ala Pro Gly
    370                 375                 380

Leu His Cys Leu Glu Leu Gly Thr Gln Ser His His Phe Pro Ile Ser
385                 390                 395                 400

Ala Ser Pro Gly Ser Ser Gln Gly Ser Trp Asn Gln Leu Pro Gln His
                405                 410                 415

Pro Leu Ser Ala Leu
            420


<210> SEQ ID NO 37
<211> LENGTH: 270
<212> TYPE: PRT
<213> ORGANISM: Homo sapiens

<400> SEQUENCE: 37

Tyr Pro Ala Ser Ile Val Ser Lys Ser Ser Thr Val Met Thr Leu Trp
  1               5                  10                  15

Glu Ile Leu Val Val Cys Pro Ser Pro Leu Trp Ile Asn Leu Gln Val
             20                  25                  30
```

-continued

```
Ser Trp Ile Val Thr Gly Leu Ser Ser Phe Cys Pro Gly Lys Ile Gln
        35                  40                  45

Val Asn Ser Thr Ser Lys Thr Gly Ser Thr Tyr Ile Phe Phe Thr Glu
    50                  55                  60

Lys Gly Glu Leu Phe Val Pro Ser Pro Ser Tyr Phe Asp Val Val Tyr
65                  70                  75                  80

Leu Asn Pro Asp Arg Gln Ala Val Val Pro Cys Arg Val Thr Val Leu
                85                  90                  95

Ser Ala Lys Val Thr Leu His Arg Glu Phe Pro Ala Lys Glu Ile Pro
            100                 105                 110

Ala Asn Gly Thr Asp Ile Val Tyr Asp Met Lys Arg Gly Phe Val Tyr
        115                 120                 125

Leu Gln Pro His Ser Glu His Gln Gly Val Val Tyr Cys Arg Ala Glu
    130                 135                 140

Ala Gly Gly Arg Ser Gln Ile Ser Val Lys Tyr Gln Leu Leu Tyr Val
145                 150                 155                 160

Ala Val Pro Ser Gly Pro Pro Ser Thr Thr Ile Leu Ala Ser Ser Asn
                165                 170                 175

Lys Val Lys Ser Gly Asp Asp Ile Ser Val Leu Cys Thr Val Leu Gly
            180                 185                 190

Glu Pro Asp Val Glu Val Glu Phe Thr Trp Ile Phe Pro Gly Gln Lys
        195                 200                 205

Asp Glu Arg Pro Val Thr Ile Gln Asp Thr Trp Arg Leu Ile His Arg
    210                 215                 220

Gly Leu Gly His Thr Thr Arg Ile Ser Gln Ser Val Ile Thr Val Glu
225                 230                 235                 240

Asp Phe Glu Thr Ile Asp Ala Gly Tyr Tyr Ile Cys Thr Ala Gln Asn
                245                 250                 255

Leu Gln Gly Gln Thr Thr Val Ala Thr Thr Val Glu Phe Ser
            260                 265                 270


<210> SEQ ID NO 38
<211> LENGTH: 223
<212> TYPE: PRT
<213> ORGANISM: Homo sapiens

<400> SEQUENCE: 38

Lys Asn Gln Phe Trp Lys Met Ser Leu Asn Asn Ser Ser Asn Val Phe
  1               5                  10                  15

Leu Asp Ser Val Pro Ser Asn Thr Asn Arg Phe Gln Val Ser Val Ile
            20                  25                  30

Asn Glu Asn His Glu Ser Ser Ala Ala Ala Asp Asp Asn Thr Asp Pro
        35                  40                  45

Pro His Tyr Glu Glu Thr Ser Phe Gly Asp Glu Ala Gln Lys Arg Leu
    50                  55                  60

Arg Ile Ser Phe Arg Pro Gly Asn Gln Glu Cys Tyr Asp Asn Phe Leu
65                  70                  75                  80

His Ser Gly Glu Thr Ala Lys Thr Asp Ala Ser Phe His Ala Tyr Asp
                85                  90                  95

Ser His Thr Asn Thr Tyr Tyr Leu Gln Thr Phe Gly His Asn Thr Met
            100                 105                 110

Asp Ala Val Pro Lys Ile Glu Tyr Tyr Arg Asn Thr Gly Ser Ile Ser
        115                 120                 125

Gly Pro Lys Val Asn Arg Pro Ser Leu Leu Glu Ile His Glu Gln Leu
```

-continued

```
    130                 135                 140

Ala Lys Asn Val Ala Val Thr Pro Ser Ser Ala Asp Arg Val Ala Asn
145                 150                 155                 160

Gly Asp Gly Ile Pro Gly Asp Glu Gln Ala Glu Asn Lys Glu Asp Asp
                165                 170                 175

Gln Ala Gly Val Val Lys Phe Gly Trp Val Lys Gly Val Leu Val Arg
            180                 185                 190

Cys Met Leu Asn Ile Trp Gly Val Met Leu Phe Ile Arg Leu Ser Trp
        195                 200                 205

Ile Val Gly Glu Ala Gly Ile Glu Tyr Pro Ser Trp His Asp Trp
    210                 215                 220


<210> SEQ ID NO 39
<211> LENGTH: 460
<212> TYPE: PRT
<213> ORGANISM: Homo sapiens

<400> SEQUENCE: 39

Met Ala Val Thr Gln Phe Ile His Phe Arg Glu Glu Ile Met Gly Asn
  1               5                  10                  15

Met Phe Phe Ile Ile Ile Phe Ser Thr Lys Asp Lys Leu Cys Tyr Arg
             20                  25                  30

Asp Gly Glu Glu Tyr Glu Trp Lys Glu Thr Ala Arg Trp Leu Lys Phe
         35                  40                  45

Glu Glu Asp Val Glu Asp Gly Gly Asp Arg Trp Ser Lys Pro Tyr Val
     50                  55                  60

Ala Thr Leu Ser Leu His Ser Leu Phe Glu Leu Arg Ser Cys Ile Leu
 65                  70                  75                  80

Asn Gly Thr Val Met Leu Asp Met Arg Ala Ser Thr Leu Asp Glu Ile
                 85                  90                  95

Ala Asp Met Val Leu Asp Asn Met Ile Ala Ser Gly Gln Leu Asp Glu
            100                 105                 110

Ser Ile Arg Glu Asn Val Arg Glu Ala Leu Leu Lys Arg His His His
        115                 120                 125

Gln Asn Glu Lys Arg Phe Thr Ser Arg Ile Pro Leu Val Arg Ser Phe
    130                 135                 140

Ala Asp Ile Gly Lys Lys His Ser Asp Pro His Leu Leu Glu Arg Asn
145                 150                 155                 160

Gly Ile Leu Ala Ser Pro Gln Ser Ala Pro Gly Asn Leu Asp Asn Ser
                165                 170                 175

Lys Ser Gly Glu Ile Lys Gly Asn Gly Ser Gly Gly Ser Arg Glu Asn
            180                 185                 190

Ser Thr Val Asp Phe Ser Lys Val Asp Met Asn Phe Met Arg Lys Ile
        195                 200                 205

Pro Thr Gly Ala Glu Ala Ser Asn Val Leu Val Gly Glu Val Asp Phe
    210                 215                 220

Leu Glu Arg Pro Ile Ile Ala Phe Val Arg Leu Ala Pro Ala Val Leu
225                 230                 235                 240

Leu Thr Gly Leu Thr Glu Val Pro Val Pro Thr Arg Phe Leu Phe Leu
                245                 250                 255

Leu Leu Gly Pro Ala Gly Lys Ala Pro Gln Tyr His Glu Ile Gly Arg
            260                 265                 270

Ser Ile Ala Thr Leu Met Thr Asp Glu Ile Phe His Asp Val Ala Tyr
        275                 280                 285
```

-continued

```
Lys Ala Lys Asp Arg Asn Asp Leu Leu Ser Gly Ile Asp Glu Phe Leu
    290                 295                 300

Asp Gln Val Thr Val Leu Pro Pro Gly Glu Trp Asp Pro Ser Ile Arg
305                 310                 315                 320

Ile Glu Pro Pro Lys Ser Val Pro Ser Gln Glu Lys Arg Lys Ile Pro
                325                 330                 335

Val Phe His Asn Gly Ser Thr Pro Thr Leu Gly Glu Thr Pro Lys Glu
            340                 345                 350

Ala Ala His His Ala Gly Pro Glu Leu Gln Arg Thr Gly Arg Leu Phe
        355                 360                 365

Gly Gly Leu Ile Leu Asp Ile Lys Arg Lys Ala Pro Phe Phe Leu Ser
    370                 375                 380

Asp Phe Lys Asp Ala Leu Ser Leu Gln Cys Leu Ala Ser Ile Leu Phe
385                 390                 395                 400

Leu Tyr Cys Ala Cys Met Ser Pro Val Ile Thr Phe Gly Gly Leu Leu
                405                 410                 415

Gly Glu Ala Thr Glu Gly Arg Ile Val Ser Thr Lys Ile Gly Ser Gly
            420                 425                 430

Gln Ala Phe Ser Ser Ser Glu Ala Ser Val Cys Met His Leu Ser His
        435                 440                 445

Tyr Ser Tyr Phe Tyr Leu Lys Ser Leu Pro Thr Ala
    450                 455                 460


<210> SEQ ID NO 40
<211> LENGTH: 175
<212> TYPE: PRT
<213> ORGANISM: Homo sapiens

<400> SEQUENCE: 40

Met Ala Val Thr Gln Phe Ile His Phe Arg Glu Glu Ile Met Gly Asn
  1               5                  10                  15

Met Phe Phe Ile Ile Ile Phe Ser Thr Lys Asp Lys Leu Cys Tyr Arg
            20                  25                  30

Asp Gly Glu Glu Tyr Glu Trp Lys Glu Thr Ala Arg Trp Leu Lys Phe
        35                  40                  45

Glu Glu Asp Val Glu Asp Gly Gly Asp Arg Trp Ser Lys Pro Tyr Val
     50                  55                  60

Ala Thr Leu Ser Leu His Ser Leu Phe Glu Leu Arg Ser Cys Ile Leu
 65                  70                  75                  80

Asn Gly Thr Val Met Leu Asp Met Arg Ala Ser Thr Leu Asp Glu Ile
                 85                  90                  95

Ala Asp Met Val Leu Asp Asn Met Ile Ala Ser Gly Gln Leu Asp Glu
            100                 105                 110

Ser Ile Arg Glu Asn Val Arg Glu Ala Leu Leu Lys Arg His His His
        115                 120                 125

Gln Asn Glu Lys Arg Phe Thr Ser Arg Ile Pro Leu Val Arg Ser Phe
    130                 135                 140

Ala Asp Ile Gly Lys Lys His Ser Asp Pro His Leu Leu Glu Arg Asn
145                 150                 155                 160

Gly Glu Ile Ser Cys Gly Ile Gln Phe Leu Leu Thr Leu Leu Leu
                165                 170                 175


<210> SEQ ID NO 41
<211> LENGTH: 922
<212> TYPE: PRT
<213> ORGANISM: Homo sapiens
```

-continued

<400> SEQUENCE: 41

```
Ile Asp Met Val Leu Asp Asn Met Ile Ala Ser Gly Gln Leu Asp Glu
  1               5                  10                  15

Ser Ile Arg Glu Asn Val Arg Glu Ala Leu Leu Lys Arg His His His
             20                  25                  30

Gln Asn Glu Lys Arg Phe Thr Ser Arg Ile Pro Leu Val Arg Ser Phe
         35                  40                  45

Ala Asp Ile Gly Lys Lys His Ser Asp Pro His Leu Leu Glu Arg Asn
     50                  55                  60

Gly Ile Leu Ala Ser Pro Gln Ser Ala Pro Gly Asn Leu Asp Asn Ser
 65                  70                  75                  80

Lys Ser Gly Glu Ile Lys Gly Asn Gly Ser Gly Gly Ser Arg Glu Asn
                 85                  90                  95

Ser Thr Val Asp Phe Ser Lys Val Asp Met Asn Phe Met Arg Lys Ile
            100                 105                 110

Pro Thr Gly Ala Glu Ala Ser Asn Val Leu Val Gly Glu Val Asp Phe
        115                 120                 125

Leu Glu Arg Pro Ile Ile Ala Phe Val Arg Leu Ala Pro Ala Val Leu
    130                 135                 140

Leu Thr Gly Leu Thr Glu Val Pro Val Pro Thr Arg Phe Leu Phe Leu
145                 150                 155                 160

Leu Leu Gly Pro Ala Gly Lys Ala Pro Gln Tyr His Glu Ile Gly Arg
                165                 170                 175

Ser Ile Ala Thr Leu Met Thr Asp Glu Ile Phe His Asp Val Ala Tyr
            180                 185                 190

Lys Ala Lys Asp Arg Asn Asp Leu Leu Ser Gly Ile Asp Glu Phe Leu
        195                 200                 205

Asp Gln Val Thr Val Leu Pro Pro Gly Glu Trp Asp Pro Ser Ile Arg
    210                 215                 220

Ile Glu Pro Pro Lys Ser Val Pro Ser Gln Glu Lys Arg Lys Ile Pro
225                 230                 235                 240

Val Phe His Asn Gly Ser Thr Pro Thr Leu Gly Glu Thr Pro Lys Glu
                245                 250                 255

Ala Ala His His Ala Gly Pro Glu Leu Gln Arg Thr Gly Arg Leu Phe
            260                 265                 270

Gly Gly Leu Ile Leu Asp Ile Lys Arg Lys Ala Pro Phe Phe Leu Ser
        275                 280                 285

Asp Phe Lys Asp Ala Leu Ser Leu Gln Cys Leu Ala Ser Ile Leu Phe
    290                 295                 300

Leu Tyr Cys Ala Cys Met Ser Pro Val Ile Thr Phe Gly Gly Leu Leu
305                 310                 315                 320

Gly Glu Ala Thr Glu Gly Arg Ile Ser Ala Ile Glu Ser Leu Phe Gly
                325                 330                 335

Ala Ser Leu Thr Gly Ile Ala Tyr Ser Leu Phe Ala Gly Gln Pro Leu
            340                 345                 350

Thr Ile Leu Gly Ser Thr Gly Pro Val Leu Val Phe Glu Lys Ile Leu
        355                 360                 365

Tyr Lys Phe Cys Arg Asp Tyr Gln Leu Ser Tyr Leu Ser Leu Arg Thr
    370                 375                 380

Ser Ile Gly Leu Trp Thr Ser Phe Leu Cys Ile Val Leu Val Ala Thr
385                 390                 395                 400

Asp Ala Ser Ser Leu Val Cys Tyr Ile Thr Arg Phe Thr Glu Glu Ala
```

-continued

```
                405                 410                 415

Phe Ala Ala Leu Ile Cys Ile Ile Phe Ile Tyr Glu Ala Leu Glu Lys
            420                 425                 430

Leu Phe Asp Leu Gly Glu Thr Tyr Ala Phe Asn Met His Asn Asn Leu
        435                 440                 445

Asp Lys Leu Thr Ser Tyr Ser Cys Val Cys Thr Glu Pro Pro Asn Pro
    450                 455                 460

Ser Asn Glu Thr Leu Ala Gln Trp Lys Lys Asp Asn Ile Thr Ala His
465                 470                 475                 480

Asn Ile Ser Trp Arg Asn Leu Thr Val Ser Glu Cys Lys Lys Leu Arg
                485                 490                 495

Gly Val Phe Leu Gly Ser Ala Cys Gly His His Gly Pro Tyr Ile Pro
            500                 505                 510

Asp Val Leu Phe Trp Cys Val Ile Leu Phe Phe Thr Thr Phe Phe Leu
        515                 520                 525

Ser Ser Phe Leu Lys Gln Phe Lys Thr Lys Arg Tyr Phe Pro Thr Lys
    530                 535                 540

Val Arg Ser Thr Ile Ser Asp Phe Ala Val Phe Leu Thr Ile Val Ile
545                 550                 555                 560

Met Val Thr Ile Asp Tyr Leu Val Gly Val Pro Ser Pro Lys Leu His
                565                 570                 575

Val Pro Glu Lys Phe Glu Pro Thr His Pro Glu Arg Gly Trp Ile Ile
            580                 585                 590

Ser Pro Leu Gly Asp Asn Pro Trp Trp Thr Leu Leu Ile Ala Ala Ile
        595                 600                 605

Pro Ala Leu Leu Cys Thr Ile Leu Ile Phe Met Asp Gln Gln Ile Thr
    610                 615                 620

Ala Val Ile Ile Asn Arg Lys Glu His Lys Leu Lys Lys Gly Ala Gly
625                 630                 635                 640

Tyr His Leu Asp Leu Leu Met Val Gly Val Met Leu Gly Val Cys Ser
                645                 650                 655

Val Met Gly Leu Pro Trp Phe Val Ala Ala Thr Val Leu Ser Ile Ser
            660                 665                 670

His Val Asn Ser Leu Lys Val Glu Ser Glu Cys Ser Ala Pro Gly Glu
        675                 680                 685

Gln Pro Lys Phe Leu Gly Ile Arg Glu Gln Arg Val Thr Gly Leu Met
    690                 695                 700

Ile Phe Ile Leu Met Gly Leu Ser Val Phe Met Thr Ser Val Leu Lys
705                 710                 715                 720

Phe Ile Pro Met Pro Val Leu Tyr Gly Val Phe Leu Tyr Met Gly Val
                725                 730                 735

Ser Ser Leu Lys Gly Ile Gln Leu Phe Asp Arg Ile Lys Leu Phe Gly
            740                 745                 750

Met Pro Ala Lys His Gln Pro Asp Leu Ile Tyr Leu Arg Tyr Val Pro
        755                 760                 765

Leu Trp Lys Val His Ile Phe Thr Val Ile Gln Leu Thr Cys Leu Val
    770                 775                 780

Leu Leu Trp Val Ile Lys Val Ser Ala Ala Ala Val Val Phe Pro Met
785                 790                 795                 800

Met Val Leu Ala Leu Val Phe Val Arg Lys Leu Met Asp Leu Cys Phe
                805                 810                 815

Thr Lys Arg Glu Leu Ser Trp Leu Asp Asp Leu Met Pro Glu Ser Lys
            820                 825                 830
```

-continued

```
Lys Lys Lys Glu Asp Asp Lys Lys Lys Lys Glu Lys Glu Glu Ala Glu
        835                 840                 845

Arg Met Leu Gln Asp Asp Asp Asp Thr Val His Leu Pro Phe Glu Gly
    850                 855                 860

Gly Ser Leu Leu Gln Ile Pro Val Lys Ala Leu Lys Tyr Ser Gly Asp
865                 870                 875                 880

Pro Ser Ile Gly Asn Ile Ser Asp Glu Met Ala Lys Thr Ala Gln Trp
                885                 890                 895

Lys Ala Leu Ser Met Asn Thr Glu Asn Ala Lys Val Thr Arg Ser Asn
            900                 905                 910

Met Ser Pro Asp Lys Pro Val Ser Val Lys
        915                 920


<210> SEQ ID NO 42
<211> LENGTH: 364
<212> TYPE: PRT
<213> ORGANISM: Homo sapiens

<400> SEQUENCE: 42

Ile Asp Met Val Leu Asp Asn Met Ile Ala Ser Gly Gln Leu Asp Glu
  1               5                  10                  15

Ser Ile Arg Glu Asn Val Arg Glu Ala Leu Leu Lys Arg His His His
            20                  25                  30

Gln Asn Glu Lys Arg Phe Thr Ser Arg Ile Pro Leu Val Arg Ser Phe
        35                  40                  45

Ala Asp Ile Gly Lys Lys His Ser Asp Pro His Leu Leu Glu Arg Asn
    50                  55                  60

Gly Ile Leu Ala Ser Pro Gln Ser Ala Pro Gly Asn Leu Asp Asn Ser
 65                  70                  75                  80

Lys Ser Gly Glu Ile Lys Gly Asn Gly Ser Gly Gly Ser Arg Glu Asn
                85                  90                  95

Ser Thr Val Asp Phe Ser Lys Val Asp Met Asn Phe Met Arg Lys Ile
            100                 105                 110

Pro Thr Gly Ala Glu Ala Ser Asn Val Leu Val Gly Glu Val Asp Phe
        115                 120                 125

Leu Glu Arg Pro Ile Ile Ala Phe Val Arg Leu Ala Pro Ala Val Leu
    130                 135                 140

Leu Thr Gly Leu Thr Glu Val Pro Val Pro Thr Arg Phe Leu Phe Leu
145                 150                 155                 160

Leu Leu Gly Pro Ala Gly Lys Ala Pro Gln Tyr His Glu Ile Gly Arg
                165                 170                 175

Ser Ile Ala Thr Leu Met Thr Asp Glu Ile Phe His Asp Val Ala Tyr
            180                 185                 190

Lys Ala Lys Asp Arg Asn Asp Leu Leu Ser Gly Ile Asp Glu Phe Leu
        195                 200                 205

Asp Gln Val Thr Val Leu Pro Pro Gly Glu Trp Asp Pro Ser Ile Arg
    210                 215                 220

Ile Glu Pro Pro Lys Ser Val Pro Ser Gln Glu Lys Arg Lys Ile Pro
225                 230                 235                 240

Val Phe His Asn Gly Ser Thr Pro Thr Leu Gly Glu Thr Pro Lys Glu
                245                 250                 255

Ala Ala His His Ala Gly Pro Glu Leu Gln Arg Thr Gly Arg Leu Phe
            260                 265                 270

Gly Gly Leu Ile Leu Asp Ile Lys Arg Lys Ala Pro Phe Phe Leu Ser
```

-continued

```
        275                 280                 285

Asp Phe Lys Asp Ala Leu Ser Leu Gln Cys Leu Ala Ser Ile Leu Phe
    290                 295                 300

Leu Tyr Cys Ala Cys Met Ser Pro Val Ile Thr Phe Gly Gly Leu Leu
305                 310                 315                 320

Gly Glu Ala Thr Glu Gly Arg Ile Val Ser Thr Lys Ile Gly Ser Gly
                325                 330                 335

Gln Ala Phe Ser Ser Ser Glu Ala Ser Val Cys Met His Leu Ser His
            340                 345                 350

Tyr Ser Tyr Phe Tyr Leu Lys Ser Leu Pro Thr Ala
        355                 360


<210> SEQ ID NO 43
<211> LENGTH: 785
<212> TYPE: PRT
<213> ORGANISM: Homo sapiens

<400> SEQUENCE: 43

Cys Pro Ser Leu Asp Ile Arg Ser Glu Val Ala Glu Leu Arg Gln Leu
  1               5                  10                  15

Glu Asn Cys Ser Val Val Glu Gly His Leu Gln Ile Leu Leu Met Phe
             20                  25                  30

Thr Ala Thr Gly Glu Asp Phe Arg Gly Leu Ser Phe Pro Arg Leu Thr
        35                  40                  45

Gln Val Thr Asp Tyr Leu Leu Leu Phe Arg Val Tyr Gly Leu Glu Ser
     50                  55                  60

Leu Arg Asp Leu Phe Pro Asn Leu Ala Val Ile Arg Gly Thr Arg Leu
 65                  70                  75                  80

Phe Leu Gly Tyr Ala Leu Val Ile Phe Glu Met Pro His Leu Arg Asp
                 85                  90                  95

Val Ala Leu Pro Ala Leu Gly Ala Val Leu Arg Gly Ala Val Arg Val
            100                 105                 110

Glu Lys Asn Gln Glu Leu Cys His Leu Ser Thr Ile Asp Trp Gly Leu
        115                 120                 125

Leu Gln Pro Ala Pro Gly Ala Asn His Ile Val Gly Asn Lys Leu Gly
    130                 135                 140

Glu Glu Cys Ala Asp Val Cys Pro Gly Val Leu Gly Ala Ala Gly Glu
145                 150                 155                 160

Pro Cys Ala Lys Thr Thr Phe Ser Gly His Thr Asp Tyr Arg Cys Trp
                165                 170                 175

Thr Ser Ser His Cys Gln Arg Val Cys Pro Cys Pro His Gly Met Ala
            180                 185                 190

Cys Thr Ala Arg Gly Glu Cys Cys His Thr Glu Cys Leu Gly Gly Cys
        195                 200                 205

Ser Gln Pro Glu Asp Pro Arg Ala Cys Val Ala Cys Arg His Leu Tyr
    210                 215                 220

Phe Gln Gly Ala Cys Leu Trp Ala Cys Pro Pro Gly Thr Tyr Gln Tyr
225                 230                 235                 240

Glu Ser Trp Arg Cys Val Thr Ala Glu Arg Cys Ala Ser Leu His Ser
                245                 250                 255

Val Pro Gly Arg Ala Ser Thr Phe Gly Ile His Gln Gly Ser Cys Leu
            260                 265                 270

Ala Gln Cys Pro Ser Gly Phe Thr Arg Asn Ser Ser Ser Ile Phe Cys
        275                 280                 285
```

-continued

```
His Lys Cys Glu Gly Leu Cys Pro Lys Glu Cys Lys Val Gly Thr Lys
    290                 295                 300

Thr Ile Asp Ser Ile Gln Ala Ala Gln Asp Leu Val Gly Cys Thr His
305                 310                 315                 320

Val Glu Gly Ser Leu Ile Leu Asn Leu Arg Gln Gly Tyr Asn Leu Glu
                325                 330                 335

Pro Gln Leu Gln His Ser Leu Gly Leu Val Glu Thr Ile Thr Gly Phe
            340                 345                 350

Leu Lys Ile Lys His Ser Phe Ala Leu Val Ser Leu Gly Phe Phe Lys
        355                 360                 365

Asn Leu Lys Leu Ile Arg Gly Asp Ala Met Val Asp Gly Asn Tyr Thr
    370                 375                 380

Leu Tyr Val Leu Asp Asn Gln Asn Leu Gln Gln Leu Gly Ser Trp Val
385                 390                 395                 400

Ala Ala Gly Leu Thr Ile Pro Val Gly Lys Ile Tyr Phe Ala Phe Asn
                405                 410                 415

Pro Arg Leu Cys Leu Glu His Ile Tyr Arg Leu Glu Glu Val Thr Gly
            420                 425                 430

Thr Arg Gly Arg Gln Asn Lys Ala Glu Ile Asn Pro Arg Thr Asn Gly
        435                 440                 445

Asp Arg Ala Ala Cys Gln Thr Arg Thr Leu Arg Phe Val Ser Asn Val
    450                 455                 460

Thr Glu Ala Asp Arg Ile Leu Leu Arg Trp Glu Arg Tyr Glu Pro Leu
465                 470                 475                 480

Glu Ala Arg Asp Leu Leu Ser Phe Ile Val Tyr Tyr Lys Glu Ser Pro
                485                 490                 495

Phe Gln Asn Ala Thr Glu His Val Gly Pro Asp Ala Cys Gly Thr Gln
            500                 505                 510

Ser Trp Asn Leu Leu Asp Val Glu Leu Pro Leu Ser Arg Thr Gln Glu
        515                 520                 525

Pro Gly Val Thr Leu Ala Ser Leu Lys Pro Trp Thr Gln Tyr Ala Val
    530                 535                 540

Phe Val Arg Ala Ile Thr Leu Thr Thr Glu Glu Asp Ser Pro His Gln
545                 550                 555                 560

Gly Ala Gln Ser Pro Ile Val Tyr Leu Arg Thr Leu Pro Ala Ala Pro
                565                 570                 575

Thr Val Pro Gln Asp Val Ile Ser Thr Ser Asn Ser Ser Ser His Leu
            580                 585                 590

Leu Val Arg Trp Lys Pro Pro Thr Gln Arg Asn Gly Asn Leu Thr Tyr
        595                 600                 605

Tyr Leu Val Leu Trp Gln Arg Leu Ala Glu Asp Gly Asp Leu Tyr Leu
    610                 615                 620

Asn Asp Tyr Cys His Arg Gly Leu Arg Leu Pro Thr Ser Asn Asn Asp
625                 630                 635                 640

Pro Arg Phe Asp Gly Glu Asp Gly Asp Pro Glu Ala Glu Met Glu Ser
                645                 650                 655

Asp Cys Cys Pro Cys Gln His Pro Pro Pro Gly Gln Val Leu Pro Pro
            660                 665                 670

Leu Glu Ala Gln Glu Ala Ser Phe Gln Lys Lys Phe Glu Asn Phe Leu
        675                 680                 685

His Asn Ala Ile Thr Ile Pro Ile Ser Pro Trp Lys Val Thr Ser Ile
    690                 695                 700

Asn Lys Ser Pro Gln Arg Asp Ser Gly Arg His Arg Arg Ala Ala Gly
```

-continued

```
705                 710                 715                 720

Pro Leu Arg Leu Gly Gly Asn Ser Ser Asp Phe Glu Ile Gln Glu Asp
                725                 730                 735

Lys Val Pro Arg Glu Arg Ala Val Leu Ser Gly Leu Arg His Phe Thr
            740                 745                 750

Glu Tyr Arg Ile Asp Ile His Ala Cys Asn His Ala Ala His Thr Val
        755                 760                 765

Gly Cys Ser Ala Ala Thr Phe Val Phe Ala Arg Thr Met Pro His Ser
    770                 775                 780

Arg
785


<210> SEQ ID NO 44
<211> LENGTH: 131
<212> TYPE: PRT
<213> ORGANISM: Homo sapiens

<400> SEQUENCE: 44

Val Lys Cys Pro Gly Thr Xaa Cys Gln Thr Gly Phe Gly Ser Arg His
  1               5                  10                  15

Leu Val Ser Lys Lys Tyr Leu Phe Glu Tyr Thr Val Val Asn Val His
            20                  25                  30

Leu Ser Gln His His His Leu Leu Ala Leu Asp Val Cys Gly Gly Gly
        35                  40                  45

Leu Ile Pro Asn Pro His Ala Asp Ser Val His Pro Val Cys Cys Leu
     50                  55                  60

Ala Pro Ser Leu Pro Val Lys Leu Gln Thr Leu Arg Ile Trp Thr Ser
 65                  70                  75                  80

Arg Ser Val Val Leu Pro Pro Ser Thr Gly Leu Thr Gly Ala Ser Gly
                 85                  90                  95

His His Pro Ile Pro Ser Ser Thr Gly Ala Asn Ser Arg Cys Val Thr
            100                 105                 110

Val Ser Ala Cys Gly Leu Gly Ile Arg Pro Pro Pro Gln Thr Ser Arg
        115                 120                 125

Ala Arg Arg
    130


<210> SEQ ID NO 45
<211> LENGTH: 640
<212> TYPE: PRT
<213> ORGANISM: Homo sapiens

<400> SEQUENCE: 45

Ala Thr Gln Arg Leu Met Leu Thr Met Gly Arg Leu Gln Leu Val Val
  1               5                  10                  15

Leu Gly Leu Thr Cys Cys Trp Ala Val Ala Ser Ala Ala Lys Leu Gly
            20                  25                  30

Ala Val Tyr Thr Glu Gly Gly Phe Val Glu Gly Val Asn Lys Lys Leu
        35                  40                  45

Gly Leu Leu Gly Asp Ser Val Asp Ile Phe Lys Gly Ile Pro Phe Ala
     50                  55                  60

Ala Pro Thr Lys Ala Leu Glu Asn Pro Gln Pro His Pro Gly Trp Gln
 65                  70                  75                  80

Gly Thr Leu Lys Ala Lys Asn Phe Lys Lys Arg Cys Leu Gln Ala Thr
                 85                  90                  95

Ile Thr Gln Asp Ser Thr Tyr Gly Asp Glu Asp Cys Leu Tyr Leu Asn
```

-continued

```
            100                 105                 110

Ile Trp Val Pro Gln Gly Arg Lys Gln Val Ser Arg Asp Leu Pro Val
        115                 120                 125

Met Ile Trp Ile Tyr Gly Gly Ala Phe Leu Met Gly Ser Gly His Gly
    130                 135                 140

Ala Asn Phe Leu Asn Asn Tyr Leu Tyr Asp Gly Glu Glu Ile Ala Thr
145                 150                 155                 160

Arg Gly Asn Val Ile Val Val Thr Phe Asn Tyr Arg Val Gly Pro Leu
                165                 170                 175

Gly Phe Leu Ser Thr Gly Asp Ala Asn Leu Pro Gly Asn Tyr Gly Leu
            180                 185                 190

Arg Asp Gln His Met Ala Ile Ala Trp Val Lys Arg Asn Ile Ala Ala
        195                 200                 205

Phe Gly Gly Asp Pro Asn Asn Ile Thr Leu Phe Gly Glu Ser Ala Gly
    210                 215                 220

Gly Ala Ser Val Ser Leu Gln Thr Leu Ser Pro Tyr Asn Lys Gly Leu
225                 230                 235                 240

Ile Arg Arg Ala Ile Ser Gln Ser Gly Val Ala Leu Ser Pro Trp Val
                245                 250                 255

Ile Gln Lys Asn Pro Leu Phe Trp Ala Lys Lys Val Ala Glu Lys Val
            260                 265                 270

Gly Cys Pro Val Gly Asp Ala Ala Arg Met Ala Gln Cys Leu Lys Val
        275                 280                 285

Thr Asp Pro Arg Ala Leu Thr Leu Ala Tyr Lys Val Pro Leu Ala Gly
    290                 295                 300

Leu Glu Tyr Pro Met Leu His Tyr Val Gly Phe Val Pro Val Ile Asp
305                 310                 315                 320

Gly Asp Phe Ile Pro Ala Asp Pro Ile Asn Leu Tyr Ala Asn Ala Ala
                325                 330                 335

Asp Ile Asp Tyr Ile Ala Gly Thr Asn Asn Met Asp Gly His Ile Phe
            340                 345                 350

Ala Ser Ile Asp Met Pro Ala Ile Asn Lys Gly Asn Lys Lys Val Thr
        355                 360                 365

Glu Glu Asp Phe Tyr Lys Leu Val Ser Glu Phe Thr Ile Thr Lys Gly
    370                 375                 380

Leu Arg Gly Ala Lys Thr Thr Phe Asp Val Tyr Thr Glu Ser Trp Ala
385                 390                 395                 400

Gln Asp Pro Ser Gln Glu Asn Lys Lys Lys Thr Val Val Asp Phe Glu
                405                 410                 415

Thr Asp Val Leu Phe Leu Val Pro Thr Glu Ile Ala Leu Ala Gln His
            420                 425                 430

Arg Ala Asn Ala Lys Ser Ala Lys Thr Tyr Ala Tyr Leu Phe Ser His
        435                 440                 445

Pro Ser Arg Met Pro Val Tyr Pro Lys Trp Val Gly Ala Asp His Ala
    450                 455                 460

Asp Asp Ile Gln Tyr Val Phe Gly Lys Pro Phe Ala Thr Pro Thr Gly
465                 470                 475                 480

Tyr Arg Pro Gln Asp Arg Thr Val Ser Lys Ala Met Ile Ala Tyr Trp
                485                 490                 495

Thr Asn Phe Ala Lys Thr Gly Asp Pro Asn Met Gly Asp Ser Ala Val
            500                 505                 510

Pro Thr His Trp Glu Pro Tyr Thr Thr Glu Asn Ser Gly Tyr Leu Glu
        515                 520                 525
```

```
Ile Thr Lys Lys Met Gly Ser Ser Ser Met Lys Arg Ser Leu Arg Thr
    530                 535                 540

Asn Phe Leu Arg Tyr Trp Thr Leu Thr Tyr Leu Ala Leu Pro Thr Val
545                 550                 555                 560

Thr Asp Gln Glu Ala Thr Pro Val Pro Pro Thr Gly Asp Ser Glu Ala
                565                 570                 575

Thr Pro Val Pro Pro Thr Gly Asp Ser Glu Thr Ala Pro Val Pro Pro
            580                 585                 590

Thr Gly Asp Ser Gly Ala Pro Pro Val Pro Pro Thr Gly Asp Ser Gly
        595                 600                 605

Ala Pro Pro Val Pro Pro Thr Gly Asp Ser Gly Ala Pro Pro Val Pro
    610                 615                 620

Pro Thr Gly Asp Ser Lys Glu Ala Gln Met Pro Ala Val Ile Arg Phe
625                 630                 635                 640


<210> SEQ ID NO 46
<211> LENGTH: 659
<212> TYPE: PRT
<213> ORGANISM: Homo sapiens

<400> SEQUENCE: 46

Ala Thr Gln Arg Leu Met Leu Thr Met Gly Arg Leu Gln Leu Val Val
  1               5                  10                  15

Leu Gly Leu Thr Cys Cys Trp Ala Val Ala Ser Ala Ala Lys Leu Gly
            20                  25                  30

Ala Val Tyr Thr Glu Gly Gly Phe Val Glu Gly Val Asn Lys Lys Leu
        35                  40                  45

Gly Leu Leu Gly Asp Ser Val Asp Ile Phe Lys Gly Ile Pro Phe Ala
     50                  55                  60

Ala Pro Thr Lys Ala Leu Glu Asn Pro Gln Pro His Pro Gly Trp Gln
 65                  70                  75                  80

Gly Thr Leu Lys Ala Lys Asn Phe Lys Lys Arg Cys Leu Gln Ala Thr
                 85                  90                  95

Ile Thr Gln Asp Ser Thr Tyr Gly Asp Glu Asp Cys Leu Tyr Leu Asn
            100                 105                 110

Ile Trp Val Pro Gln Gly Arg Lys Gln Val Ser Arg Asp Leu Pro Val
        115                 120                 125

Met Ile Trp Ile Tyr Gly Gly Ala Phe Leu Met Gly Ser Gly His Gly
    130                 135                 140

Ala Asn Phe Leu Asn Asn Tyr Leu Tyr Asp Gly Glu Glu Ile Ala Thr
145                 150                 155                 160

Arg Gly Asn Val Ile Val Val Thr Phe Asn Tyr Arg Val Gly Pro Leu
                165                 170                 175

Gly Phe Leu Ser Thr Gly Asp Ala Asn Leu Pro Gly Asn Tyr Gly Leu
            180                 185                 190

Arg Asp Gln His Met Ala Ile Ala Trp Val Lys Arg Asn Ile Ala Ala
        195                 200                 205

Phe Gly Gly Asp Pro Asn Asn Ile Thr Leu Phe Gly Glu Ser Ala Gly
    210                 215                 220

Gly Ala Ser Val Ser Leu Gln Thr Leu Ser Pro Tyr Asn Lys Gly Leu
225                 230                 235                 240

Ile Arg Arg Ala Ile Ser Gln Ser Gly Val Ala Leu Ser Pro Trp Val
                245                 250                 255

Ile Gln Lys Asn Pro Leu Phe Trp Ala Lys Lys Val Ala Glu Lys Val
```

-continued

```
            260                 265                 270

Gly Cys Pro Val Gly Asp Ala Ala Arg Met Ala Gln Cys Leu Lys Val
        275                 280                 285

Thr Asp Pro Arg Ala Leu Thr Leu Ala Tyr Lys Val Pro Leu Ala Gly
    290                 295                 300

Leu Glu Tyr Pro Met Leu His Tyr Val Gly Phe Val Pro Val Ile Asp
305                 310                 315                 320

Gly Asp Phe Ile Pro Ala Asp Pro Ile Asn Leu Tyr Ala Asn Ala Ala
                325                 330                 335

Asp Ile Asp Tyr Ile Ala Gly Thr Asn Asn Met Asp Gly His Ile Phe
            340                 345                 350

Ala Ser Ile Asp Met Pro Ala Ile Asn Lys Gly Asn Lys Lys Val Thr
        355                 360                 365

Glu Glu Asp Phe Tyr Lys Leu Val Ser Glu Phe Thr Ile Thr Lys Gly
    370                 375                 380

Leu Arg Gly Ala Lys Thr Thr Phe Asp Val Tyr Thr Glu Ser Trp Ala
385                 390                 395                 400

Gln Asp Pro Ser Gln Glu Asn Lys Lys Lys Thr Val Val Asp Phe Glu
                405                 410                 415

Thr Asp Val Leu Phe Leu Val Pro Thr Glu Ile Ala Leu Ala Gln His
            420                 425                 430

Arg Ala Asn Ala Lys Ser Ala Lys Thr Tyr Ala Tyr Leu Phe Ser His
        435                 440                 445

Pro Ser Arg Met Pro Val Tyr Pro Lys Trp Val Gly Ala Asp His Ala
    450                 455                 460

Asp Asp Ile Gln Tyr Val Phe Gly Lys Pro Phe Ala Thr Pro Thr Gly
465                 470                 475                 480

Tyr Arg Pro Gln Asp Arg Thr Val Ser Lys Ala Met Ile Ala Tyr Trp
                485                 490                 495

Thr Asn Phe Ala Lys Thr Gly Asp Pro Asn Met Gly Asp Ser Ala Val
            500                 505                 510

Pro Thr His Trp Glu Pro Tyr Thr Thr Glu Asn Ser Gly Tyr Leu Glu
        515                 520                 525

Ile Thr Lys Lys Met Gly Ser Ser Ser Met Lys Arg Ser Leu Arg Thr
    530                 535                 540

Asn Phe Leu Arg Tyr Trp Thr Leu Thr Tyr Leu Ala Leu Pro Thr Val
545                 550                 555                 560

Thr Asp Gln Glu Ala Thr Pro Val Pro Pro Thr Gly Asp Ser Glu Ala
                565                 570                 575

Thr Pro Val Pro Pro Thr Gly Asp Ser Glu Thr Ala Pro Val Pro Pro
            580                 585                 590

Thr Gly Asp Ser Gly Ala Pro Pro Val Pro Pro Thr Gly Asp Ser Gly
        595                 600                 605

Ala Pro Pro Val Pro Pro Thr Gly Asp Ser Gly Ala Pro Pro Val Pro
    610                 615                 620

Pro Thr Gly Cys Pro Pro Arg Val Thr Leu Arg Leu Pro Leu Cys Pro
625                 630                 635                 640

Pro Gln Met Thr Pro Arg Lys Leu Arg Cys Leu Gln Ser Leu Gly Phe
                645                 650                 655

Ser Val Pro
```

<210> SEQ ID NO 47
<211> LENGTH: 381

<212> TYPE: PRT
<213> ORGANISM: Homo sapiens

<400> SEQUENCE: 47

```
Thr Ser Cys Ser Pro Gln Ile Pro Glu Ser Leu His Tyr Ile Ser Pro
  1               5                  10                  15

Val Gly His Pro Glu Ala Asp Ala His His Gly Ala Pro Ala Thr Gly
             20                  25                  30

Cys Val Gly Pro His Leu Leu Leu Gly Ser Gly Glu Cys Arg Glu Asp
         35                  40                  45

Pro Met Leu His Tyr Val Gly Phe Val Pro Val Ile Asp Gly Asp Phe
     50                  55                  60

Ile Pro Ala Asp Pro Ile Asn Leu Tyr Ala Asn Ala Ala Asp Ile Asp
 65                  70                  75                  80

Tyr Ile Ala Gly Thr Asn Asn Met Asp Gly His Ile Phe Ala Ser Ile
                 85                  90                  95

Asp Met Pro Ala Ile Asn Lys Gly Asn Lys Lys Val Thr Glu Glu Asp
            100                 105                 110

Phe Tyr Lys Leu Val Ser Glu Phe Thr Ile Thr Lys Gly Leu Arg Gly
        115                 120                 125

Ala Lys Thr Thr Phe Asp Val Tyr Thr Glu Ser Trp Ala Gln Asp Pro
    130                 135                 140

Ser Gln Glu Asn Lys Lys Lys Thr Val Val Asp Phe Glu Thr Asp Val
145                 150                 155                 160

Leu Phe Leu Val Pro Thr Glu Ile Ala Leu Ala Gln His Arg Ala Asn
                165                 170                 175

Ala Lys Ser Ala Lys Thr Tyr Ala Tyr Leu Phe Ser His Pro Ser Arg
            180                 185                 190

Met Pro Val Tyr Pro Lys Trp Val Gly Ala Asp His Ala Asp Asp Ile
        195                 200                 205

Gln Tyr Val Phe Gly Lys Pro Phe Ala Thr Pro Thr Gly Tyr Arg Pro
    210                 215                 220

Gln Asp Arg Thr Val Ser Lys Ala Met Ile Ala Tyr Trp Thr Asn Phe
225                 230                 235                 240

Ala Lys Thr Gly Asp Pro Asn Met Gly Asp Ser Ala Val Pro Thr His
                245                 250                 255

Trp Glu Pro Tyr Thr Thr Glu Asn Ser Gly Tyr Leu Glu Ile Thr Lys
            260                 265                 270

Lys Met Gly Ser Ser Ser Met Lys Arg Ser Leu Arg Thr Asn Phe Leu
        275                 280                 285

Arg Tyr Trp Thr Leu Thr Tyr Leu Ala Leu Pro Thr Val Thr Asp Gln
    290                 295                 300

Glu Ala Thr Pro Val Pro Pro Thr Gly Asp Ser Glu Ala Thr Pro Val
305                 310                 315                 320

Pro Pro Thr Gly Asp Ser Glu Thr Ala Pro Val Pro Pro Thr Gly Asp
                325                 330                 335

Ser Gly Ala Pro Pro Val Pro Pro Thr Gly Asp Ser Gly Ala Pro Pro
            340                 345                 350

Val Pro Pro Thr Gly Asp Ser Gly Ala Pro Pro Val Pro Pro Thr Gly
        355                 360                 365

Asp Ser Lys Glu Ala Gln Met Pro Ala Val Ile Arg Phe
    370                 375                 380
```

<210> SEQ ID NO 48

```
<211> LENGTH: 400
<212> TYPE: PRT
<213> ORGANISM: Homo sapiens

<400> SEQUENCE: 48

Thr Ser Cys Ser Pro Gln Ile Pro Glu Ser Leu His Tyr Ile Ser Pro
  1               5                  10                  15

Val Gly His Pro Glu Ala Asp Ala His His Gly Ala Pro Ala Thr Gly
             20                  25                  30

Cys Val Gly Pro His Leu Leu Leu Gly Ser Gly Glu Cys Arg Glu Asp
         35                  40                  45

Pro Met Leu His Tyr Val Gly Phe Val Pro Val Ile Asp Gly Asp Phe
     50                  55                  60

Ile Pro Ala Asp Pro Ile Asn Leu Tyr Ala Asn Ala Ala Asp Ile Asp
 65                  70                  75                  80

Tyr Ile Ala Gly Thr Asn Asn Met Asp Gly His Ile Phe Ala Ser Ile
                 85                  90                  95

Asp Met Pro Ala Ile Asn Lys Gly Asn Lys Lys Val Thr Glu Glu Asp
            100                 105                 110

Phe Tyr Lys Leu Val Ser Glu Phe Thr Ile Thr Lys Gly Leu Arg Gly
        115                 120                 125

Ala Lys Thr Thr Phe Asp Val Tyr Thr Glu Ser Trp Ala Gln Asp Pro
    130                 135                 140

Ser Gln Glu Asn Lys Lys Lys Thr Val Val Asp Phe Glu Thr Asp Val
145                 150                 155                 160

Leu Phe Leu Val Pro Thr Glu Ile Ala Leu Ala Gln His Arg Ala Asn
                165                 170                 175

Ala Lys Ser Ala Lys Thr Tyr Ala Tyr Leu Phe Ser His Pro Ser Arg
            180                 185                 190

Met Pro Val Tyr Pro Lys Trp Val Gly Ala Asp His Ala Asp Asp Ile
        195                 200                 205

Gln Tyr Val Phe Gly Lys Pro Phe Ala Thr Pro Thr Gly Tyr Arg Pro
    210                 215                 220

Gln Asp Arg Thr Val Ser Lys Ala Met Ile Ala Tyr Trp Thr Asn Phe
225                 230                 235                 240

Ala Lys Thr Gly Asp Pro Asn Met Gly Asp Ser Ala Val Pro Thr His
                245                 250                 255

Trp Glu Pro Tyr Thr Thr Glu Asn Ser Gly Tyr Leu Glu Ile Thr Lys
            260                 265                 270

Lys Met Gly Ser Ser Ser Met Lys Arg Ser Leu Arg Thr Asn Phe Leu
        275                 280                 285

Arg Tyr Trp Thr Leu Thr Tyr Leu Ala Leu Pro Thr Val Thr Asp Gln
    290                 295                 300

Glu Ala Thr Pro Val Pro Pro Thr Gly Asp Ser Glu Ala Thr Pro Val
305                 310                 315                 320

Pro Pro Thr Gly Asp Ser Glu Thr Ala Pro Val Pro Pro Thr Gly Asp
                325                 330                 335

Ser Gly Ala Pro Pro Val Pro Pro Thr Gly Asp Ser Gly Ala Pro Pro
            340                 345                 350

Val Pro Pro Thr Gly Asp Ser Gly Ala Pro Pro Val Pro Pro Thr Gly
        355                 360                 365

Cys Pro Pro Arg Val Thr Leu Arg Leu Pro Leu Cys Pro Pro Gln Met
    370                 375                 380

Thr Pro Arg Lys Leu Arg Cys Leu Gln Ser Leu Gly Phe Ser Val Pro
```

-continued

```
385                 390                 395                 400


<210> SEQ ID NO 49
<211> LENGTH: 503
<212> TYPE: PRT
<213> ORGANISM: Homo sapiens

<400> SEQUENCE: 49

Phe Gln Met Gly Lys Lys Ile Asn Lys Leu Phe Cys Phe Asn Phe Leu
  1               5                  10                  15

Val Gln Cys Phe Arg Gly Lys Ser Lys Pro Ser Lys Cys Gln Ile Arg
             20                  25                  30

Lys Lys Val Lys Asn His Ile Glu Arg Leu Leu Asp Thr Glu Asp Glu
        35                  40                  45

Leu Ser Asp Ile Gln Thr Asp Ser Val Pro Ser Glu Val Arg Asp Trp
     50                  55                  60

Leu Ala Ser Thr Phe Thr Arg Lys Met Gly Met Thr Lys Lys Lys Pro
 65                  70                  75                  80

Glu Glu Lys Pro Lys Phe Arg Ser Ile Val His Ala Val Gln Ala Gly
                 85                  90                  95

Ile Phe Val Glu Arg Met Tyr Arg Lys Thr Tyr His Met Val Gly Leu
            100                 105                 110

Ala Tyr Pro Ala Ala Val Ile Val Thr Leu Lys Asp Val Asp Lys Trp
        115                 120                 125

Ser Phe Asp Val Phe Ala Leu Asn Glu Ala Ser Gly Glu His Ser Leu
    130                 135                 140

Lys Phe Met Ile Tyr Glu Leu Phe Thr Arg Tyr Asp Leu Ile Asn Arg
145                 150                 155                 160

Phe Lys Ile Pro Val Ser Cys Leu Ile Thr Phe Ala Glu Ala Leu Glu
                165                 170                 175

Val Gly Tyr Ser Lys Tyr Lys Asn Pro Tyr His Asn Leu Ile His Ala
            180                 185                 190

Ala Asp Val Thr Gln Thr Val His Tyr Ile Met Leu His Thr Gly Ile
        195                 200                 205

Met His Trp Leu Thr Glu Leu Glu Ile Leu Ala Met Val Phe Ala Ala
    210                 215                 220

Ala Ile His Asp Tyr Glu His Thr Gly Thr Thr Asn Asn Phe His Ile
225                 230                 235                 240

Gln Thr Arg Ser Asp Val Ala Ile Leu Tyr Asn Asp Arg Ser Val Leu
                245                 250                 255

Glu Asn His His Val Ser Ala Ala Tyr Arg Leu Met Gln Glu Glu Glu
            260                 265                 270

Met Asn Ile Leu Ile Asn Leu Ser Lys Asp Asp Trp Arg Asp Leu Arg
        275                 280                 285

Asn Leu Val Ile Glu Met Val Leu Ser Thr Asp Met Ser Gly His Phe
    290                 295                 300

Gln Gln Ile Lys Asn Ile Arg Asn Ser Leu Gln Gln Pro Glu Gly Ile
305                 310                 315                 320

Asp Arg Ala Lys Thr Met Ser Leu Ile Leu His Ala Ala Asp Ile Ser
                325                 330                 335

His Pro Ala Lys Ser Trp Lys Leu His Tyr Arg Trp Thr Met Ala Leu
            340                 345                 350

Met Glu Glu Phe Phe Leu Gln Gly Asp Lys Glu Ala Glu Leu Gly Leu
        355                 360                 365
```

-continued

Pro Phe Ser Pro Leu Cys Asp Arg Lys Ser Thr Met Val Ala Gln Ser
370 375 380

Gln Ile Gly Phe Ile Asp Phe Ile Val Glu Pro Thr Phe Ser Leu Leu
385 390 395 400

Thr Asp Ser Thr Glu Lys Ile Val Ile Pro Leu Ile Glu Glu Ala Ser
405 410 415

Lys Ala Glu Thr Ser Ser Tyr Val Ala Ser Ser Ser Thr Thr Ile Val
420 425 430

Gly Leu His Ile Ala Asp Ala Leu Arg Arg Ser Asn Thr Lys Gly Ser
435 440 445

Met Ser Asp Gly Ser Tyr Ser Pro Asp Tyr Ser Leu Ala Ala Val Asp
450 455 460

Leu Lys Ser Phe Lys Asn Asn Leu Val Asp Ile Ile Gln Gln Asn Lys
465 470 475 480

Glu Arg Trp Lys Glu Leu Ala Ala Gln Glu Ala Arg Thr Ser Ser Gln
485 490 495

Lys Cys Glu Phe Ile His Gln
500

<210> SEQ ID NO 50
<211> LENGTH: 612
<212> TYPE: PRT
<213> ORGANISM: Homo sapiens

<400> SEQUENCE: 50

Leu Pro Leu Leu His Ala Gly Phe Asn Arg Arg Phe Met Glu Asn Ser
1 5 10 15

Ser Ile Ile Ala Cys Tyr Asn Glu Leu Ile Gln Ile Glu His Gly Glu
20 25 30

Val Arg Ser Gln Phe Lys Leu Arg Ala Cys Asn Ser Val Phe Thr Ala
35 40 45

Leu Asp His Cys His Glu Ala Ile Glu Ile Thr Ser Asp Asp His Val
50 55 60

Ile Gln Glu Trp Gln Gly Val Tyr Tyr Ala Arg Arg Lys Ser Gly Asp
65 70 75 80

Ser Ile Gln Gln His Val Lys Ile Thr Pro Val Ile Gly Gln Gly Gly
85 90 95

Lys Ile Arg His Phe Val Ser Leu Lys Lys Leu Cys Cys Thr Thr Asp
100 105 110

Asn Asn Lys Gln Ile His Lys Ile His Arg Asp Ser Gly Asp Asn Ser
115 120 125

Gln Thr Glu Pro His Ser Phe Arg Tyr Lys Asn Arg Arg Lys Glu Ser
130 135 140

Ile Asp Val Lys Ser Ile Ser Ser Arg Gly Ser Asp Ala Pro Ser Leu
145 150 155 160

Gln Asn Arg Arg Tyr Pro Ser Met Ala Arg Ile His Ser Met Thr Ile
165 170 175

Glu Ala Pro Ile Thr Lys Val Ile Asn Ile Ile Asn Ala Ala Gln Glu
180 185 190

Asn Ser Pro Val Thr Val Ala Glu Ala Leu Asp Arg Val Leu Glu Ile
195 200 205

Leu Arg Thr Thr Glu Leu Tyr Ser Pro Gln Leu Gly Thr Lys Asp Glu
210 215 220

Asp Pro His Thr Ser Asp Leu Val Gly Gly Leu Met Thr Asp Gly Leu
225 230 235 240

```
Arg Arg Leu Ser Gly Asn Glu Tyr Val Phe Thr Lys Asn Val His Gln
                245                 250                 255

Ser His Ser His Leu Ala Met Pro Ile Thr Ile Asn Asp Val Pro Pro
            260                 265                 270

Cys Ile Ser Gln Leu Leu Asp Asn Glu Glu Ser Trp Asp Phe Asn Ile
        275                 280                 285

Phe Glu Leu Glu Ala Ile Thr His Lys Arg Pro Leu Val Tyr Leu Gly
    290                 295                 300

Leu Lys Val Phe Ser Arg Phe Gly Val Cys Glu Phe Leu Asn Cys Ser
305                 310                 315                 320

Glu Thr Thr Leu Arg Ala Trp Phe Gln Val Ile Glu Ala Asn Tyr His
                325                 330                 335

Ser Ser Asn Ala Tyr His Asn Ser Thr His Ala Ala Asp Val Leu His
            340                 345                 350

Ala Thr Ala Phe Phe Leu Gly Lys Glu Arg Val Lys Gly Ser Leu Asp
        355                 360                 365

Gln Leu Asp Glu Val Ala Ala Leu Ile Ala Ala Thr Val His Asp Val
    370                 375                 380

Asp His Pro Gly Arg Thr Asn Ser Phe Leu Cys Asn Ala Gly Ser Glu
385                 390                 395                 400

Leu Ala Val Leu Tyr Asn Asp Thr Ala Val Leu Glu Ser His His Thr
                405                 410                 415

Ala Leu Ala Phe Gln Leu Thr Val Lys Asp Thr Lys Cys Asn Ile Phe
            420                 425                 430

Lys Asn Ile Asp Arg Asn His Tyr Arg Thr Leu Arg Gln Ala Ile Ile
        435                 440                 445

Asp Met Val Leu Ala Thr Glu Met Thr Lys His Phe Glu His Val Asn
    450                 455                 460

Lys Phe Val Asn Ser Ile Asn Lys Pro Met Ala Ala Glu Ile Glu Gly
465                 470                 475                 480

Ser Asp Cys Glu Cys Asn Pro Ala Gly Lys Asn Phe Pro Glu Asn Gln
                485                 490                 495

Ile Leu Ile Lys Arg Met Met Ile Lys Cys Ala Asp Val Ala Asn Pro
            500                 505                 510

Cys Arg Pro Leu Asp Leu Cys Ile Glu Trp Ala Gly Arg Ile Ser Glu
        515                 520                 525

Glu Tyr Phe Ala Gln Thr Asp Glu Glu Lys Arg Gln Gly Leu Pro Val
    530                 535                 540

Val Met Pro Val Phe Asp Arg Asn Thr Cys Ser Ile Pro Lys Ser Gln
545                 550                 555                 560

Ile Ser Phe Ile Asp Tyr Phe Ile Thr Asp Met Phe Asp Ala Trp Asp
                565                 570                 575

Ala Phe Ala His Leu Pro Ala Leu Met Gln His Leu Ala Asp Asn Tyr
            580                 585                 590

Lys His Trp Lys Thr Leu Asp Asp Leu Lys Cys Lys Ser Leu Arg Leu
        595                 600                 605

Pro Ser Asp Ser
    610
```

<210> SEQ ID NO 51
<211> LENGTH: 218
<212> TYPE: PRT
<213> ORGANISM: Homo sapiens

```
<400> SEQUENCE: 51

Lys Tyr Ser Asn Asn Ser Trp Arg Tyr Leu Ser Asn Arg Leu Leu Ala
  1               5                  10                  15

Pro Ser Asp Ser Pro Glu Trp Leu Ser Phe Asp Val Thr Gly Val Val
             20                  25                  30

Arg Gln Trp Leu Ser Arg Gly Gly Glu Ile Glu Gly Phe Arg Leu Ser
         35                  40                  45

Ala His Cys Ser Cys Asp Ser Arg Asp Asn Thr Leu Gln Val Asp Ile
     50                  55                  60

Asn Gly Phe Thr Thr Gly Arg Arg Gly Asp Leu Ala Thr Ile His Gly
 65                  70                  75                  80

Met Asn Arg Pro Phe Leu Leu Leu Met Ala Thr Pro Leu Glu Arg Ala
                 85                  90                  95

Gln His Leu Gln Ser Ser Arg His Arg Arg Ala Leu Asp Thr Asn Tyr
            100                 105                 110

Cys Phe Ser Ser Thr Glu Lys Asn Cys Cys Val Arg Gln Leu Tyr Ile
        115                 120                 125

Asp Phe Arg Lys Asp Leu Gly Trp Lys Trp Ile His Glu Pro Lys Gly
    130                 135                 140

Tyr His Ala Asn Phe Cys Leu Gly Pro Cys Pro Tyr Ile Trp Ser Leu
145                 150                 155                 160

Asp Thr Gln Tyr Ser Lys Val Leu Ala Leu Tyr Asn Gln His Asn Pro
                165                 170                 175

Gly Ala Ser Ala Ala Pro Cys Cys Val Pro Gln Ala Leu Glu Pro Leu
            180                 185                 190

Pro Ile Val Tyr Tyr Val Gly Arg Lys Pro Lys Val Glu Gln Leu Ser
        195                 200                 205

Asn Met Ile Val Arg Ser Cys Lys Cys Ser
    210                 215


<210> SEQ ID NO 52
<211> LENGTH: 185
<212> TYPE: PRT
<213> ORGANISM: Homo sapiens

<400> SEQUENCE: 52

Lys Tyr Ser Asn Asn Ser Trp Arg Tyr Leu Ser Asn Arg Leu Leu Ala
  1               5                  10                  15

Pro Ser Asp Ser Pro Glu Trp Leu Ser Phe Asp Val Thr Gly Val Val
             20                  25                  30

Arg Gln Trp Leu Ser Arg Gly Gly Glu Ile Glu Gly Phe Arg Leu Ser
         35                  40                  45

Ala His Cys Ser Cys Asp Ser Arg Asp Asn Thr Leu Gln Val Asp Ile
     50                  55                  60

Asn Gly Phe Thr Thr Gly Arg Arg Gly Asp Leu Ala Thr Ile His Gly
 65                  70                  75                  80

Met Asn Arg Pro Phe Leu Leu Leu Met Ala Thr Pro Leu Glu Arg Ala
                 85                  90                  95

Gln His Leu Gln Ser Ser Arg His Arg Arg Ala Leu Asp Thr Asn Tyr
            100                 105                 110

Cys Phe Ser Ser Thr Glu Lys Asn Cys Cys Val Arg Gln Leu Tyr Ile
        115                 120                 125

Asp Phe Arg Lys Asp Leu Gly Trp Lys Trp Ile His Glu Pro Lys Gly
    130                 135                 140
```

-continued

```
Tyr His Ala Asn Phe Cys Leu Gly Pro Cys Pro Tyr Ile Trp Ser Leu
145                 150                 155                 160

Asp Thr Gln Tyr Ser Lys Leu Asn Glu Gln Asn Leu Ile Gln Glu Val
                165                 170                 175

Pro Asn Ile Trp Gln Arg Glu Val Gly
            180                 185
```

ALTERNATIVE SPLICE VARIANTS OF CD40

This application claims priority of Application No. 129907 filed in Israel on May 12, 1999, under 35 U.S.C. §119.

FIELD OF THE INVENTION

The present invention concerns novel nucleic acid sequences, vectors and host cells containing them, amino acid sequences encoded by said sequences, and antibodies reactive with said amino acid sequences, as well as pharmaceutical compositions comprising any of the above. The present invention further concerns methods for screening for candidate activator or deactivators utilizing said amino acid sequences.

BACKGROUND OF THE INVENTION

Alternative splicing (AS) is an important regulatory mechanism in higher eukaryotes (P. A. Sharp, *Cell* 77, 805–8152 (1994). It is thought to be one of the important mechanisms for differential expression related to tissue or development stage specificity. It is known to play a major role in numerous biological systems, including human antibody responses, sex determination in Drosophila, and and and (S. Stamm, M. Q. Zhang, T. G. Marr and D. M. Helfman, *Nucleic Acids Research* 22, 1515–1526 (1994); B. Chabot, Trends Genet. 12, 472–478 (1996); R. E. Breitbart, A. Andreadis, B. Nadal-Ginard, *Annual Rev. Biochem*., 56, 467–495 (1987); C. W. Smith, J. G. Patton, B. Nadal-Ginard, *Annu. Rev. Genet*., 27, 527–577 (1989).

Until recently it was commonly believed that alternative splicing existed in only a small fraction of genes (about 5%). A recent observation based on literature survey of known genes revises this estimate to as high as stating that at least 30% of human genes are alternatively spliced (M. S. Gelfand, I. Dubchak, I. Draluk and M. Zorn, *Nucleic Acids Research* 27, 301–302 (1999). The importance of the actual frequency of this phenomenon lies not only in the direct impact on the number of proteins created (100,000 human genes, for example, would be translated to a much higher number of proteins), but also in the diversity of functionality derived from the process.

Several mechanisms at different stages may be held responsible for the complexity of higher eukaryote which include: alternative splicing at the transcription level, RNA editing at the post-transcriptional level, and post-translational modifications are the ones characterized to date.

GLOSSARY

In the following description and claims use will be made, at times, with a variety of terms, and the meaning of such terms as they should be construed in accordance with the invention is as follows:

"Variant nucleic acid sequence"—the sequence shown in any one of SEQ ID NO: 1 to SEQ ID NO: 26, sequences having at least 90% identity (see below) to said sequence and fragments (see below) of the above sequences of least 20 b.p. long. These sequences are sequences coding for a novel, naturally occurring, alternative splice variant of the native and known genes. It should be emphasized that the novel variants of the present invention are naturally occurring sequences resulting from alternative splicing of genes and not merely truncated, mutated or fragmented forms of known sequences.

"Variant product—also referred at times as the "variant protein" or "variant plypeptide"—is an amino acid sequence encoded by the variant nucleic acid sequence which is a naturally occurring mRNA sequence obtained as a result of alternative splicing. The amino acid sequence may be a peptide, a protein, as well as peptides or proteins having chemically modified amino acids (see below) such as a glycopeptide or glycoprotein. The variant products are shown in any one of SEQ ID NO: 27 to SEQ ID NO: 52. The term also includes homologies (see below) of said sequences in which one or more amino acids has been added, deleted, substituted (see below) or chemically modified (see below) as well as fragments (see below) of this sequence having at least 10 amino acids.

"Nucleic acid sequence"—a sequence composed of DNA nucleotides, RNA nucleotides or a combination of both types and may includes natural nucleotides, chemically modified nucleotides and synthetic nucleotides.

"Amino acid sequence"—a sequence composed of any one of the 20 naturally appearing amino acids, amino acids which have been chemically modified (see below), or composed of synthetic amino acids.

"Fragment of variant nucleic acid sequence"—novel short stretch of nucleic acid sequences of at least 20 b.p., which does not appear as a continuous stretch in the original nucleic acid sequence (see below). The fragment may be a sequence which was previously undescribed in the context of the published RNA and which affects the amino acid sequence encoded by the known gene. For example, where the variant nucleic includes a sequence which was not included in the original sequence (a sequence but which was an intron in the original sequence) the fragment is that additional sequence. The fragment may also be a region which is not an intron, which was not present in the original sequence. Another example is when the variant lacks a non-terminal region which was present in the original sequence. The two stretches of nucleotides spanning this region (upstream and downstream) are brought together by splicing in the variant, but are spaced from each by the region in the original sequence and are thus not continuous. A continuous stretch of nucleic acids comprising said two sparing stretches of nucleotides is not present in the original sequence and thus falls under the definition of fragment.

"Fragments of variant products"—novel amino acid sequences coded by the "fragment of variant nucleic acid sequence" defined above.

"Homologues of variants"—amino acid sequences of variants in which one or more amino acids has been added, deleted or replaced. The addition, deletion or replacement should be in regions or adjacent to regions where the variant differs from the original sequence (see below).

"Conservative substitution"—refers to the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. [Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

"Non-conservative substitution"—refers to the substitution of an amino acid in one class with an amino acid from another class; for example, substitution of an Ala, a class II residue, with a class III residue such as Asp, Asn, Glu, or Gln.

"Chemically modified"—when referring to the product of the invention, means a product (protein) where at least one of its amino acid resides is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristlyation, pegylation, prenylation, phosphorylation, ubiqutination, or any similar process.

"Biologically active"—refers to the variant product having some sort of biological activity, for example, some physiologically measurable effect on target cells, molecules or tissues.

"Immunologically active" defines the capability of a natural, recombinant or synthetic varient product, or any fragment thereof, to induce a specific immune response in appropriate animals or cells and to bind with specific antibodies. Thus, for example, an immunologically active fragment of variant product denotes a fragment which retains some or all of the immunological properties of the variant product, e.g can bind specific anti-variant product antibodies or which can elicit an immune response which will generate such antibodies or cause proliferation of specific immune cells which produce variant.

"Optimal alignment"—is defined as an alignment giving the highest percent identity score. Such alignment can be performed using a variety of commercially available sequence analysis programs, such as the local alignment program LALIGN using a ktup of 1, default parameters and the default PAM. A preferred alignment is the one performed using the CLUSTAL-W program from MacVector (TM), operated with an open gap penalty of 10.0, an extended gap penalty of 0.1, and a BLOSUM similarity matrix. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence). In case of alignments of known gene sequences with that of the new variant, the optimal alignment invariably included aligning the identical parts of both sequences together, then keeping apart and unaligned the sections of the sequences that differ one from the other.

"Having at least 90% identity"—with respect to two amino acid or nucleic acid sequence sequences, refers to the percentage of residues that are identical in the two sequences when the sequences are optimally aligned. Thus, 90% amino acid sequence identity means that 90% of the amino acids in two or more optimally aligned polypeptide sequences are identical, however this definition explicitly excludes sequences which are 100% identical with the original sequence from which the variant of the invention was varied.

"Isolated nucleic acid molecule having an variant nucleic acid sequence"—is a nucleic acid molecule that includes the coding variant nucleic acid sequence. Said isolated nucleic acid molecule may include the variant nucleic acid sequence as an independent insert; may include the variant nucleic acid sequence fused to an additional coding sequences, encoding together a fusion protein in which the variant coding sequence is the dominant coding sequence (for example, the additional coding sequence may code for a signal peptide); the variant nucleic acid sequence may be in combination with non-coding sequences, e.g., introns or control elements, such as promoter and terminator elements or 5' and/or 3' untranslated regions, effective for expression of the coding sequence in a suitable host; or may be a vector in which the variant protein coding sequence is a heterologous.

"Expression vector"—refers to vectors that have the ability to incorporate and express heterologous DNA fragments in a foreign cell. Many prokaryotic and eukaryotic expression vectors are known and/or commercially available. Selection of appropriate expression vectors is within the knowledge of those having skill in the art.

"Deletion"—is a change in either nucleotide or amino acid sequence in which one or more nucleotides or amino acid residues, respectively, are absent.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively. As regards amino acid sequences the substitution may be conservative or non-conservative.

"Antibody"—refers to IgG, IgM, IgD, IgA, and IgG antibody. The definition includes polyclonal antibodies or monoclonal antibodies. This term refers to whole antibodies or fragments of the antibodies comprising the antigen-binding domain of the anti-variant product antibodies, e.g. antibodies without the Fc portion, single chain antibodies, fragments consisting of essentially only the variable, antigen-binding domain of the antibody, etc.

"Activator"—as used herein, refers to a molecule which mimics the effect of the natural variant product or at times even increases or prolongs the duration of the biological activity of said product, as compared to that induced by the natural product. The mechanism may be by any mechanism known to prolonging activities of biological molecules such as binding to receptors; prolonging the lifetime of the molecules; increasing the activity of the molecules on its target; increasing the affinity of molecules to its receptor; inhibiting degradation or proteolysis of the molecules, etc. Activators may be polypeptides, nucleic acids, carbohydrates, lipids, or derivatives thereof, or any other molecules which can bind to and activate the variant product.

"Deactivator" or ("Inhibitor") refers to a molecule which modulates the activity of the variant product in an opposite manner to that of the activator, by decreasing or shortening the duration of the biological activity of the variant product. This may be done by any mechanism known to deactivate or inhibit biological molecules such as block of the receptor, block of active site, competition on binding site in target, enhancement of degradation, etc. Deactivators may be polypeptides, nucleic acids, carbohydrates, lipids, or derivatives thereof, or any other molecules which bind to and modulate the activity of said product.

"Treating a disease"—refers to administering a therapeutic substance effective to ameliorate symptoms associated with a disease, to lessen the severity or cure the disease, or to prevent the disease from occurring.

"Detection"—refers to a method of detection of a disease, disorder, pathological or normal condition. This term may refer to detection of a predisposition to a disease as well as for establishing the prognosis of the patient by determining the severity of the disease.

"Probe"—the variant nucleic acid sequence, or a sequence complementary therewith, when used to detect presence of other similar sequences in a sample. The detection is carried out by identification of hybridization complexes between the probe and the assayed sequence. The probe may be attached to a solid support or to a detectable label.

"Original sequence"—the amino acid or nucleic acid sequence from which the variant of the invention have been varied as a result of alternative slicing.

SUMMARY OF THE INVENTION

The present invention is based on the finding of several novel, naturally occurring splice variants, which are naturally occurring sequences obtained by alternative splicing of known genes. The novel splice variants of the invention are not merely truncated forms, fragments or mutations of known genes, but rather novel sequences which naturally occur within the body of individuals.

The term "alternative splicing" in the context of the present invention and claims refers to: intron inclusion, exon exclusion, addition or deletion of terminal sequences in the variant as compared to the original sequences, as well as to the possibility of "intron retention". Intron retention is an intermediate stage in the processing of RNA transcripts, where prior to production of fully processed mRNA the intron (naturally spliced in the original sequence) is retained in the variant. These intermediately processed RNAs may have physiological significance and are also within the scope of the invention.

The novel variant products of the invention may have the same physiological activity as the original peptide from which they are varied (although perhaps at a different level); may have an opposite physiological activity from the activity featured by the original peptide from which they are varied; may have a completely different, unrelated activity to the activity of the original from which they are varied; or alternatively may have no activity at all and this may lead to various diseases or pathological conditions.

The novel variants may also serve for detection purposes, i.e. their presence or level may be indicative of a disease, disorder, pathological or normal condition or alternatively the ratio between the level variants and the level original peptide from which they were varied, or the ratio to other variants may be indicative to a disease, disorder, pathological or normal condition.

For example, for detectional purposes, it is possible to establish differential expression of various variants in various tissues. A certain variant may be expressed mainly in one tissue, while the original sequence from which it has been varied, or another variant may, be expressed mainly in another tissue. Understanding of the distribution of the variants in various tissues may be helpful in basic research, for understanding the physiological function of the genes as well as may help in targeting pharmaceuticals or developing pharmaceuticals.

The study of the variants may also be helpful to distinguish various stages in the life cycles of the same type of cells which may also be helpful for development of pharmaceuticals for various pathological conditions in which cell cycles is un-normal, notably cancer.

Thus the detection may by determination of the presence or the level of expression of the variant within a specific cell population, comprising said presence or level between various cell types in a tissue, between different tissues and between individuals.

Thus the present invention provides by its first aspect, a novel isolated nucleic acid molecule comprising or consisting of any one of the coding sequence SEQ ID NO: 1 to SEQ ID NO: 26, fragments of said coding sequence having at least 20 nucleic acids (provided that said fragments are continuous stretches of nucleotides not present in the original sequence from which the variant was varied), or a molecule comprising a sequence having at least 90%, identity to SEQ ID NO: 1 to SEQ ID NO: 26, provided that the molecule is not completely identical to the original sequence from which the variant was varied.

The present invention further provides a protein or polypeptide comprising or consisting of an amino acid sequence encoded by any of the above nucleic acid sequences, termed herein "variant product", for example, an amino acid sequence having the sequence as depicted in any one of SEQ ID NO: 27 to SEQ ID NO: 52, fragments of the above amino acid sequence having a length of at least 10 amino acids coded by the above fragments of the nucleic acid sequences, as well as homologues of the above amino acid sequences in which one or more of the amino acid residues has been substituted (by conservative or non-conservative substitution) added, deleted, or chemically modified.

The deletions, insertions and modifications should be in regions, or adjacent to regions, wherein the variant differs from the original sequence.

For example, where the variant is different from the original sequence by addition of a short stretch of 10 amino acids, in the terminal or non-terminal portion of the peptide, the invention also concerns homologues of that variant where the additional short stretch is altered for example, it includes only 8 additional amino acids, includes 13 additional amino acids, or it includes 10 additional amino acids, however some of them being conservative or non-conservative substitutes of the original additional 10 amino acids of the novel variants. In all cases the changes in the homolog, as compared to the original sequence, are in the same regions where the variant differs from the original sequence, or in regions adjacent to said region.

Another example is where the variant lacks a non-terminal region (for example of 20 amino acids) which is present in the original sequence (due for example to exon exclusion). The homologues may lack in the same region only 17 amino acids or 23 amino acids. Again the deletion is in the same region where the variant lacks a sequence as compared to the original sequence, or in a region adjacent thereto.

It should be appreciated that once a man versed in the art's attention is directed to the importance of a specific region, due to the fact that this region differs in the variant as compared to the original sequence, there is no problem in derivating said specific region by addition to it, deleting from it, or substituting some amino acids in it. Thus homologues of variants which are derivated from the variant by changes (deletion, addition, substitution) only in said region as well as in regions adjacent to it are also a part of the present invention. Generally, if the variant is distinguished from the original sequence by some sort of physiological activity, then the homolog is distinguished from the original sequence in essentially the same manner.

The present invention further provides nucleic acid molecule comprising or consisting of a sequence which encodes the above amino acid sequences, (including the fragments and homologues of the amino acid sequences). Due to the degenerative nature of the genetic code, a plurality of alternative nucleic acid sequences, beyond those depicted in any one of SEQ ID NO: 1 to SEQ ID NO: 26, can code for the amino acid sequence of the invention. Those alternative nucleic acid sequences which code for the same amino acid sequences codes by the sequence SEQ ID NO: 27 to SEQ ID NO: 52 are also an aspect of the of the present invention.

The present invention further provides expression vectors and cloning vectors comprising any of the above nucleic acid sequences, as well as host cells transfected by said vectors.

The present invention still further provides pharmaceutical compositions comprising, as an active ingredient, said nucleic acid molecules, said expression vectors, or said protein or polypeptide.

These pharmaceutical compositions are suitable for the treatment of diseases and pathological conditions, which can be ameliorated or cured by raising the level of any one of the variant products of the invention.

By a second aspect, the present invention provides a nucleic acid molecule comprising or consisting of a non-coding sequence which is complementary to that of any one of SEQ ID NO: 1 to SEQ ID NO: 26, or complementary to a sequence having at least 90% identity to said sequence (with the proviso added above) or a fragment of said two sequences (according to the above definition of fragment). The complementary sequence may be a DNA sequence which hybridizes with any one of SEQ of ID NO: 1 to SEQ ID NO: 26 or hybridizes to a portion of that sequence having a length sufficient to inhibit the transcription of the complementary sequence. The complementary sequence may be a DNA sequence which can be transcribed into an mRNA being an antisense to the mRNA transcribed from any one of SEQ ID NO: 1 to SEQ ID NO: 26 or into an mRNA which is an antisense to a fragment of the mRNA transcribed from any one of SEQ ID NO: 1 to SEQ ID NO: 26 which has a length sufficient to hybridize with the mRNA transcribed from SEQ ID NO: 1 to SEQ ID NO: 26, so as to inhibit its translation. The complementary sequence may also be the mRNA or the fragment of the mRNA itself.

The nucleic acids of the second aspect of the invention may be used for therapeutic or diagnostic applications for example as probes used for the detection of the variants of the invention. The presence of the variant transcript or the level of the variant transcript may be indicative of a multitude of diseases, disorders and various pathological as well as normal conditions. In addition, the ratio of the level of the transcripts of the variants of the invention may also be compared to that of the transcripts of the original sequences from which they were varied, or to the level of transcript of other variants, and said ratio may be indicative to a multitude of diseases, disorders and various pathological and normal conditions.

The present invention also provides expression vectors comprising any one of the above defined complementary nucleic acid sequences and host cells transfected with said nucleic acid sequences or vectors, being complementary to those specified in the first aspect of the invention.

The invention also provides anti-variant product antibodies, namely antibodies directed against the variant product which specifically bind to said variant product. Said antibodies are useful both for diagnostic and therapeutic purposes. For example said antibodies may be as an active ingredient in a pharmaceutical composition as will be explained below.

By another alternative, the invention concerns antibodies termed “distinguishing antibodies” which are directed solely to the amino acid sequences which distinguishes the variant from the original amino acid sequence from which it has been varied by alternative splicing. For example, where the variant contains additional amino acids as compared to the original sequence (due to intron inclusion) the antibodies may be directed against these additional amino acids (present in the variant and not present in the original sequence). Another example is where the variant lacks 20 amino acids as compared to the original sequence from which it is varied (for example due to exon exclusion). The distinguishing antibodies in that case may be directed only against these 20 amino acids which are present in the original sequence and absent from the variant sequence.

The distinguishing antibodies may be used for detection purposes, i.e. to detect individuals, tissue, conditions (both pathological or physiological) wherein the variant sequence or original sequence are evident or abundant. The antibodies may also be used to distinguish conditions where the level, or ratio of the variant to original sequence is altered.

The distinguishing antibodies may also be used for therapeutical purposes, i.e., to neutralize only the variant product or only the product of the original sequence, as the case may be, without neutralizing the other.

The present invention also provides pharmaceutical compositions comprising, as an active ingredient, the nucleic acid molecules which comprise or consist of said complementary sequences, or of a vector comprising said complementary sequences. The pharmaceutical composition thus provides pharmaceutical compositions comprising, as an active ingredient, said anti-variant product antibodies.

The pharmaceutical compositions comprising said anti-variant product antibodies or the nucleic acid molecule comprising said complementary sequence, are suitable for the treatment of diseases and pathological conditions where a therapeutically beneficial effect may be achieved by neutralizing the variant (either at the transcript or product level) or decreasing the amount of the variant product or blocking its binding to its target, for example, by the neutralizing effect of the antibodies, or by the decrease of the effect of the antisense mRNA in decreasing expression level of the variant product.

According to the third aspect of the invention the present invention provides methods for detecting the level of the transcript (mRNA) of said variant product in a body fluid sample, or in a specific tissue sample, for example by use of probes comprising or consisting of said coding sequences; as well as methods for detecting levels of expression of said product in tissue, e.g. by the use of antibodies capable of specifically reacting with the variant products of the invention. Detection of the level of the expression of the variant of the invention in particular as compared to that of the original sequence from which it was varied or compared to other variant sequences all varied from the same original sequence may be indicative of a plurality of physiological or pathological conditions.

The method, according to this latter aspect, for detection of a nucleic acid sequence which encodes the variant product in a biological sample, comprises the steps of:

(a) providing a probe comprising at least one of the nucleic acid sequences defined above;

(b) contacting the biological sample with said probe under conditions allowing hybridization of nucleic acid sequences thereby enabling formation of hybridization complexes;

(c) detecting hybridization complexes, wherein the presence of the complex indicates the presence of nucleic acid sequence encoding the variant product in the biological sample.

The method as described above is qualitative, i.e. indicates whether the transcript is present in or absent from the sample. The method can also be quantitative, by determining the level of hybridization complexes and then calibrating said levels to determining levels of transcripts of the desired variant in the sample.

Both qualitative and quantitative determination methods can be used for diagnostic, prognostic and therapy planning purposes.

By a preferred embodiment the probe is part of a nucleic acid chip used for detection purposes, i.e. the probe is a part of an array of probes each present in a known location on a solid support.

The nucleic acid sequence used in the above method may be a DNA sequence an RNA sequence, etc; it may be a coding or a sequence or a sequence complementary thereto (for respective detection of RNA transcripts or coding-DNA sequences). By quantization of the level of hybridization complexes and calibrating the quantified results it is possible also to detect the level of the transcript in the sample.

Methods for detecting mutations in the region coding for the variant product are also provided, which may be methods carried-out in a binary fashion, namely merely detecting whether there is any mismatches between the normal variant nucleic acid sequence of the invention and the one present in the sample, or carried-out by specifically detecting the nature and location of the mutation.

The present invention also concerns a method for detecting variant product in a biological sample, comprising the steps of:

(a) contacting with said biological sample the antibody of the invention, thereby forming an antibody-antigen complex; and (b) detecting said antibody-antigen complex wherein the presence of said antibody-antigen complex correlates with the presence of variant product in said biological sample.

As indicated above, the method can be quantitized to determine the level or the amount of the variant in the sample, alone or in comparison to the level of the original amino acid sequence from which it was varied, and qualitative and quantitative results may be used for diagnostic, prognostic and therapy planning purposes.

By yet another aspect the invention also provides a method for identifying candidate compounds capable of binding to the variant product and modulating its activity (being either activators or deactivators). The method includes:

(i) providing a protein or polypeptide comprising an amino acid sequence substantially as depicted in any one of SEQ ID NO: 27 to 52, or a fragment of such a sequence;

(ii) contacting a candidate compound with said amino acid sequence;

(iii) measuring the physiological effect of said candidate compound on the activity of the amino acid sequences and selecting those compounds which show a significant effect on said physiological activity.

The present invention also concerns compounds identified by the above methods described above, which compound may either be an activator of the variant product or a deactivator thereof.

BRIEF DESCRIPTION OF THE DRAWINGS

Detailed Description of a Preferred Embodiment

Example I

Designation of the Original Sequences

Each novel variant of the invention is varied from an original sequence which has a known designation. The designation of the RNA sequences of the original sequences are given below and for each sequence the SEQ ID's of the nucleic acids and amino acids are also given. It should be noted that many times there exists more than one variant (as evidence by several SEQ ID of nucleic acids and amino acids) for each original sequence due to alternative splicing resulting in several splice variants of the same sequence.

Designation of original sequence: AA706212—Insulin receptor-related receptor (IRR)—mRNA HUMIRRA: Human insulin receptor-related receptor (IRR) mRNA, 3' to end SEQ ID of nucleic acid: 1

SEQ ID of amino acid: 43

Designation of original sequence: H66520: Sodium bicarbonate cotransporter 2—mRNA AB012130: Homo sapiens SBC2 mRNA for sodium bicarbonate cotransporter 2, complete cds.

SEQ ID of nucleic acid: 10, 11, 12, 13

SEQ ID of amino acid: 39, 40, 41, 42

Designation of original sequence: HSBNGFAC: Beta nerve growth factor—mRNA HSBNGFAC—Human mRNA for beta nerve growth factor SEQ ID of nucleic acid: 23

SEQ ID of amino acid: 44

Designation of original sequence: HUTMIGFBA: transforming growth factor-beta (TGF-beta)—mRNA HSTGFB 1: Human mRNA for transforming growth factor-beta (TGF-beta)

SEQ ID of nucleic acid: 24, 25

SEQ ID of amino acid: 51, 52

Designation of original sequence: R49883: growth factor receptor-related B-lymphocyte activation molecule—mRNA HSCDW40: Human CDw40 mRNA for nerve growth factor receptor-related B-lymphocyte activatin molecule SEQ ID of nucleic acid: 21

SEQ ID of amino acid: 33

Designation of original sequence: HSDHII061: cAMP-specific phosphodiesterase 8B (PDE8B)—mRNA AF079529*: Homo sapiens* cAMP-specific phosphodiesterase 8B (PDE9B) mRNA, partial cds.

SEQ ID of nucleic acid: 9

SEQ ID of amino acid: 50

Designation of original sequence: HSPDE1A3A: Cyclic nucleotide phosphodiesterase—mRNA HSPDE1A3A: 3', 5' cyclic nucleotide phosphodiesterase (HSPDE1A3A) mRNA, complete eds.

SEQ ID of nucleic acid: 18

SEQ ID of amino acid: 49

Designation of original sequence: HSU58130: bumetanide-sensitive Na-K-2C1 cotransporter (BKCC2)—mRNA HSU58130: Human bumetanide-sensitive Na-K-2C1 cotransporter (NKCC2) mRNA, complete eds.

SEQ ID of nucleic acid: 26

SEQ ID of amino acid: 38

Designation of original sequence: HUMCLPA: Human bile salt-activated lipase (BAL), cholesterol esterase—mRNA HUMLIPBSA: Human bile salt-activated lipase (BAL) mRNA, complete eds.

SEQ ID of nucleic acid: 5, 6, 7, 8

SEQ ID of amino acid: 45, 46, 47, 48

Designation of original sequence: R53112: PDGF receptor beta-like tumor suppressor (PRLTS)—mRNA HUMPRLTS: Human mRNA for PDGF receptor beta-like tumor suppressor (PRLTS), complete eds.

SEQ ID of nucleic acid: 22

SEQ ID of amino acid: 37

Designation of original sequence: HHEA47M: TNF related apoptosis inducing ligand TRAIL—mRNA HSU37518: Human TNF-related apoptosis inducing ligand TRAIL mRNA, complete eds.

SEQ ID of nucleic acid: 14, 15, 16, 17

SEQ ID of amino acid: 29, 30, 31, 32

Designation of original sequence: R02351: serotonin 5-HT3 receptor—mRNA HUMS5HT3RA: Human mRNA for serotonin 5-HT3 receptor, complete cds.

SEQ ID of nucleic acid: 19, 20

SEQ ID of amino acid: 27, 28

Designation of original sequence: AB005060: NTAK, brain-derived member of the epidermal growth factor family that interacts with ErbB3 and ErbB4-mRNA AB005060: Homo sapiens mRNA for NTAK, complete eds.

SEQ ID of nucleic acid: 2, 3, 4

SEQ ID of amino acid: 34, 35, 36

Example II

Variant Nucleic Acid Sequence

The nucleic acid sequences of the invention include nucleic acid sequences which encode variant product and fragments and analogs thereof. The nucleic acid sequences may alternatively be sequences complementary to the above coding sequence, or to a region of said coding sequence. The length of the complementary sequence is sufficient to avoid the expression of the coding sequence. The nucleic acid sequences may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand. The nucleic acid sequences may also both include dNTPs, rNTPs as well as non naturally occurring sequences. The sequence may also be a part of a hybrid between an amino acid sequence and a nucleic acid sequence.

In a general embodiment, the nucleic acid sequence has at least 90%, identity with any one of the sequence identified as SEQ ID NO: 1 to SEQ ID NO: 26 provided that this sequence is not completely identical with that of the original sequence.

The nucleic acid sequences may include the coding sequence by itself. By another alternative the coding region may be in combination with additional coding sequences, such as those coding for fusion protein or signal peptides, in combination with non-coding sequences, such as introns and control elements, promoter and terminator elements or 5' and/or 3' untranslated regions, effective for expression of the coding sequence in a suitable host, and/or in a vector or host environment in which the variant nucleic acid sequence is introduced as a heterologous sequence.

The nucleic acid sequences of the present invention may also have the product coding sequence fused in-frame to a marker sequence which allows for purification of the variant product. The marker sequence may be, for example, a hexahistidine tag to provide for purification of the mature polypeptide fused to the marker in the case of a bacterial host, or, the marker sequence may be a hemagglutinin (HA) tag when a mammalian host, e.g. COS-7 cells, is used. The HA tag corresponds to an epitope derived from the influenza hemagglutinin protein (Wilson, I., et al. *Cell* 37:767 (1984)).

Also included in the scope of the invention are fragments as defined above also referred to herein as oligonucleotides, typically having at least 20 bases, preferably 20–30 bases corresponding to a region of the coding-sequence nucleic acid sequence. The fragments may be used as probes, primers, and when complementary also as antisense agents, and the like, according to known methods.

As indicated above, the nucleic acid sequence may be substantially a depicted in any one of SEQ ID NO: 1 to SEQ ID NO: 26 or fragments thereof or sequences having at least 90% identity to the above sequence as explained above. Alternatively, due to the degenerative nature of the genetic code, the sequence may be a sequence coding for any one of the amino acid sequence of SEQ ID NO: 27 to SEQ ID NO: 52, or fragments or analogs of said amino acid sequence.

A. Preparation of Nucleic Acid Sequences

The nucleic acid sequences may be obtained by screening cDNA libraries using oligonucleotide probes which can hybridize to or PCR-amplify nucleic acid sequences which encode the variant products disclosed above. cDNA libraries prepared from a variety of tissues are commercially available and procedures for screening and isolating cDNA clones are well-known to those of skill in the art. Such techniques are described in, for example, Sambrook et al. (1989) Molecular Cloning: A Laboratory Manual (2nd Edition), Cold Spring Harbor Press, Plainview, N.Y. and Ausubel FM et al. (1989) Current Protocols in Molecular Biology, John Wiley & Sons, New York, N.Y.

The nucleic acid sequences may be extended to obtain upstream and downstream sequences such as promoters, regulatory elements, and 5' and 3' untranslated regions (UTRs). Extension of the available transcript sequence may be performed by numerous methods known to those of skill in the art, such as PCR or primer extension (Sambrook et al., supra), or by the RACE method using, for example, the Marathon RACE kit (Clontech, Cat. # K1802-1).

Alternatively, the technique of "restriction-site" PCR (Gobinda et al. *PCR Methods Applic*. 2:318–22, (1993)), which uses universal primers to retrieve is flanking sequence adjacent a known locus, may be employed. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia, T. et al., *Nucleic Acids Res*. 16:8186, (1988)). The primers may be designed using OLIGO(R) 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Capture PCR (Lagerstrom, M. et al., *PCR Methods Applic*. 1:111–19, (1991)) is a method for PCR amplification of DNA fragments adjacent to a known sequence in human and yeast artificial chromosome DNA. Capture PCR also requires multiple restriction enzyme digestions and ligations to place an engineered double-stranded sequence into a flanking part of the DNA molecule before PCR.

Another method which may be used to retrieve flanking sequences is that of Parker, J. D., et al., *Nucleic Acids Res*., 19:3055–60, (1991)). Additionally, one can use PCR, nested primers and PromoterFinder™ libraries to "walk in" genomic DNA (PromoterFinder™; Clontech, Palo Alto, Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes.

A randomly primed library may be particularly useful if an oligo d(T) library does not yield a full-length cDNA. Genomic libraries are useful for extension into the 5' non-translated regulatory region.

The nucleic acid sequences and oligonucleotides of the invention can also be prepared by solid-phase methods, according to known synthetic methods. Typically, fragments of up to about 100 bases are individually synthesized, then joined to form continuous sequences up to several hundred bases.

B. Use of Variant Nucleic Acid Sequence for the Production of Variant Products

In accordance with the present invention, nucleic acid sequences specified above may be used as recombinant DNA molecules that direct the expression of variant products.

As will be understood by those of skill in the art, it may be advantageous to produce variant product-encoding nucleotide sequences possessing codons other than those which appear in any one of SEQ ID NO: 1 to SEQ ID NO: 26 which are those which naturally occur in the human genome. Codons preferred by a particular prokaryotic or eukaryotic host (Murray, E. et al. *Nuc Acids Res*., 17:477–508, (1989)) can be selected, for example, to increase the rate of variant product expression or to produce recombinant RNA transcripts having desirable properties, such as a longer half-life, than transcripts produced from naturally occurring sequence.

The nucleic acid sequences of the present invention can be engineered in order to alter a variant product coding sequence for a variety of reasons, including but not limited to, alterations which modify the cloning, processing and/or expression of the product. For example, alterations may be introduced using techniques which are well known in the art, e.g., site-directed mutagenesis, to insert new restriction sites, to alter glycosylation patterns, to change codon preference, etc.

The present invention also includes recombinant constructs comprising one or more of the sequences as broadly described above. The constructs comprise a vector, such as a plasmid or viral vector, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook, et al., (supra).

The present invention also relates to host cells which are genetically engineered with vectors of the invention, and the production of the product of the invention by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the expression of the variant nucleic acid sequence. The culture conditions, such as temperature, pH and the like, are those previously used with the host cell selected for expression, and will be apparent to those skilled in the art.

The nucleic acid sequences of the present invention may be included in any one of a variety of expression vectors for expressing a product. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The DNA sequence in the expression vector is operatively linked to an appropriate transcription control sequence (promoter) to direct mRNA synthesis. Examples of such promoters include: LTR or SV40 promoter, the E. coli lac or trp promoter, the phage lambda PL promoter, and other promoters known to control expression of genes in prokaryotic or eukaryotic cells or their viruses. The expression vector also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as described above, as well as an appropriate promoter or control sequence, may be employed to transform an appropriate host to permit the host to express the protein. Examples of appropriate expression hosts include: bacterial cells, such as *E. coli, Streptomyces, Salmonella typhimurium*; fungal cells, such as yeast; insect cells such as Drosophila and Spodoptera Sf9; animal cells such as CHO, COS, HEK 293 or Bowes melanoma; adenoviruses; plant cells, etc. The selection of an appropriate host is deemed to be within the scope of those skilled in the art from the teachings herein. The invention is not limited by the host cells employed.

In bacterial systems, a number of expression vectors may be selected depending upon the use intended for the variant product. For example, when large quantities of variant product are needed for the induction of antibodies, vectors which direct high level expression of fusion proteins that are readily purified may be desirable. Such vectors include, but are not limited to, multifunctional *E. coli* cloning and expression vectors such as Bluescript(R) (Stratagene), in which the variant polypeptide coding sequence may be ligated into the vector in-frame with sequences for the amino-terminal Met and the subsequent 7 residues of beta-galactosidase so that a hybrid protein is produced; pIN vectors (Van Heeke & Schuster *J. Biol. Chem.* 264:5503–5509, (1989)); pET vectors (Novagen, Madison Wis.); and the like.

In the yeast *Saccharomyces cerevisiae* a number of vectors containing constitutive or inducible promoters such as alpha factor, alcohol oxidase and PGH may be used. For reviews, see Ausubel et al. (supra) and Grant et al., (*Methods in Enzymology* 153:516–544, (1987)).

In cases where plant expression vectors are used, the expression of a sequence encoding variant product may be driven by any of a number of promoters. For example, viral promoters such as the 35S and 19S promoters of CaMV (Brisson et al., *Nature* 310:511–514. (1984)) may be used alone or in combination with the omega leader sequence from TMV (Takamatsu et al., *EMBO J.*, 6:307–311, (1987)). Alternatively, plant promoters such as the small subunit of RUBISCO (Coruzzi et al., *EMBO J.* 3:1671–1680, (1984); Broglie et al., *Science* 224:838–843, (1984)); or heat shock promoters (Winter J and Sinibaldi R. M., *Results Probl. Cell Differ.*, 17:85–105, (1991)) may be used. These constructs can be introduced into plant cells by direct DNA transformation or pathogen-mediated transfection. For reviews of such techniques, see Hobbs S. or Murry L. E. (1992) in McGraw Hill Yearbook of Science and Technology, McGraw Hill, New York, N.Y., pp 191–196; or Weissbach and Weissbach (1988) *Methods for Plant Molecular Biology*, Academic Press, New York, N.Y., pp 421–463.

Variant product may also be expressed in an insect system. In one such system, Autographa californica nuclear polyhedrosis virus (AcNPV) is used as a vector to express foreign genes in *Spodoptera frugiperda* cells or in Trichoplusia larvae. The variant product coding sequence may be cloned into a nonessential region of the virus, such as the polyhedrin gene, and placed under control of the polyhedrin promoter. Successful insertion of variant coding sequence will render the polyhedrin gene inactive and produce recombinant virus lacking coat protein coat. The recombinant viruses are then used to infect *S. frugiperda* cells or Trichoplusia larvae in which variant protein is expressed (Smith et al., *J. Virol.* 46:584, (1983); Engelhard, E. K. et al., *Proc. Nat. Acad. Sci.* 91:3224–7, (1994)).

In mammalian host cells, a number of viral-based expression systems may be utilized. In cases where an adenovirus is used as an expression vector, a variant product coding sequence may be ligated into an adenovirus transcription/translation complex consisting of the late promoter and tripartite leader sequence. Insertion in a nonessential E1 or E3 region of the viral genome will result in a viable virus capable of expressing variant protein in infected host cells (Logan and Shenk, *Proc. Natl. Acad. Sci.* 81:3655–59, (1984). In addition, transcription enhancers, such as the Rous sarcoma virus (RSV) enhancer, may be used to increase expression in mammalian host cells.

Specific initiation signals may also be required for efficient translation of a variant product coding sequence. These signals include the ATG initiation codon and adjacent sequences. In cases where variant product coding sequence, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf, D. et al., (1994) *Results Probl. Cell Differ.*, 20:125–62, (1994); Bittner et al., *Methods in Enzymol* 153:516–544, (1987)).

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, I. (1986) Basic Methods in Molecular Biology). Cell-free translation systems can also be employed to produce polypeptides using RNAs derived from the DNA constructs of the present invention.

A host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre-pro" form of the protein may also be important for correct insertion, folding and/or function. Different host cells such as CHO, HeLa, MDCK, 293, W138, etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express variant product may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M., et al., *Cell* 11:223–32, (1977)) and adenine phosphoribosyltransferase (Lowy I., et al., *Cell* 22:817–23, (1980)) genes which can be employed in tk- or aprt- cells, respectively. Also, antimetabolite, antibiotic or herbicide resistance can be used as the basis for selection; for example, dhfr which confers resistance to methotrexate (Wigler M., et al., *Proc. Natl. Acad. Sci.* 77:3567–70, (1980)); npt, which confers resistance to the aminoglycosides neomycin and G-418 (Colbere-Garapin, F. et al., *J. Mol. Biol.*, 150:1–14, (1981)) and als or pat, which confer resistance to chlorsulfuron and phosphinotricin acetyltransferase, respectively (Murry, sapra). Additional selectable genes have been described, for example, trpB, which allows cells to utilize indole in place of tryptophan, or hisD, which allows cells to utilize histinol in place of histidine (Hartman S. C. and R. C. Mulligan, *Proc. Natl. Acad. Sci.* 85:8047–51, (1988)). The use of visible markers has gained popularity with such markers as anthocyanins, beta-glucuronidase and its substrate, GUS, and luciferase and its substrates, luciferin and ATP, being widely used not only to identify transformants, but also to quantify the amount of transient or stable protein expression attributable to a specific vector system (Rhodes, C. A. et. al., *Methods Mol. Biol*., 55:121–131, (1995)).

Host cells transformed with a nucleotide sequence encoding variant product may be cultured under conditions suitable for the expression and recovery of the encoded protein from cell culture. The product produced by a recombinant cell may be secreted or contained intracellularly depending on the sequence and/or the vector used. As will be understood by those of skill in the art, expression vectors containing nucleic acid sequences encoding variant product can be designed with signal sequences which direct secretion of variant product through a prokaryotic or eukaryotic cell membrane.

The variant product may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Ifmunex Corp, Seattle, Wash.). The inclusion of a protease-cleavable polypeptide linker sequence between the purification domain and variant product is useful to facilitate purification. One such expression vector provides for expression of a fusion protein compromising a variant polypeptide fused to a polyhistidine region separated by an enterokinase cleavage site. The histidine residues facilitate purification on IMIAC (immobilized metal ion affinity chromatography, as described in Porath, et al., *Protein Expression and Punrification*, 3:263–281, (1992)) while the enterokinase cleavage site provides a means for isolating variant polypeptide from the fusion protein. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

The variant products can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Protein refolding steps can be used, as necessary, in completing configuration of the mature protein. Finally, high performance liquid chromatography (HPLC) can be employed for final purification steps.

C. Diagnostic Applications Utilizing Nucleic Acid Sequences

The nucleic acid sequences of the present invention may be used for a variety of diagnostic purposes. The nucleic acid sequences may be used to detect and quantitate expression of the variant in patient's cells, e.g. biopsied tissues, by detecting the presence of mRNA coding for variant product. Alternatively, the assay may be used to detect soluble variant in the serum or blood. This assay typically involves obtaining total mRNA from the tissue or serum and contacting the mRNA with a nucleic acid probe. The probe is a nucleic acid molecule of at least 20 nucleotides, preferably 20–30 nucleotides, capable of specifically hybridizing with a sequence included within the sequence of a nucleic acid molecule encoding variant product under hybridizing conditions, detecting the presence of mRNA hybridized to the probe, and thereby detecting the expression of variant. This assay can be used to distinguish between absence, presence, and excess expression of variant product and to monitor levels of variant expression during therapeutic intervention. In addition, the assay may be used to compare the levels of the variant of the invention to the levels of the original sequence from which it has been varied or to levels of other variants, which comparison may have some physiological meaning.

The invention also contemplates the use of the nucleic acid sequences as a diagnostic for diseases resulting from inherited defective variant sequences, or diseases in which the ratio of the amount of the original sequence from which the variant was varied to the novel variants of the invention is altered. These sequences can be detected by comparing the sequences of the defective (i.e., mutant) variant coding region with that of a normal coding region. Association of the sequence coding for mutant variant product with abnormal variant product activity may be verified. In addition, sequences encoding mutant variant products can be inserted into a suitable vector for expression in a functional assay system (e.g., colorimetric assay, complementation experiments in a variant protein deficient strain of HEK293 cells) as yet another means to verify or identify mutations. Once mutant genes have been identified, one can then screen populations of interest for carriers of the mutant gene.

Individuals carrying mutations in the nucleic acid sequence of the present invention may be detected at the DNA level by a variety of techniques. Nucleic acids used for diagnosis may be obtained from a patient's cells, including but not limited to such as from blood, urine, saliva, placenta, tissue biopsy and autopsy material. Genomic DNA may be used directly for detection or may be amplified enzymatically by using PCR (Saiki, et al., *Nature* 324:163–166, (1986)) prior to analysis. RNA or cDNA may also be used for the same purpose. As an example, PCR primers complementary to the nucleic acid of the present invention can be used to identify and analyze mutations in the gene of the present invention. Deletions and insertions can be detected by a change in size of the amplified product in comparison to the normal genotype.

Point mutations can be identified by hybridizing amplified DNA to radiolabeled RNA of the invention or alternatively, radiolabeled antisense DNA sequences of the invention. Sequence changes at specific locations may also be revealed by nuclease protection assays, such RNase and S1 protection or the chemical cleavage method (e.g. Cotton, et al*Proc. Natl. Acad. Sci. USA*, 85:4397–4401, (1985)), or by differences in melting temperatures. "*Molecular beacons*" (Kostrikis L. G. et al., Science 279:1228–1229, (1998)), hairpin-shaped, single-stranded synthetic oligo- nucleotides containing probe sequences which are complementary to the nucleic acid of the present invention, may also be used to detect point mutations or other sequence changes as well as monitor expression levels of variant product. Such diagnostics would be particularly useful for prenatal testing.

Another method for detecting mutations uses two DNA probes which are designed to hybridize to adjacent regions of a target, with abutting bases, where the region of known or suspected mutation(s) is at or near the abutting bases. The two probes may be joined at the abutting bases, e.g., in the presence of a ligase enzyme, but only if both probes are correctly base paired in the region of probe junction. The presence or absence of mutations is then detectable by the presence or absence of ligated probe.

Also suitable for detecting mutations in the variant product coding sequence are oligonucleotide array methods based on sequencing by hybridization (SBH), as described, for example, in U.S. Pat. No. 5,547,839. In a typical method, the DNA target analyte is hybridized with an array of oligonucleotides formed on a microchip. The sequence of the target can then be "read" from the pattern of target binding to the array.

D. Gene Mapping Utilizing Nucleic Acid Sequences

The nucleic acid sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 20–30 bp) from the variant cDNA. Computer analysis of the 3' untranslated region is used to rapidly select primers that do not span more than one exon in the genomic DNA, which would complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids or using instead radiation hybrids are rapid procedures for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., *Human Chromosomes. a Manual of Basic Techniques*, (1988) Pergamon Press, New York.

Once a sequence has been mapped to a precise chromosomal location, the physical position of the sequence on the chromosome can be correlated with genetic map data. Such data are found, for example, in the OMIM database (Center for Medical Genetics, Johns Hopkins University, Baltimore, Md. and National Center for Biotechnology Information, National Library of Medicine, Bethesda, Md.). The OMIM gene map presents the cytogenetic map location of disease genes and other expressed genes. The OMIM database provides information on diseases associated with the chromosomal location. Such associations include the results of linkage analysis mapped to this interval, and the correlation of translocations and other chromosomal aberrations in this area with the advent of polygenic diseases, such as cancer, in general and prostate cancer in particular.

E. Therapeutic Applications of Nucleic Acid Sequences

Nucleic acid sequences of the invention may also be used for therapeutic purposes. Turning first to the second aspect of the invention (i.e. inhibition of expression of variant), expression of variant product may be modulated through antisense technology, which controls gene expression through hybridization of complementary nucleic acid sequences, i.e. antisense DNA or RNA, to the control, 5' or regulatory regions of the gene encoding variant product. For example, the 5' coding portion of the nucleic acid sequence sequence which codes for the product of the present invention is used to design an antisense oligonucleotide of from about 10 to 40 base pairs in length. Oligonucleotides derived from the transcription start site, e.g. between positions −10 and +10 from the start site, are preferred. An antisense DNA oligonucleotide is designed to be complementary to a region of the nucleic acid sequence involved in transcription (Lee et al., *Nucl. Acids, Res.*, 6:3073, (1979); Cooney et al., *Science* 241:456, (1988); and Dervan et al., *Science* 251:1360, (1991)), thereby preventing transcription and the production of the variant products. An antisense RNA oligonucleotide hybridizes to the mRNA in vivo and blocks translation of the mRNA molecule into the variant products (Okano *J. Neurochem.* 56:560, (1991)). The antisense constructs can be delivered to cells by procedures known in the art such that the antisense RNA or DNA may be expressed in vivo. The antisense may be antisense mRNA or DNA sequence capable of coding such antisense mRNA. The antisense mRNA or the DNA coding thereof can be complementary to the full sequence of nucleic acid sequences coding for the variant protein or to a fragment of such a sequence which is sufficient to inhibit production of a protein product.

Turning now to the first aspect of the invention, i.e. expression of variant, expression of variant product may be increased by providing coding sequences for coding for said product under the control of suitable control elements ending its expression in the desired host.

The nucleic acid sequences of the invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The products of the invention as well as any activators and deactivators compounds (see below) which are polypeptides, may also be employed in accordance with the present invention by expression of such polypeptides in vivo, which is often referred to as "gene therapy." Cells from a patient may be engineered with a nucleic acid sequence (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a product of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors mentioned above may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, psi-2, psi-AM, PA12, T19-14X, VT-19-17-H2, psi-CRE, psi-CRIP, GP+E-86, GP+envAm12, and DAN cell lines as described in Miller (*Human Gene Therapy*, Vol. 1, pg. 5–14, (1990)). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The genes introduced into cells may be placed under the control of inducible promoters, such as the radiation-inducible Egr-1 promoter, (Maceri, H. J., et al., *Cancer Res.*, 56(19):4311 (1996)), to stimulate variant production or antisense inhibition in response to radiation, eg., radiation therapy for treating tumors.

Example III

Variant Product

The substantially purified variant product of the invention has been defined above as the product coded from the nucleic acid sequence of the invention. Preferably the amino acid sequence is an amino acid sequence having at least 90% identity to any one of the sequences identified as SEQ ID NO: 27 to SEQ ID NO: 52 provided that the amino acid sequence is not identical to that of the original sequence from which it has been varied. The protein or polypeptide may be in mature and/or modified form, also as defined above. Also contemplated are protein fragments having at least 10 contiguous amino acid residues, preferably at least 10–20 residues, derived from the variant product, as well as homologues as explained above.

The sequence variations are preferably those that are considered conserved substitutions, as defined above. Thus, for example, a protein with a sequence having at least 90% sequence identity with any of the products identified as SEQ ID NO: 27 to 52, preferably by utilizing conserved substitutions as defined above is also part of the invention, and provided that it is not identical to the original peptide from which it has been varied. In a more specific embodiment, the protein has or contains any one of the sequence identified as SEQ ID NO: 27 to 52. The variant product may be (i) one in which one or more of the amino acid residues in a sequence listed above are substituted with a conserved or non-conserved amino acid residue (preferably a conserved amino acid residue), or (ii) one in which one or more of the amino acid residues includes a substituent group, or (iii) one in which the variant product is fused with another compound, such as a compound to increase the half-life of the protein (for example, polyethylene glycol (PEG)), or a moiety which serves as targeting means to direct the protein to its target tissue or target cell population (such as an antibody), or (iv) one in which additional amino acids are fused to the variant product. Such fragments, variants and derivatives are deemed to be within the scope of those skilled in the art from the teachings herein.

A. Preparation of Variant Product

Recombinant methods for producing and isolating the variant product, and fragments of the protein are described above.

In addition to recombinant production, fragments and portions of variant product may be produced by direct peptide synthesis using solid-phase techniques (cf. Stewart et al., (1969) Solid-Phase Peptide Synthesis, WH Freeman Co, San Francisco; Merrifield J., *J. Am. Cliem. Soc.*, 85:2149–2154, (1963)). In vitro peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Fragments of variant product may be chemically synthesized separately and combined using chemical methods to produce the full length molecule.

B. Therapeutic Uses and Compositions Utilizing the Variant Product

The variant product of the invention is generally useful in treating diseases and disorders which are characterized by a lower than normal level of variant expression, and or diseases which can be cured or ameliorated by raising the level of the variant product, even if the level is normal.

Variant products or fragments may be administered by any of a number of routes and methods designed to provide a consistent and predictable concentration of compound at the target organ or tissue. The product-containing compositions may be administered alone or in combination with other agents, such as stabilizing compounds, and/or in combination with other pharmaceutical agents such as drugs or hormones.

Variant product-containing compositions may be administered by a number of routes including, but not limited to oral, intravenous, intramuscular, transdermal, subcutaneous, topical, sublingual, or rectal means as well as by nasal application. variant product-containing compositions may also be administered via liposomes. Such administration routes and appropriate formulations are generally known to those of skill in the art.

The product can be given via intravenous or intraperitoneal injection. Similarly, the product may be injected to other localized regions of the body. The product may also be administered via nasal insufflation. Enteral administration is also possible. For such administration, the product should be formulated into an appropriate capsule or elixir for oral administration, or into a suppository for rectal administration.

The foregoing exemplary administration modes will likely require that the product be formulated into an appropriate carrier, including ointments, gels, suppositories. Appropriate formulations are well known to persons skilled in the art.

Dosage of the product will vary, depending upon the potency and therapeutic index of the particular polypeptide selected.

A therapeutic composition for use in the treatment method can include the product in a sterile injectable solution, the polypeptide in an oral delivery vehicle, the product in an aerosol suitable for nasal administration, or the product in a nebulized form, all prepared according to well known methods. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The product of the invention may also be used to modulate endothelial differentiation and proliferation as well as to modulate apoptosis either ex vivo or in vitro, for example, in cell cultures.

Example IV

Screening Methods for Activators and Deactivators (Inhibitors)

The present invention also includes an assay for identifying molecules, such as synthetic drugs, antibodies, peptides, or other molecules, which have a modulating effect on the activity of the variant product, e.g. activators or deactivators of the variant product of the present invention. Such an assay comprises the steps of providing an variant product encoded by the nucleic acid sequences of the present invention, contacting the variant protein with one or more candidate molecules to determine the candidate molecules modulating effect on the activity of the variant product, and selecting from the molecules a candidate's molecule capable of modulating variant product physiological activity.

The variant product, its catalytic or immunogenic fragments or oligopeptides thereof, can be used for screening therapeutic compounds in any of a variety of drug screening techniques. The fragment employed in such a test may be free in solution, affixed to a solid support, borne on a cell membrane or located intracellularly. The formation of binding complexes, between variant product and the agent being tested, may be measured. Alternatively, the activator or deactivator may work by serving as agonist or antagonist, respectively, of the variant receptor, binding entity or target site, and their effect may be determined in connection with any of the above.

Another technique for drug screening which may be used provides for high throughput screening of compounds having suitable binding affinity to the variant product is described in detail by Geysen in PCT Application WO 84/03564, published on Sep. 13, 1984. In summary, large numbers of different small peptide test compounds are synthesized on a solid substrate, such as plastic pins or some other surface. The peptide test compounds are reacted with the full variant product or with fragments of variant product and washed. Bound variant product is then detected by methods well known in the art. Substantially purified variant product can also be coated directly onto plates for use in the aforementioned drug screening techniques. Alternatively, non-neutralizing antibodies can be used to capture the peptide and immobilize it on a solid support.

Antibodies to the variant product, as described in Example VI below, may also be used in screening assays according to methods well known in the art. For example, a "sandwich" assay may be performed, in which an anti-variant antibody is affixed to a solid surface such as a microtiter plate and variant product is added. Such an assay can be used to capture compounds which bind to the variant product. Alternatively, such an assay may be used to measure the ability of compounds to influence with the binding of variant product to the variant receptor, and then select those compounds which effect the binding.

Example VI

Anti-variant Antibodies/Distinguishing Antibodies

A. Synthesis

In still another aspect of the invention, the purified variant product is used to produce anti-variant antibodies which have diagnostic and therapeutic uses related to the activity, distribution, and expression of the variant product. As indicated above, the antibodies may also be directed solely to amino acid sequences present in the variant but not present in the original sequence, or to sequences present only in the original sequence but not in the variant (distinguishing antibodies).

Antibodies to the variant product or to the distinguishing sequence present only in the variant or only in the original sequence (the latter termed "distinguishing antibodies") may be generated by methods well known in the art. Such antibodies may include, but are not limited to, polyclonal, monoclonal, chimeric, humanized, single chain, Fab fragments and fragments produced by an Fab expression library. Antibodies, i.e., those which inhibit dimer formation, are especially preferred for therapeutic use.

A fragment of the variant product for antibody induction does not require biological activity but have to feature immunological activity; however, the protein fragment or oligopeptide must be antigenic. Peptides used to induce specific antibodies may have an amino acid sequence consisting of at least five amino acids, preferably at least 10 amino acids of the sequences specified in any one of SEQ ID NO: 27 to SEQ ID NO: 52 or in distinguishing sequences present only in the variant or only in the original sequence as explained above. Preferably they should mimic a portion of the amino acid sequence of the natural protein and may contain the entire amino acid sequence of a small, naturally occurring molecule. Short stretches of variant protein amino acids may be fused with those of another protein such as keyhole limpet hemocyanin and antibody produced against the chimeric molecule. Procedures well known in the art can be used for the production of antibodies to variant product.

For the production of antibodies, various hosts including goats, rabbits, rats, mice, etc may be immunized by injection with variant product or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants.

Monoclonal antibodies to variant protein may be prepared using any technique which provides for the production of antibody molecules by continuous cell lines in culture. These include but are not limited to the hybridoma technique originally described by Koehler and Milstein (*Nature* 256:495–497, (1975)), the human B-cell hybridoma technique (Kosbor et al., *Immunol. Today* 4:72, (1983); Cote et al., *Proc. Natl. Acad. Sci*. 80:2026–2030, (1983)) and the EBV-hybridoma technique (Cole, et al., *Mol. Cell Biol*. 62:109–120, (1984)).

Techniques developed for the production of "chimeric antibodies", the splicing of mouse antibody genes to human antibody genes to obtain a molecule with appropriate antigen specificity and biological activity can also be used (Morrison et al., *Proc. Natl. Acad. Sci*. 81:6851–6855, (1984); Neuberger et al., *Nature* 312:604–608, (1984); Takeda et al., *Nature* 314:452–454, (1985)). Alternatively, techniques described for the production of single chain antibodies (U.S. Pat. No. 4,946,778) can be adapted to produce single-chain antibodies specific for the variant protein.

Antibodies may also be produced by inducing in vivo production in the lymphocyte population or by screening recombinant immunoglobulin libraries or panels of highly specific binding reagents as disclosed in Orlandi et al. (*Proc. Natl. Acad. Sci*. 86:3833–3837, 1989)), and Winter G and Milstein C., (*Nature* 349:293–299, (1991)).

Antibody fragments which contain specific binding sites for variant protein may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W. D. et al., *Science* 256:1275–1281, (1989)).

B. Diagnostic Applications of Antibodies

A variety of protocols for competitive binding or immunoradiometric assays using either polyclonal or monoclonal antibodies with established specificities are well known in the art. Such immunoassays typically involve the formation of complexes between the variant product and its specific antibody and the measurement of complex formation. A two-site, monoclonal-based immunoassay utilizing monoclonal antibodies reactive to two noninterfering epitopes on a specific variant product is preferred, but a competitive binding assay may also be employed. These assays are described in Maddox D. E., et al., (*J. Exp. Med*. 158:1211, (1983)).

Antibodies which specifically bind variant product or distinguishing antibodies which bind to sequences which distinguish the variant from the original sequence (as explained above) are useful for the diagnosis of conditions or diseases characterized by expression of the novel variant of the invention (where normally it is not expressed) by over or under expression of variant as well as for detection of diseases in which the proportion between the amount of the variants of the invention and the original sequence from which it varied is altered. Alternatively, such antibodies may be used in assays to monitor patients being treated with variant product, its activators, or its deactivators. Diagnostic assays for variant protein include methods utilizing the antibody and a label to detect variant product in human body fluids or extracts of cells or tissues. The products and antibodies of the present invention may be used with or without modification. Frequently, the proteins and antibodies will be labeled by joining them, either covalently or noncovalently, with a reporter molecule. A wide variety of reporter molecules are known in the art.

A variety of protocols for measuring the variant product, using either polyclonal or monoclonal antibodies specific for the respective protein are known in the art. Examples include enzyme-linked immunosorbent assay (ELISA), radioimmunoassay (RIA), and fluorescent activated cell sorting (FACS). As noted above, a two-site, monoclonal-based immunoassay utilizing monoclonal antibodies reactive to two non-interfering epitopes on variant product is preferred, but a competitive binding assay may be employed. These assays are described, among other places, in Maddox, et al. (supra). Such protocols provide a basis for diagnosing altered or abnormal levels of variant product expression. Normal or standard values for variant product expression are established by combining body fluids or cell extracts taken from normal subjects, preferably human, with antibody to variant product under conditions suitable for complex formation which are well known in the art. The amount of standard complex formation may be quantified by various methods, preferably by photometric methods. Then, standard values obtained from normal samples may be compared with values obtained from samples from subjects potentially affected by disease. Deviation between standard and subject values establishes the presence of disease state.

The antibody assays are useful to determine the level of variant product present in a body fluid sample, in order to determine whether it is being expressed at all, whether it is being overexpressed or underexpressed in the tissue, or as an indication of how variant levels of variable products are responding to drug treatment.

C. Therapeutic Uses of Antibodies

In addition to their diagnostic use the antibodies may have a therapeutical utility in blocking or decreasing the activity of the variant product in pathological conditions where beneficial effect can be achieved by such a decrease. Again, distinguishing antibodies may be used to neutralize differentially either the variant or the original sequence as the case may be.

The antibody employed is preferably a humanized monoclonal antibody, or a human Mab produced by known globulin-gene library methods. The antibody is administered typically as a sterile solution by IV injection, although other parenteral routes may be suitable. Typically, the antibody is administered in an amount between about 1–15 mg/kg body weight of the subject. Treatment is continued, e.g., with dosing every 1–7 days, until a therapeutic improvement is seen.

Although the invention has been described with reference to specific methods and embodiments, it is appreciated that various modifications and changes may be made without departing from the invention.

What is claimed is:

1. An isolated nucleic acid consisting essentially of exons 1–5 and 7–9 of a nucleotide sequence encoding CD40.

2. An isolated nucleic acid sequence which is complementary to the nucleic acid of claim 1.

3. An amino acid sequence encoded by the nucleic acid of claim 1.

4. An expression vector comprising the nucleic acid of claim 1 and control elements for the expression of the nucleic acid in a suitable host.

5. A host cell transfected by the expression vector of claim 4.

6. A composition comprising a pharmaceutically acceptable carrier and as an active ingredient the amino acid sequence of claim 3.

* * * * *